(12) United States Patent
Dziubla et al.

(10) Patent No.: US 8,580,240 B1
(45) Date of Patent: Nov. 12, 2013

(54) COMPOUNDS AND METHODS FOR REDUCING THE OCCURRENCE OF POST-SURGICAL ADHESIONS

(75) Inventors: Thomas Dziubla, Lexington, KY (US); Eugene Kaplan, Lafayette, CA (US); John Mark Medley, Jr., Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 369 days.

(21) Appl. No.: 12/622,239

(22) Filed: Nov. 19, 2009

Related U.S. Application Data

(60) Provisional application No. 61/116,030, filed on Nov. 19, 2008.

(51) Int. Cl.
*A61K 31/74* (2006.01)

(52) U.S. Cl.
USPC ........................................................ 424/78.17

(58) Field of Classification Search
None
See application file for complete search history.

(56) References Cited

U.S. PATENT DOCUMENTS

| | | | |
|---|---|---|---|
| 5,626,863 | A | 5/1997 | Hubbell et al. |
| 6,689,803 | B2 | 2/2004 | Hunter |
| 6,800,296 | B1 | 10/2004 | Langer et al. |
| 6,884,628 | B2 | 4/2005 | Hubbell et al. |
| 6,984,485 | B2 * | 1/2006 | Matson .............................. 435/4 |
| 7,166,570 | B2 | 1/2007 | Hunter et al. |
| 7,294,334 | B1 | 11/2007 | Michal et al. |
| 2004/0001892 | A1 * | 1/2004 | Healy et al. ................... 424/486 |
| 2005/0196421 | A1 | 9/2005 | Hunter et al. |
| 2008/0153900 | A1 | 6/2008 | Hunter |

FOREIGN PATENT DOCUMENTS

| | | |
|---|---|---|
| WO | 0178906 | 10/2001 |
| WO | 03072542 | 9/2003 |
| WO | 2008085794 | 7/2008 |

OTHER PUBLICATIONS

Shojaei et al, Mechanisms of buccal mucoadhesion of novel copolymers of acrylic acid and polyethylene glycol monomethyl ether monomethacrylate, Journal of Controlled Release, 1997, 47, 151-161.*
Dunn, R., et al., Evaluation of the SprayGel adhesion barrier in the rat cecum abrasion and rabbit uterine horn adhesion models. Fertil Steril, 2001. 75(2): p. 411-6.
Ferland, R., D. Mulani, and P.K. Campbell, Evaluation of a sprayable polyethylene glycol adhesion barrier in a porcine efficacy model. Hum Reprod, 2001. 16(12): p. 2718-23.
Hills, B.A., B.D. Butler, and R.E. Barrow, Boundary lubrication imparted by pleural surfactants and their identification. J Appl Physiol, 1982. 53(2): p. 463-9.
Karmali, P.P., et al., Targeting of albumin-embedded paclitaxel nanoparticles to tumors. Nanomedicine, 2009. 5(1): p. 73-82.
Mettler, L., et al., A randomized, prospective, controlled, multicenter clinical trial of a sprayable, site-specific adhesion barrier system in patients undergoing myomectomy. Fertil Steril, 2004. 82(2): p. 398-404.
Muller, S.A., et al., Adhesion prevention comparing liquid and solid barriers in the rabbit uterine horn model. Eur J Obstet Gynecol Reprod Biol, 2005. 120(2): p. 222-6.
Muller, S.A., et al., Efficacy of adhesion prevention and impact on wound healing of intraperitoneal phospholipids. J Surg Res, 2001. 96(1): p. 68-74.
Muller, S.A., et al., Influence of intraperitoneal phospholipid dosage on adhesion formation and wound healing at different intervals after surgery. Langenbecks Arch Surg, 2001. 386(4): p. 278-84.
Nur, I., et al., Commercial fibrin sealants are not equivalent in a rabbit liver-resection model which quantitatively evaluates hemostasis and formation of adhesions. Eur Surg Res, 2005. 37(3): p. 159-65.
Park, J.H., et al., Systematic surface engineering of magnetic nanoworms for in vivo tumor targeting. Small, 2009. 5(6): p. 694-700.
Peters, D.T., Targeting Atherosclerosis: Nanoparticle Delivery for Diagnosis and Treatment, in Biomedical Sciences. 2009, University of California: San Diego. p. 79.
Simberg, D., et al., Biomimetic amplification of nanoparticle homing to tumors. Proc Natl Acad Sci U S A, 2007. 104(3): p. 932-6.
Tulandi, T. and A. Al-Shahrani, Adhesion prevention in gynecologic surgery. Curr Opin Obstet Gynecol, 2005. 17(4): p. 395-8.
Wallwiener, M., et al., Innovative barriers for peritoneal adhesion prevention: liquid or solid? A rat uterine horn model. Fertil Steril, 2006. 86 Suppl 4: p. 1266-76.
Zanuy, D., et al., Influence of the dye presence on the conformational preferences of CREKA, a tumor homing linear pentapeptide. Biopolymers, 2009. 92(2): p. 83-93.
Zanuy, D., et al., The energy landscape of a selective tumor-homing pentapeptide. J Phys Chem B, 2008. 112(29): p. 8692-700.
Zanuy, D., et al., In Silico Molecular Engineering for a Targeted Replacement in a Tumor-Homing Peptide. J Phys Chem B, 2009.

* cited by examiner

*Primary Examiner* — Paul Dickinson

(74) *Attorney, Agent, or Firm* — Stites & Harbison PLLC; Terry L. Wright; Nicolo Davidson

(57) ABSTRACT

Compounds and methods for reducing the occurrence of a post-surgical adhesion are provided. The compounds can include acrylic acid groups and ethylene glycol groups, and can be directed to an area of damaged tissue by the incorporation of a fibrin targeting peptide. The compounds can further include a brush-like portion, capable of creating a steric barrier between a damaged tissue or organ and adjacent tissues or organs, and a targeting portion, capable of directing the compounds to a damaged tissue or organ. Methods of detecting damaged tissue and kits are also provided.

17 Claims, 35 Drawing Sheets

COMPOUNDS AND METHODS FOR REDUCING THE OCCURRENCE OF POST-SURGICAL ADHESIONS

RELATED APPLICATIONS

This application claims priority to U.S. Provisional Application Ser. No. 61/116,030, filed Nov. 19, 2008, the entire disclosure of which is incorporated herein by this reference.

TECHNICAL FIELD

The presently-disclosed subject matter relates to compounds and methods for reducing the occurrence of post-surgical adhesions. In particular, the presently-disclosed subject matter relates to compounds and methods for reducing the occurrence of post-surgical adhesions in a subject using polymeric compounds comprised of acrylic acid groups and ethylene glycol.

BACKGROUND

Each year in the United States, millions of people submit themselves to abdominal surgery for a variety of reasons, including gynecological reconstruction, tumor removal, and Cesarean sections. While the success rate and recovery times for the initial surgeries are continually improving, complications still frequently occur. One major complication of abdominal surgery, occurring in 65-97% of patients, is the formation of post-surgical adhesions [5,6]. Post-surgical adhesions are comprised of acellular, collagen-rich tissue and often form when an organ or tissue is damaged due to inadvertent desiccation or trauma during retraction [17]. During healing, this damaged tissue often becomes attached to adjacent tissues by the formation of a fibrous scar that connects adjacent tissues, resulting in the formation of a post-surgical adhesion.

While these adhesions are generally not problematic and in many cases are asymptomatic, in some cases, these adhesions can lead to serious problems including abdominal or pelvic pain, intestinal obstructions (e.g., bowel obstructions), infertility, or increased difficulty in subsequent surgical procedures that require physician care [5,17,32]. In addition to the immeasurable costs in patient pain and suffering, in the United States alone, an estimated 440,000 adhesiolysis procedures are performed annually to correct issues arising from the formation of adhesions, resulting in annual financial expenditures estimated to exceed $1 billion [7,8].

Numerous attempts have been made to develop approaches to prevent adhesion formation, with the approaches generally being divided into three main categories: modification of surgical procedures [32], biological approaches, and barrier methods [82]. To date, however, no method has been developed that can prevent the formation of adhesions in most or substantially all cases. While improvements in surgical techniques have reduced instances of post-surgical adhesions for some procedures, the most successful methods to prevent adhesions to date have relied on physical barriers to separate damaged tissue surfaces [7,32]. Progress in patient outcomes has been made by using these physical, adhesion barriers, but current barrier methods are still limited by the fact that the barriers must be applied directly to the area of damage. This direct application of the barriers often precludes their application in laparoscopic surgeries and, in many cases, the barriers are unable to prevent certain post-surgical adhesions, as the damaged tissue cannot necessarily be identified or accessed by the surgeon. As such, if damaged tissue is either unknown, inaccessible, or difficult to fully access, current barrier methods will not be effective and adhesion formation remains a likely outcome. To overcome these deficiencies and to prevent the occurrence of post-surgical adhesions, the ability to further protect damaged tissue, including unknown and inaccessible damaged tissue, is thus desired.

SUMMARY

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compounds and methods for reducing the occurrence of post-surgical adhesions in a subject that make use of polymeric compounds that include acrylic acid groups and ethylene glycol.

In some embodiments of the presently-disclosed subject matter, a compound is provided that is comprised of a formula:

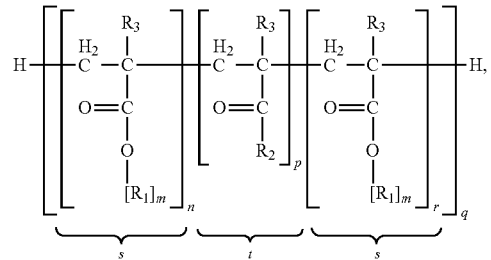

where the $R_1$ group is ethylene glycol; the $R_2$ groups are each independently selected from —OH, —OC(CH$_3$)$_3$, an active group, or a basement membrane targeting peptide, provided at least one $R_2$ is a basement membrane targeting peptide; the $R_3$ groups are each independently selected from H or CH$_3$; m is an integer from about 1 to about 50; n is an integer from about 0 to about 100; p is an integer from about 1 to about 100; r is an integer from about 0 to about 100; and q is an integer from about 1 to about 100. In some embodiments of the presently-disclosed compounds, s is a brush-like portion and t is a targeting portion. In some embodiments, q is an integer from about 30 to about 40. In some embodiments, the ratio of (n+r) to p is about 1 to about 10.

In some embodiments of the presently-disclosed compounds, the active group is selected from a therapeutic agent or a tag, such as, in some embodiments, a fluorescent tag or a radiolabel. In some embodiments, the basement membrane targeting peptide comprises a fibrin targeting peptide, such as, in some embodiments, a fibrin targeting peptide that comprises a sequence of SEQ ID NO: 1.

Further provided, in some embodiments of the presently-disclosed subject matter, are methods for reducing the occurrence of a post-surgical adhesion in a subject. In some embodiments, a method of reducing the occurrence of a postsurgical adhesion is provided that comprises administering to a subject in need thereof an effective amount of a compound of the presently-disclosed subject matter. In some embodiments, reducing the occurrence of a post-surgical adhesion in a subject comprises forming a barrier to maintain tissue separation. In some embodiments, administering an effective amount of the compound comprises rinsing an area of surgical activity with an aqueous solution of the compound.

Still further provided, in some embodiments of the presently-disclosed subject matter, are methods for detecting a damaged tissue in a subject. In some embodiments, a method for detecting a damaged tissue is provided that comprises administering to a subject in need thereof an effective amount of a compound of the presently-disclosed subject matter, where at least one $R_2$ is an active group that is a tag. In some embodiments, the tag is a fluorescent tag. In some embodiments of the methods for detecting a damaged tissue, administering an effective amount of the compound of the presently-disclosed subject matter comprises rinsing an area of surgical activity with an aqueous solution of the compound.

Kits that include a compound of the presently-disclosed subject matter and instructions for using the kit are also provided. In some embodiments, the instructions for using the kit comprise instructions for reducing the occurrence of a post-surgical adhesion. In other embodiments, the instructions for using the kit comprise instructions for detecting a damaged tissue surface.

Advantages of the presently-disclosed subject matter will become evident to those of ordinary skill in the art after a study of the description, Figures, and non-limiting Examples in this document.

BRIEF DESCRIPTION OF THE DRAWINGS

FIG. 11A); a graph showing the specific mass adsorption based on the Sauerbrey model, which assumes a linear fit between frequency response and adsorbed mass (FIG. 11B); a graph showing the kinetic fit of BSA adsorption to the SAM substrate after preadsorption with the exemplary polymeric compound (FIG. 11C; $[SA]_{max}$. ($\alpha/\beta$)=152.1 ng/cm$^2$ and $t_{1/2}$=20.9 s); and a graph showing the kinetic model fit of BSA desorption from the SAM substrate after preadsorption with the exemplary polymeric compound ($[SA]_0$=21.9 ng/cm$^2$ and $t_{1/2}$=27.8 s).

BRIEF DESCRIPTION OF THE SEQUENCE LISTING

Figure 1:
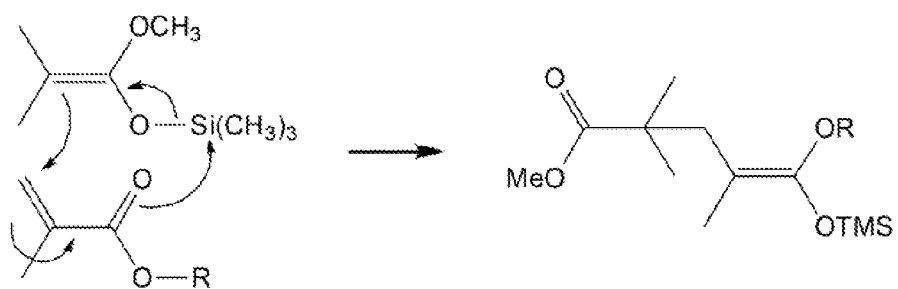
FIG. 1 is a schematic diagram showing a Group Transfer Polymerization (GTP) reaction scheme where 1-methoxy-2-methyl-1-trimethylsiloxypropene (MTS) is transferred from the initiator molecule to the end of a polymer chain.

SEQ ID NO: 1 is an amino acid sequence of a fibrin targeting peptide.

SEQ ID NO: 2 is an amino acid sequence similar to the amino acid sequence of SEQ ID NO: 1, but where the order of the amino acid residues is scrambled.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well-understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a tissue" includes a plurality of such tissues, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently-disclosed subject matter includes compounds and methods for reducing the occurrence of post-surgical adhesions. The phrase "post-surgical adhesion" and the term "adhesion," which are used interchangeably herein, refer to fibrous bridges that form between tissues, between organs, and/or between tissues and organs, often as a result of injury during surgery. Adhesions form as a natural part of a body's healing process. The formation of adhesions typically begins with an acute inflammatory response, including the deposition of fibrin onto injured tissues and organs as well as macrophage penetration, and is followed by the formation of a fibrin gel matrix. (For additional guidance regarding the formation of a fibrin gel matrix and the mechanism of fibrin deposition, see, Boland G M, Weigel R J (2006) J Surg Res 132, 3-12; diZerega GS (1997) Eur J Surg Suppl, 10-16; and, Faucheux N, et al. (2004) Biomaterials, 25, 2721-2730, each of which is incorporated herein by this reference.) When this process initiates on an open surface, typical wound healing is observed, including scar formation. However, if an opposing surface is bridged by fibrin or the fibrin gel matrix, the resulting scar tissue can permanently connect these tissues and result in the formation of an adhesion.

In some embodiments of the presently-disclosed subject matter, a compound for reducing the occurrence of post-surgical adhesions is provided. In some embodiments, a compound is provided that comprises a compound of the following Formula I:

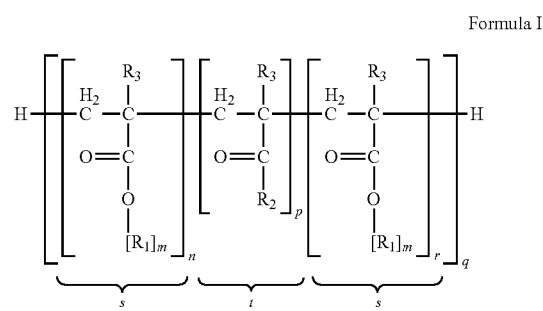

Formula I where $R_1$ is ethylene glycol; each $R_2$ is independently selected from a hydroxyl group (—OH), —C(CH$_3$)$_3$, an active group, and a basement membrane targeting peptide, provided at least one $R_2$ is a basement membrane targeting peptide; each $R_3$ is independently selected from H and CH$_3$; m is an integer from about 1 to about 50; n is an integer from about 0 to about 100; p is an integer from about 1 to about 100; r is an integer from about 0 to about 100; and q is an integer from about 1 to about 100. As noted, each $R_2$ is independent and each $R_3$ is independent. As such, when multiple $R_2$ groups are present, it is possible for one $R_2$ group to be, for example, —OH, —C(CH$_3$)$_3$, or an active group, so long as at least one $R_2$ group is a basement membrane targeting peptide. Similarly, when multiple $R_3$ groups are present, each group can be independently selected from H or CH$_3$.

When m is greater than 1, a polyethylene glycol moiety results. It is further noted that each m is independent of one another. In this regard, each m can be the same or different integers. For example, in one embodiment, a first m can be 20, while a second m can be 25, and a third m can be 30. For another example, in one embodiment, each m can be 20. By way of providing another example, in the following Formula II, n equals 2, p equals 1, r equals 0, a first m is 20 and a second m is 25:

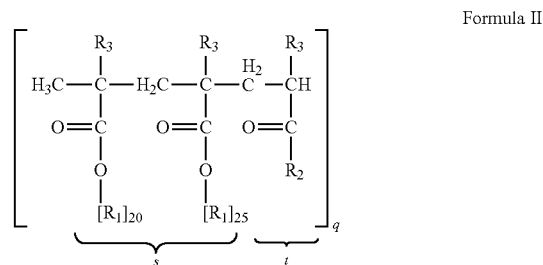

Formula II

In some embodiments, the compound is described as having discreet portions. Such portions can include, a brush-like portion, identified by "s", and a targeting portion, identified by "t," and are described herein below.

As indicated in Formula I, the $R_1$ groups are linked to the compound by an ester linkage, which connects the $R_1$ groups to the acrylic acid groups that form the backbone of the compound. "Acrylic acid" or "acrylate" refers to a group of a general formula:

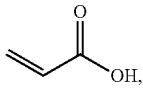

which can be modified to include various groups including, but not limited to, methyl groups. As such, the term "acrylic acid group" is inclusive of acrylic acid groups and methacrylic acid groups. It is further noted that the acrylic acid groups can readily polymerize to form a polymeric backbone where the acrylic acid group monomers are of a general formula:

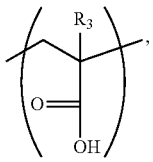

where $R_3$ can be H (e.g., with acrylic acid) or $CH_3$ (e.g., with methacrylic acid). In some embodiments, the hydroxyl (—OH) portion of the carboxylic acid group of the acrylic acid monomers is used to attach various groups (e.g., $R_1$ or $R_2$ groups) to the acrylic acid group backbone via an ester linkage to facilitate in vivo biodegradation. Examples of various groups that can be attached to the acrylic acid group backbone include, but are not limited to, groups such as ethylene glycol, t-butyl groups, active groups, and basement membrane targeting peptides. It is noted that the ester linkage describes the manner in which embodiments of the compound can be produced. In this regard, for example, when a t-butyl group is attached to the acrylic group backbone, the $R_2$ group of the resulting compound can be identified as $—OC(CH_3)_3$.

With further reference to Formula I, the compounds of the presently-disclosed subject matter are described as comprising multiple units, including a unit identified by "n," a unit identified by "p," and a unit identified by "r". Each unit includes an acrylic acid group monomer linked to an $R_1$ or an $R_2$ group. In some embodiments, n is an integer of 0, about 1, about 2, about 3, about 4, about 5, about 10, about 20, about 30, about 40, about 50, about 60, about 70, about 80, about 90, about 95, or about 100. In some embodiments, p is an integer of about 1, about 2, about 3, about 4, about 5, about 10, about 20, about 30, about 40, about 50, about 60, about 70, about 80, about 90, about 95, or about 100. In some embodiments, r is an integer of 0, about 1, about 2, about 3, about 4, about 5, about 10, about 20, about 30, about 40, about 50, about 60, about 70, about 80, about 90, about 95, or about 100. By way of providing an example, in the following Formula III, n is 2, p is 3, and r is 0:

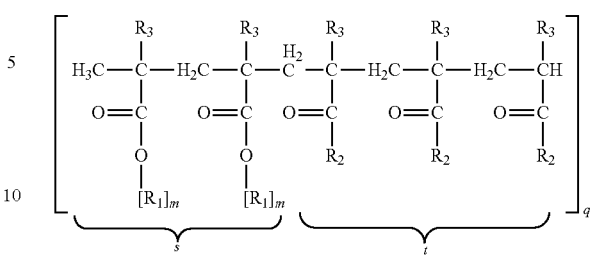

Formula III

Referring again to Formula I, and specifically to the component identified by "q", in some embodiments, the compounds include a series of components, q, that include at least one n-unit and at least one p-unit. In this regard, in embodiments where q is >1, a series of alternating n- and p-units can be provided, each n-unit including an acrylic acid group monomer and an $R_1$ group, and each p-unit including an acrylic acid group monomer and an $R_2$ group. By way of providing an example, in the following Formula IV, q is 2, n is 1, p is 1, and r is 0:

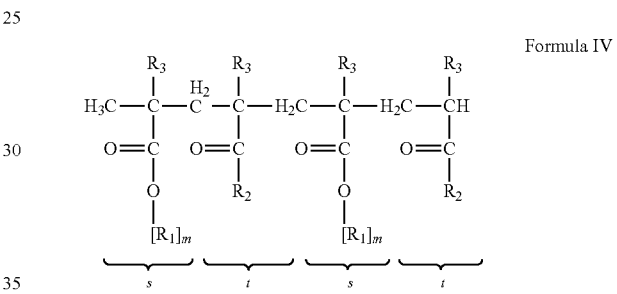

Formula IV

By way of providing another example, in the following Formula V, q is 2, n is 2, p is 1, and r is 0:

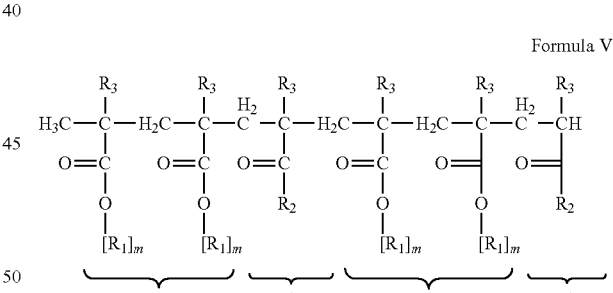

Formula V

In some embodiments of the presently-disclosed subject matter, the compound can include a series of alternating s- and t-portions. It is noted that in some embodiments, it is not necessary that a compound of the presently-disclosed subject matter terminate on a first side with an s-portion and on a second side a t-portion. In some embodiments, a compound of the presently-disclosed subject matter can be provided where the compound can terminate on a first and second side with an s-portion; on a first and second side with a t-portion; or, on a first side with an s-portion and on a second side with a t-portion. By way of providing an example, in the following Formula VI, a compound of the presently-disclosed subject matter is provided where the compound terminates on a first and second side with an s-portion, n is 1, p is 1, r is 1, and q is 1:

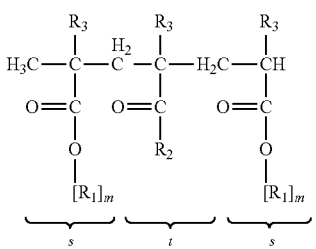

Formula VI

Without wishing to be bound by any particular theory, it is believed that the longer the chains of polymers become (e.g., by increasing q, n, p and/or r), the barrier that is formed by the present compounds becomes increasingly stable. As such, in some embodiments of the presently-disclosed compounds, q is about 1, about 2, about 3, about 4, about 5, about 10, about 20, about 30, about 40, about 50, about 60, about 70, about 80, about 90, about 95, or about 100. In some embodiments, q is an integer from about 30 to about 40.

In some embodiments, the ratio of (n+r) to p is about 1 to about 10. Without wishing to be bound by any particular theory, it is believed that as the number of units of groups of acrylic acid group monomers linked to $R_2$ groups increases, increased binding of the compounds to fibrin and other proteins which form the fibrin gel matrix can occur and thus allow for the proteins involved in the formation of adhesions to be inactivated. By way of providing an example, in the following Formula VII, q is 1, n is 3, p is 2, r is 0, and the ratio of (n+r) to p is 3:2 (or 1.5:1).

Formula VII

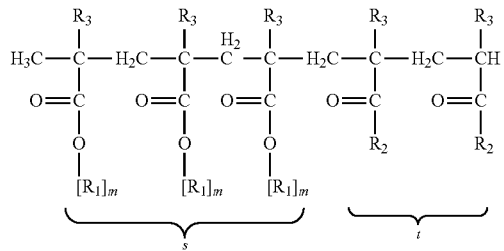

In some embodiments, the compounds of the presently-disclosed subject matter can be described as including a brush-like portion, s, with an anti-adhesive character and a targeting portion, t. In some embodiments, the brush-like portion, s, is comprised of ethylene glycol monomers, or polymers thereof, which are capable of forming a brush-like or steric barrier to reduce the occurrence of adhesions. In some embodiments, s can be comprised of any anti-adhesive polymeric material that can be used to form a steric barrier to reduce the occurrence of adhesions. In some embodiments, the formation of a steric barrier occurs by the brush-like portion, s, replacing the pro-adhesive areas of damaged organs or tissues with an adhesion resistant (poly)ethylene glycol layer to maintain separation of adjacent tissues and organs subsequent to damage of a tissue or organ.

The targeting portion, t, serves to specifically direct the compounds to damaged tissues or organs of a subject, thereby reducing the compounds interaction with non-specific locations and increasing the availability of the compounds at the site of injury. In some embodiments, the targeting portion, t, of the compounds can be directed to damaged organs or tissues by providing a negative charge on the targeting portion that adsorbs to positively charged areas of a basement membrane as many of the components of a basement membrane (e.g., fibronectin or laminin) contain many positively charged amino acid residues (e.g., arginine or lysine residues). In some embodiments, targeting of the compounds to damaged tissues or organs can occur by including a basement membrane targeting peptide in the targeting portion of the present compounds to specifically direct the compounds to a basement membrane. For example, in some embodiments, at least one $R_2$ of at least one targeting portion can be a fibrin targeting peptide, capable of directing the compounds to fibrin proteins of a basement membrane.

It is noted that, in some embodiments where q is greater than 1, there can be multiple brush-like portions and multiple targeting portions of the compound. For example, in the foregoing Formula V, where q is 2, the compound can include two brush-like portions and two targeting portions. In some embodiments, a compound of the presently-disclosed-subject matter can be provided that comprises 2 or 3 or more p-units that are adjacent to one another and are further linked to one or more n- or r-units.

For example, in some embodiments of the presently-disclosed subject matter, a compound is provided that comprises a compound of the following Formula VIII:

Formula VIII

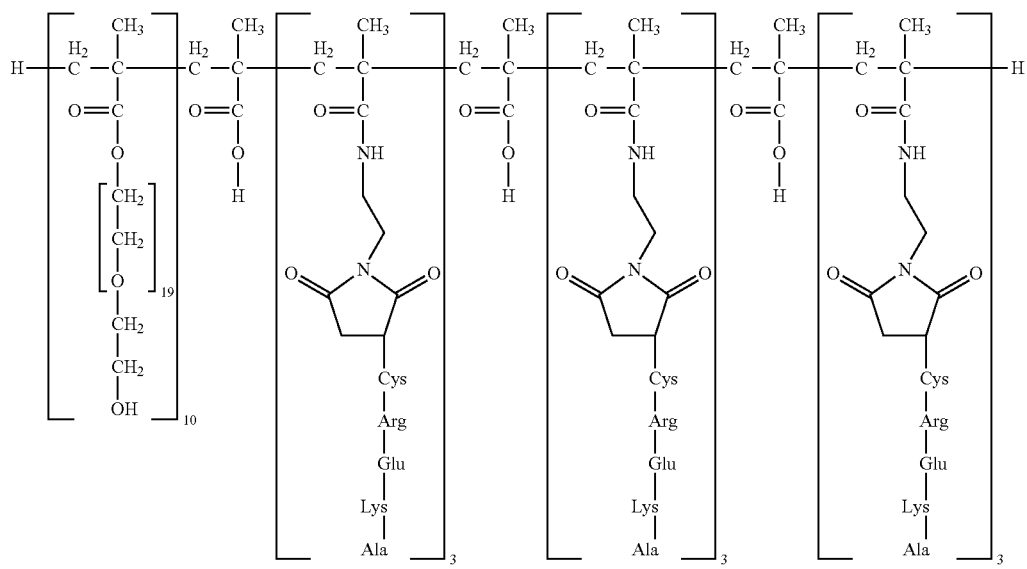

where $R_1$ is an ethylene glycol polymer (i.e., polyethylene glycol) comprised of 20 ethylene glycol monomers; nine $R_2$ groups are comprised of a fibrin targeting peptide that is a peptide of a sequence comprising cysteine-arginine-glutamic acid-lysine-alanine (CREKA; SEQ ID NO: 1) and three $R_2$ groups are —OH; $R_3$ is $CH_3$; M is 20; n is 10; p is 12; r is 0; and, q is 1. In some embodiments, a basement membrane targeting peptide can be conjugated to a compound of the presently-disclosed subject matter by the addition of a maleimide group. For example, as indicated in Formula VIII and described herein in the Examples, a maleimide group can be attached to a compound of the presently-disclosed subject matter and then conjugated to a CREKA peptide by attaching the maleimide group to the thiol (—SH) portion of the cysteine residue of the CREKA polypeptide.

In some embodiments, the compounds of the presently-disclosed subject matter self-assemble. The term "self-assemble," and grammatical variations thereof, relates to any molecular associations or interactions that can occur to allow the compounds of the presently-disclosed subject matter to assemble onto the surface of a basement membrane. For example, when the presently-described compounds absorb to sites of injury in vivo by adhering to fibrin proteins, the compounds are then able to assemble around the fibrin proteins to form barriers that are capable of reducing the formation of adhesions across an entire area of damaged tissue, while still allowing the remainder of the fibrin gel matrix to be left open for cell migration and/or the passage of exudate.

Figure 22:
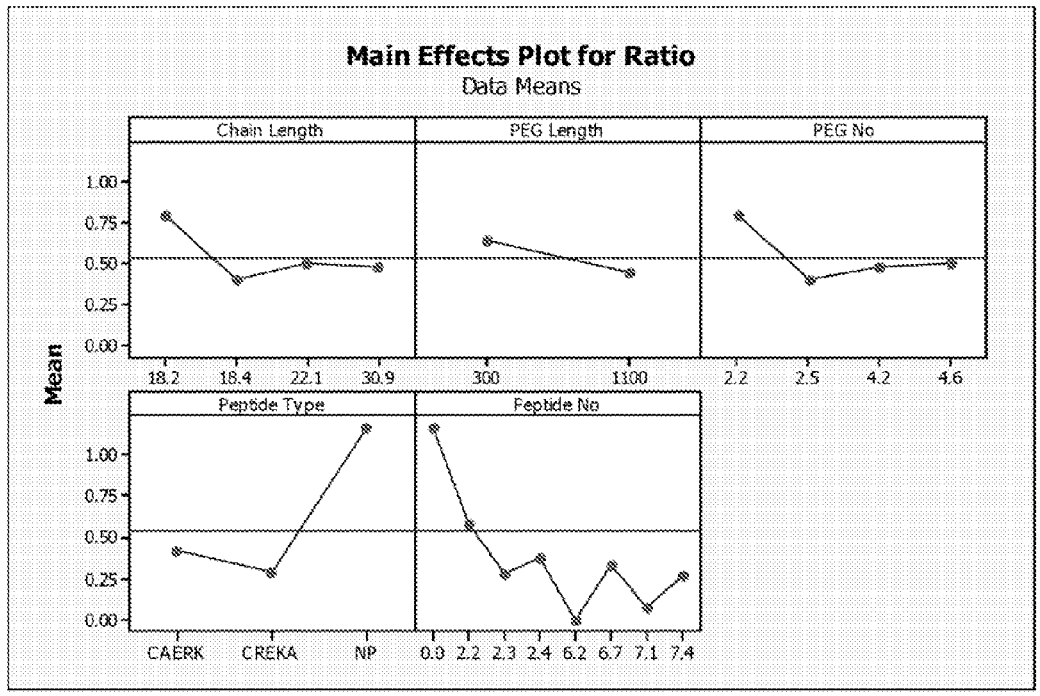
FIG. 22 includes graphs showing the main effects plots for the fibrinogen absorption ratios presented in FIGS. 18-20, and showing the results of varying certain aspects of the polymeric compounds.

As noted above, the $R_1$ groups, or ethylene glycol groups, of the presently-disclosed compounds can be linked to the acrylic acid group backbone via an ester linkage. The term "ethylene glycol" refers to an alcohol with two hydroxyl groups (e.g., a diol) of a general formula: $HOCH_2CH_2OH$. In some embodiments, the ethylene glycol can polymerize to form polymers of "polyethylene glycol," of a general formula $HO(CH_2CH_2O)_nH$. In some embodiments, the number of ethylene glycol groups, or m, that comprise the polymers of polyethylene glycol can be about 1, about 5, about 10, about 15, about 20, about 35, about 40, about 45, or about 50. Without wishing to be bound by any particular theory, and from the results depicted in FIG. 22, it is believed that as the polyethylene glycol chains increase in length, adhesion resistance is improved.

In some embodiments, $R_2$ can be a basement membrane targeting peptide or an active group. The term "active group" is used herein to refer to various groups which can be attached to the presently-disclosed compounds to add to the functionality of the compounds. Such active groups can be incorporated into a compound of the presently-disclosed subject matter utilizing a variety of methods known to those of ordinary skill in the art including, but not limited to: using amine-directed functional groups; using maleimide-thiol conjugation techniques; using carboxylic acid-amine conjugation techniques; and using "click" chemistry techniques. In some embodiments, the active group can be selected from therapeutic agents or tags. For example, in some embodiments, the active group is a tag, such as a fluorescent tag or radiolabel, as described below. As another example, in some embodiments, the active group can be a therapeutic agent that is used to treat damaged tissues.

The term "therapeutic agents" is used herein to refer to those agents which are capable of "treating" damaged tissue. The terms "treatment" or "treating" include, but are not limited to, inhibiting the progression of damage to a tissue, arresting the development of damage to a tissue, reducing the severity of damage to a tissue, ameliorating or relieving symptoms associated with damage to a tissue, and causing a regression of damaged tissue or one or more of the symptoms associated with a damaged tissue. For example, in some embodiments, the therapeutic agent is an agent that reduces the inflammatory response that occurs after tissue is damaged or decreases the likelihood that an infection will develop in a damaged tissue.

Examples of therapeutic agents include, but are not limited to, steroidal anti-inflammatory agents such as betamethasone, triamcinolone dexamethasone, prednisone, mometasone, fluticasone, beclomethasone, flunisolide, and budesonide; non-steroidal anti-inflammatory agents such as fenoprofen, flurbiprofen, ibuprofen, ketoprofen, naproxen, oxaprozin, diclofenac, etodolac, indomethacin, ketorolac, nabumetone, sulindac tolmetin meclofenamate, mefenamic acid, piroxicam, and suprofen; antibiotics such as aminoglycosides, ansamycins, carbacephem, carbapenems, cephalosporins, glycopeptides, macrolides, monobactams, penicillins, polypeptides, quinolones, sulfonamides, and tetracyclines; antioxidants such as vitamin E, trolox, polyphenols, n-acetyl cysteine, and glutathione; pro-resolution agents such as lipoxin A4, resolvins, and Omega-3 fatty acids; anti-fibrotic agents such as perfinidone; or immunosuppressive agents such as cyclophosphamide.

As noted herein above, in some embodiments of the presently-disclosed subject matter, $R_2$ is a basement membrane targeting peptide. The term "basement membrane" is used herein to refer to the extracellular protein layer which surrounds epithelial cells that line the surfaces of tissues and organs throughout the body and connects the epithelial cells to the surrounding loose connective tissue. Proteins found in basement membranes include, but are not limited to, proteins such as fibrin, fibrinogen, fibronectin, collagen (type I and type II), laminin, integrin, entactin, and dystroglycan, as well as many others. As such, the phrase "basement membrane targeting peptide" is used herein to refer to peptides which preferentially bind to one or more of the proteins found in basement membranes. In some embodiments, the basement membrane targeting peptide comprises a fibrin targeting peptide. In some embodiments, the fibrin targeting peptide is a peptide of the sequence: cysteine-arginine-glutamic acid-lysine-alanine (CREKA; SEQ ID NO: 1) that is capable of directing a compound of the presently-disclosed subject matter to fibrin proteins at the site of damaged tissues, such that the "brush-like" portions of the compounds can then act to form a steric barrier over the damaged tissue and reduce the occurrence of a post-surgical adhesion.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins, and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments, and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide. Thus, a fragment of a peptide is intended to encompass the fragment as well as the full-length peptide.

The presently-disclosed subject matter further includes a method for reducing the occurrence of a post-surgical adhesion in a subject. In some embodiments, a method for reducing the occurrence of a post-surgical adhesion comprises administering to a subject in need thereof an effective amount of a compound of Formula I:

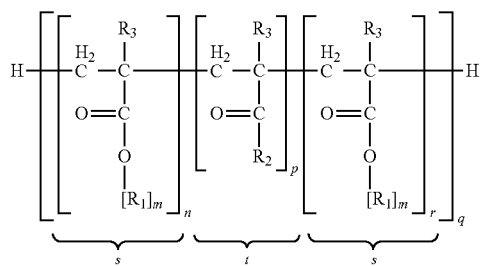

Formula I where $R_1$ is ethylene glycol; $R_2$ is selected from the group consisting of —OH, —C(CH$_3$)$_3$, an active group, and a basement membrane targeting peptide; $R_3$ is selected from the group consisting of H and CH$_3$; m is an integer from about 1 to about 50; n is an integer from about 0 to about 100; p is an integer from about 1 to about 100; r is an integer from about 0 to about 100; and q is an integer from about 1 to about 100, and where s is a brush-like portion and t is a targeting portion.

As used herein in reference to the occurrence of post-surgical adhesions, the terms "reduction" and "reducing" relate to any decrease in the occurrence of a post-surgical adhesion that forms following damage to a tissue or organ, including, but not limited to, a reduction in the amount (number) of post-surgical adhesions; any decrease in the surface area of post-surgical adhesions; and any reduction in the severity of post-surgical adhesions. It is understood that the degree of reduction need not be absolute (i.e., the degree of reduction need not be a complete prevention of the development of a post-surgical adhesion such that the subject does not develop an adhesion at all) and that intermediate levels of reductions in the occurrence of post-surgical adhesions are contemplated by the presently-disclosed subject matter. As such, in some embodiments where the reduction can be assessed or estimated in numerical terms, the reduction in the occurrence of a post-surgical adhesion can be about 5%, about 10%, about 15%, about 20%, about 25%, about 30%, about 50%, about 75%, about 80%, about 85%, about 90%, about 95%, about 99%, or about 100%.

In some embodiments, reducing the occurrence of a post-surgical adhesion comprises forming a barrier to maintain tissue separation. As noted herein above, the compounds of the presently-disclosed subject matter include a targeting portion, capable of directing the compound to a damaged tissue or organ, and a brush-like portion, capable of creating a steric barrier between the tissue or organ and adjacent tissues or organs. In this manner, the compounds can reduce the occurrence of adhesions by replacing exposed pro-adhesive areas of damaged organs or tissues with an adhesion resistant poly (ethylene glycol) layer to maintain separation of adjacent tissues and organs subsequent to damage of a tissue or organ.

As such, in some embodiments, the compounds of the presently-disclosed subject matter are administered to a subject who is undergoing surgery, (e.g., abdominal surgery) and is at risk of developing post-surgical adhesions (e.g., a subject in need thereof), to form a barrier between adjacent tissues and thus maintain separation of the damaged tissues from surrounding tissues to prevent the formation of surgical adhesions. For example, after a surgical procedure is completed but before the initial incision is closed, a compound of the presently-disclosed subject matter can be administered to a subject whose tissues and/or organs have been damaged during the surgical procedure in order to maintain separation of the damaged tissues from the surrounding tissues and/or organs, and thus reduce the occurrence of post-surgical adhesions.

For administration of a compound as disclosed herein, the compounds can be applied to an area of surgical activity as aqueous solutions. For example, the compounds can be combined with a physiologically-acceptable carrier or diluent such as water, glycerine, sorbital, or other generally regarded as safe (GRAS) and/or physiologically-acceptable excipients, including, for example, 5% dextrose, 0.9% saline, Ringer's solution or other suitable excipients, to produce an aqueous solution that can then be sprayed onto an area of surgical activity or can be used as a wash where the area of surgical activity is rinsed with an aqueous solution of the compound. As such, in some embodiments of the presently-disclosed subject matter, the administering an effective amount of the compound comprises rinsing an area of surgical activity with an aqueous solution of the compound. In some embodiments, solutions including a compound of the presently-disclosed subject matter can be administered to a subject prior to or following surgical procedures.

The term "effective amount" is used herein to refer to an amount of a therapeutic compound (e.g., a compound of the presently-disclosed subject matter) sufficient to produce a measurable biological response (e.g., a reduction in the occurrence of a post-surgical adhesion). Actual dosage levels of active ingredients in a compound of the presently-disclosed subject matter can be varied so as to administer an amount of the compound that is effective to achieve the desired response for a particular subject and/or application. The selected dosage level will depend upon a variety of factors including the activity of the compound, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, can be made by those of ordinary skill in the art of medicine. In some cases, such determinations and adjustments can be made based on reasonable experimentation, as will be apparent to those of ordinary skill in the art of medicine.

The phrase "area of surgical activity" is used herein to refer to areas of a body of a subject that are susceptible to tissue or organ damage during surgery (e.g., due to inadvertent tissue desiccation or trauma during surgical retraction) and are thus likely to be susceptible to the formation of tissue adhesions. For example, during abdominal surgery, such as laparoscopic surgery, gynecological reconstruction, tumor removal, or Cesarean sections, the areas of surgical activity include not only those tissues and organs that are being operated upon but also those tissues or organs that can be become desiccated when the peritoneal cavity is left open for an extended period of time, or those tissues and organs of the abdominal cavity that are inadvertently damaged during surgery due to surgical retraction of the tissues.

Further provided, in some embodiments of the presently-disclosed subject matter, is a method of detecting a damaged tissue surface that comprises administering to a subject in need thereof an effective amount of a compound of Formula I:

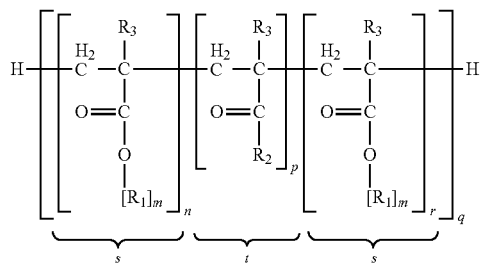

Formula I where $R_1$ is ethylene glycol; $R_2$ is selected from the group consisting of —OH, —C(CH$_3$)$_3$, an active group, and a basement membrane targeting peptide, provided at least one $R_2$ is an active group that is a tag (e.g., fluorescent tag or a radiolabel); m is an integer from about 1 to about 50; n is an integer from about 0 to about 100; p is an integer from about 1 to about 100; r is an integer from about 0 to about 100; and q is an integer from about 1 to about 100, and where s is a brush-like portion and t is a targeting portion.

The terms "detect," "detecting," and grammatical variations thereof, are used herein to refer to determining the presence or absence and/or measuring the amount of damaged tissue. As such, "detecting" a damaged tissue surface can refer to a determination of whether tissue damage is present or absent as well as quantifying the amount of tissue damage that is present. For example, to quantify the amount of damaged tissue in a subject undergoing abdominal surgery, a tag (e.g., fluorescent tag or radiolabel) can be attached to a compound of the presently-disclosed subject matter and administered to a subject via an aqueous solution of the compound. The portion of the aqueous solution containing unbound compounds can then be washed off and the amount of bound compound can be detected by fluorescent imaging or via radiologic methods. To quantify the amount of damaged tissue, signal intensity of the bound fluorescent compounds or the amount of radioactive particles can be detected by methods known to those of ordinary skill in the art.

As used herein, the term "tag" refers to a moiety that can be attached to a compound of the presently-disclosed subject matter and that is capable of detection by radiologic, fluorescent, luminescent, or other detection methods known to those of ordinary skill in the art. For example, in some embodiments, the tag can be a radiolabel that can be detected by radiologic methods known to those of ordinary skill in the art. The terms "radiolabel" or "radiolabeled" are used herein to refer to the incorporation or attachment, optionally covalently or non-covalently, of a detectable marker into a molecule, such as a compound of the presently-disclosed subject matter. Various methods of radiolabeling compounds are known in the art and can be used. Examples of radiolabels that can be attached to a compound of the presently-disclosed subject matter include, but are not limited to, short-lived gamma emitting radiolabels.

In some embodiments, the tag is a fluorescent tag. Fluorescent tags that can be utilized with the compounds of the presently-disclosed subject matter include, but are not limited to: fluorescein isothiocyanate; fluorescein dichlorotriazine and fluorinated analogs of fluorescein; ALEXFLUOR® 488; naphthofluorescein carboxylic acid and its succinimidyl ester; carboxyrhodamine 6G; pyridyloxazole derivatives; Cy2, 3, 3.5, 5, 5.5, and 7; phycoerythrin; phycoerythrin-Cy conjugates; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives (e.g., hydroxycoumarin, aminocoumarin, and methoxycoumarin); pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diaza-s-indacene; Alexa fluors (e.g., 350, 430, 488, 532, 546, 555, 568, 594, 633, 647, 660, 680, 700, and 750); green fluorescent protein; and yellow fluorescent protein. Each of the foregoing fluorescent tags can be incorporated into a compound of the presently-disclosed subject matter using techniques known to those of ordinary skill in the art, such as by using amine directed functional groups, maleimide-thiol conjugation, carboxylic acid-amine conjugation, and "click" chemistry techniques. The peak excitation and emission wavelengths will vary for these compounds and selection of a particular fluorescent tag for a particular application can be made in part based on excitation and/or emission wavelengths. In some embodiments, the fluorescent tag is lissamine rhodamine B ethylenediamine, which excites in the visible range.

Still further provided, in some embodiments of the presently-disclosed subject matter, are kits. In some embodiments, a kit is provided that comprises a compound of the presently-disclosed subject matter and instructions for using the kit. In some embodiments, the instructions for using the kit comprise instructions for reducing the occurrence of a post-surgical adhesion. In some embodiments, the instructions for using the kit comprise instructions for detecting a damaged tissue surface.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples. Some of the following examples are prophetic, notwithstanding the numerical values, results and/or data referred to and contained in the examples. Additionally, the following examples can include compilations of data that are representative of data gathered at various times during the course of development and experimentation related to the present invention.

EXAMPLES

Example 1

Polymer Synthesis and Characterization

To synthesize an exemplary polymeric compound of the presently-disclosed subject matter, methacrylic acid was selected as the monomer for the polymer backbone for its ability to be readily functionalized with a variety of functional groups and for its biocompatibility, which minimizes the potential for adverse biological reactions [128-131]. While some studies have employed polyacrylic acid as an adjuvant to heighten the body's immune response to vaccination formulations, the nature of those reactions was believed to stem from the high molecular weight and the large concentration of acidic units employed [132,133]. As such, in designing an exemplary polymeric compound of the presently-disclosed subject matter, this effect was minimized by reducing the length of the polyacrylic acid block and by minimizing the charge on the final polymeric compound.

In order to provide resistance to the adsorption of proteins and interrupt subsequent adhesion formation, polyethylene glycol (PEG) was chosen for inclusion in the polymeric compounds, as it provides protection from protein adsorption and from immunological responses in vivo [134,135]. Because of the highly hydrophilic nature of PEG, water associates strongly with PEG in aqueous environments and the polymer typically exists in a gel state, which resembles an extracellular matrix and provides high steric protection in a subject [83,136]. To incorporate PEG into the present polymer systems, commercially available methoxy polyethylene glycol methacrylate with a PEG chain length of approximately 25 repeat units (MPEGMA$_{1100}$, Aldrich) was selected for use in some applications.

Further, the target molecular weight for polymer synthesis was chosen to provide a high reduction in protein adsorption, but to also assist in the rapid renal clearance of any polymeric compound entering the blood stream. It has previously been demonstrated that the maximum reduction in protein adsorption is observed with PEG chains with a molecular weight of 5,000 g/mol [140]. As such, the initial polymeric compound that was synthesized incorporated a block of t-butylmethacrylate (TBMA) and a block of MPEGMA, with the target molecular weights of each of these units being set at 5,000 g/mol. In all of the polymeric compounds, however, the maximum molecular weight of the polymeric compound was set at 50,000 g/mol to assist in the rapid renal clearance of any material entering the bloodstream [135].

To synthesize an exemplary polymeric compound, a controlled polymer synthesis was employed to allow the relationship between polymer structure and function to be assessed, and to also ensure repeatability between synthetic batches. In this regard, Group Transfer Polymerization (GTP), shown schematically in FIG. 1, was utilized to synthesize the backbone polymers. This technique allowed the synthesis of polymers to proceed with controlled molecular weight and polydispersity. In addition, by using GTP, statistical and block copolymers could readily be created by reacting multiple monomer units with either simultaneous or sequential monomer addition.

While GTP allowed the desired control over the molecular architecture of the polymeric compounds, aprotic monomers and anhydrous reaction conditions were also used in the synthesis scheme as GTP is highly susceptible to proton quenching. Further, since it was desired to synthesize polymers with acidic functional groups in some applications, synthesis of the polymer backbone was carried out with protected monomers using standard Schlenk techniques to maintain inert reaction conditions. The desired functionality was then introduced into the polymeric compound by deprotection and subsequent conjugation reactions.

Figure 2:
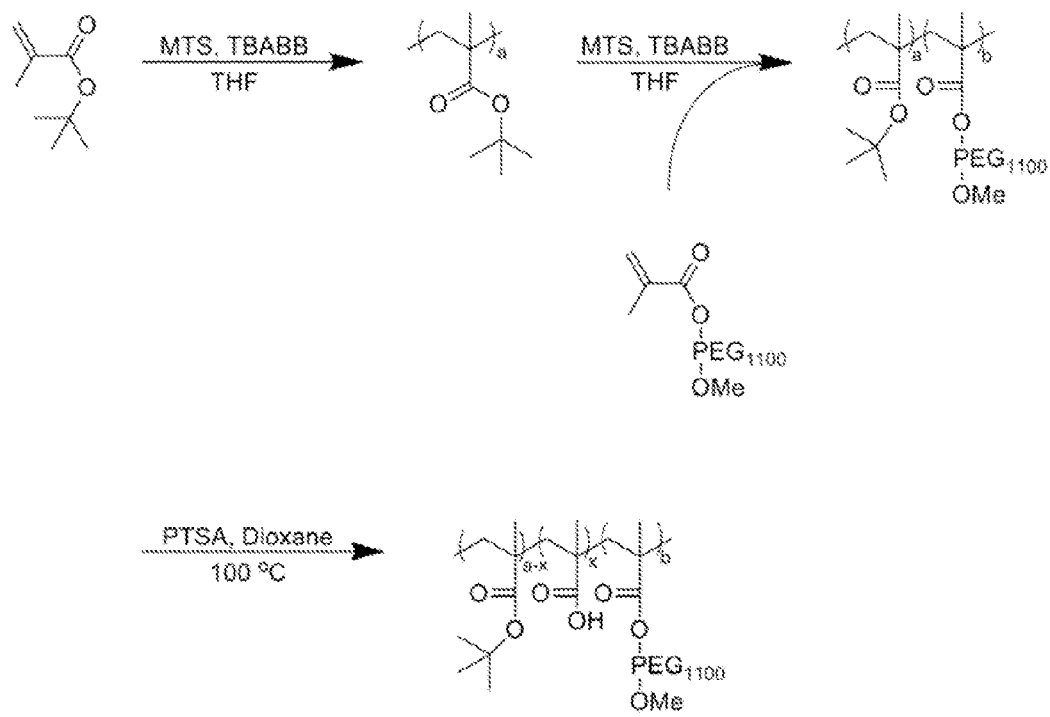
FIG. 2 is a schematic diagram showing a reaction scheme for the synthesis of an exemplary polymeric compound by GTP.

Briefly, using modifications of previous reaction schemes, an exemplary synthesis was carried out as shown in FIG. 2 [141-145]. Solvent was prepared by drying 450 ml of tetrahydrofuran (THF, Mallinckrodt, Hazelwood, Mo.) over a mixture of sodium (4 g, Aldrich, St. Louis, Mo.) and benzophenone (8 g, Aldrich) until the purple color characteristic of the dianion was observed. The proton scavenger bis(dimethylamino) methylsilane (ABCR, Gelest, Morrisville, Pa.) was then distilled under vacuum and stored in a freezer under argon prior to use. Tert-butyl methacrylate (TBMA, Aldrich) and methoxypolyethylene glycol methacrylate ($M_N$=300, MPEGMA$_{300}$, Aldrich), were passed through an inhibitor removal column, distilled, mixed with ABCR (2 wt %), and stored in a freezer under argon prior to use. Methoxypolyethylene glycol methacrylate ($M_N$=1100, MPEGMA$_{1100}$, Aldrich) was dissolved in inhibitor free THF (Aldrich), passed through an inhibitor removal column, and dried under vacuum overnight. This macromer was dissolved in dry, air-free THF to a concentration of 0.4 g/mL, mixed with 2% ABCR, and stored under argon in a freezer prior to use. 1-methoxy-1-(trimethylsiloxy)-2-methyl-1-propene (MTS, Gelest), was vacuum distilled and stored under argon in a freezer prior to use. The catalyst, tetrabutylammonium bibenzoate (TBABB) was prepared, as has previously been described, and stored under nitrogen prior to use [146]. Prior to polymerization, all glassware was dried overnight at 180° C., assembled hot, and flamed under vacuum to remove residual water.

To proceed with the synthesis scheme, approximately 10 mg TBABB was added to a reaction flask under inert atmosphere. Approximately 15 mL of dry, air free THF was also added to the flask by solvent transfer. The initiator, (MTS, 93.3 mg, 0.53 mmol) was then added via syringe under argon and allowed to stir for 15 minutes at room temperature. To form a block copolymer, 1.97 g TBMA (13.9 mmol) was subsequently added to the reaction vessel via syringe under argon and no apparent exotherm was observed. The reaction was then allowed to proceed under argon for 30 minutes, at which time approximately 5 mL was removed for analysis and quenched with methanol. A solution of the second monomer, MPEGMA$_{1100}$, (5 mL, 1.8 mmol) was then added to the reaction vessel and allowed to react for 90 minutes. The reaction was quenched with methanol, the solvent was removed with vacuum, and the product was then dried for 48 hours under vacuum. Based on the stoichiometry, the molecular weights for the TBMA block and the MPEGMA$_{1100}$ block were predicted as 3,700 and 5,900 g/mol, respectively, and the ratio of TBMA blocks to MPEGMA$_{1100}$ was predicted to be 5.1:1.

Figure 4:
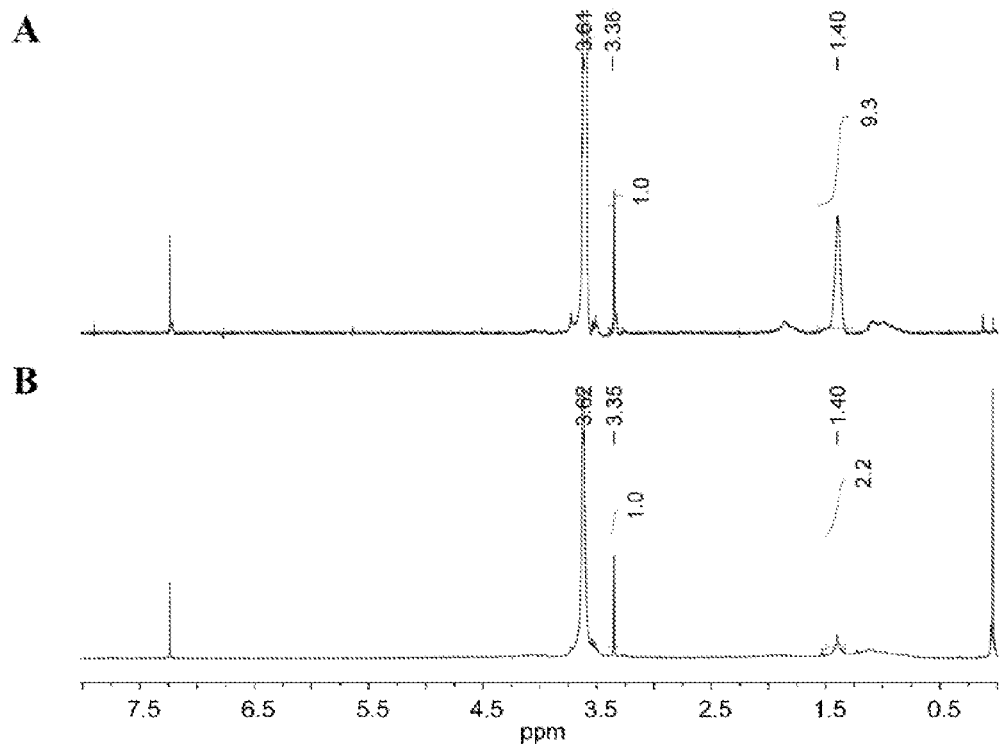
FIGS. 4A and 4B are $^1$H-NMR spectra of an exemplary polymeric compound prior to deprotection of the TBMA groups (FIG. 4A) and after deprotection of the TBMA groups (FIG. 4B).

Block copolymers of MPEGMA$_{300}$ and TBMA were also prepared similarly. Additionally, statistical copolymers were synthesized using the same technique, with simultaneous addition of the two monomers. Finally, a homopolymer of TBMA was also prepared using the same technique. Regardless of the particular polymeric compound being assembled though, subsequent to assembly, the resulting polymers were dissolved in deionized water and were then purified by triplicate ultrafiltrations with Ultracel Amicon YM membranes, with appropriate molecular weight cutoffs, and were isolated by lypholization.

employed [145]. As shown in FIG. 2, hydrolysis was carried out by refluxing in 1,4-dioxane (Aldrich) with p-toluenesulfonic acid (PTSA, Aldrich) for 20-96 hours. The resulting polymers were then purified by ultrafiltration and isolated by lypholization. Analysis of the hydrolysis solution confirmed that no cleavage of the PEG ester bond occurred during deprotection. The degree of TBMA deprotection in the polymer was determined by monitoring the ratio of TBMA (t-butyl ester peak at $\delta$=1.4) to PEGMA (methoxy peak at $\delta$ 3.35) using $^1$H-NMR analysis. As the hydrolysis reaction proceeded from 20 to 96 hours, the extent of hydrolysis increased from 20% to 100%. An example of the NMR spectra of a sample before and after deprotection is shown in FIGS. 4A and 4B, respectively. Using these values, coupled with the molecular weight data obtained from the GPC, the number of TBMA and PEGMA monomers in each assembled polymeric compound were then determined. The results of this analysis are presented in Table 1.

TABLE 1

Summary of Block and Statistical Copolymers used for Analysis of Untargeted Polymers.

| Polymer | Polymer Type | TBMA/ PEGMA | Degree of Deprotection (NMR) | $M_{N,CAL}$ | $M_{N,GPC}^a$ | $PD_{GPC}^a$ |
|---|---|---|---|---|---|---|
| NP | No Polymer | N/A | — | — | — | — |
| EPC | Phospholipid (Egg Phosphatidylcholine) | N/A | — | — | 760 | — |
| PAA | Homopolymer | N/A | — | — | — | <2 |
| PTBMA | Homopolymer | N/A | 0% | 4,240 | 3,960 | 1.28 (0.01) |
| PMAA | Homopolymer | N/A | 100% | 2,570 | 2,400 | 1.28 |
| 0% B | Block Copolymer | 3.1:1 | 0% | 9,320 | 13,200 (384) | 1.13 (0.01) |
| PTBMA-40 | Homopolymer | N/A | 40% | 3,640 | 3,380 | 1.28 |
| 50% B | Block Copolymer | 3.1:1 | 50% | 8,620 | 12,500 | 1.20 (0.04) |
| 80% B | Block Copolymer | 3.1:1 | 80% | 8,250 | 11,700 | 1.29 (0.01) |
| 0% S | Statistical Copolymer | 2.7:1 | 0% | 7,090 | 11,000 (442) | 1.27 (0.05) |
| 80% S | Statistical Copolymer | 2.7:1 | 80% | 6,240 | 10,200 | 1.28 (0.01) |

Figure 3:
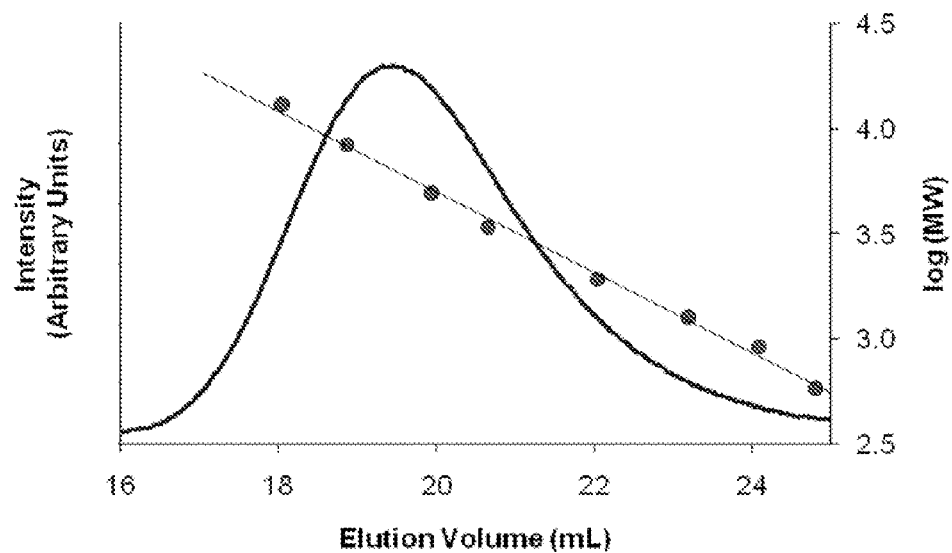
FIG. 3 is a graph showing a sample chromatogram for an exemplary polymeric compound (P2-Pro) prior to deprotection of the t-butylmethacrylate (TBMA) groups and the addition of a basement membrane targeting peptide.

After assembly, the polymers were further characterized by gel permeation chromatography (GPC) and by proton nuclear magnetic resonance spectroscopy ('H-NMR). GPC was carried out using a Shimadzu Prominence High Performance Liquid Chromatography (HPLC) system equipped with a Waters Refractive Index Detector (RID). All analyses were conducted in THF using Waters HR1 and HR2 columns in series with an Agilent PLGel Mixed B column, with a flow rate of 1.0 mL/min, and referenced to narrow molecular weight polystyrene standards (Polymer Laboratories, Shropshire, UK). The molecular weight distribution of the polymers was determined using Shimadzu LabSolutions software. GPC analysis of the protected polymers yielded low polydispersity and good agreement with the results predicted from stoichiometry. A sample GPC chromatogram is shown in FIG. 3. Proton NMR analysis was conducted by dissolving the polymer in deuterated chloroform (Cambridge Isotopes) and measuring the resonance with a Varian Gemini 200 MHz NMR spectrometer. Mestralab Research's MNova software was employed to analyze the NMR spectra.

Figure 5:
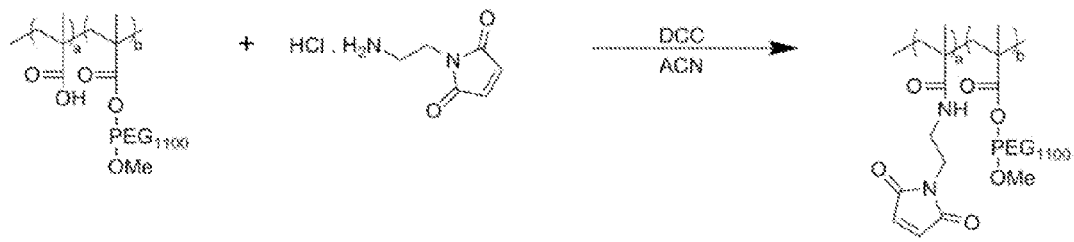
FIG. 5 is a schematic diagram showing a reaction scheme for the conjugation of N-aminoethylmaleimide (NAEM) to a portion of an exemplary polymeric compound subsequent to deprotection of the TBMA groups.

To convert the TBMA groups to methacrylic acid groups, a modification of a previously-described procedure was To introduce additional functional groups into the structure of the deprotected polymers, a bifunctional crosslinker, N-aminoethylmaleimide trifluoric acid (NAEM, Aldrich), was then employed [147,148]. This moiety was covalently attached to the polymer via a stable amide linkage, leaving the maleimide group available for subsequent peptide conjugation. As shown in FIG. 5, the primary amine group of the crosslinker was conjugated to the free acid groups in the polymer chain to form amide bonds using diimide chemistry [149,150]. In this regard, two equivalents of NAEM, based on the number of free acid groups present, were combined with the polymer (1 equivalent of acid groups) and 1.1 equivalent of N,N'-dicyclohexylcarbodiimide (DCC, Aldrich) and dissolved in acetonitrile (ACN, Fisher, Waltham, Mass.). This reaction mixture was stirred at room temperature in the dark for 2 hours. Successful conjugation was indicated by the precipitation of insoluble N,N'-dicyclohexylurea (DCU) precipitate that began to form after approximately 5 minutes of reaction. After reacting for 2 hours, the excess DCC was quenched by adding excess acetic acid (HAc, Fisher) and stirring for 10 minutes. The DCU was then removed by centrifugation, leaving a clear yellow solution.

Figure 6:
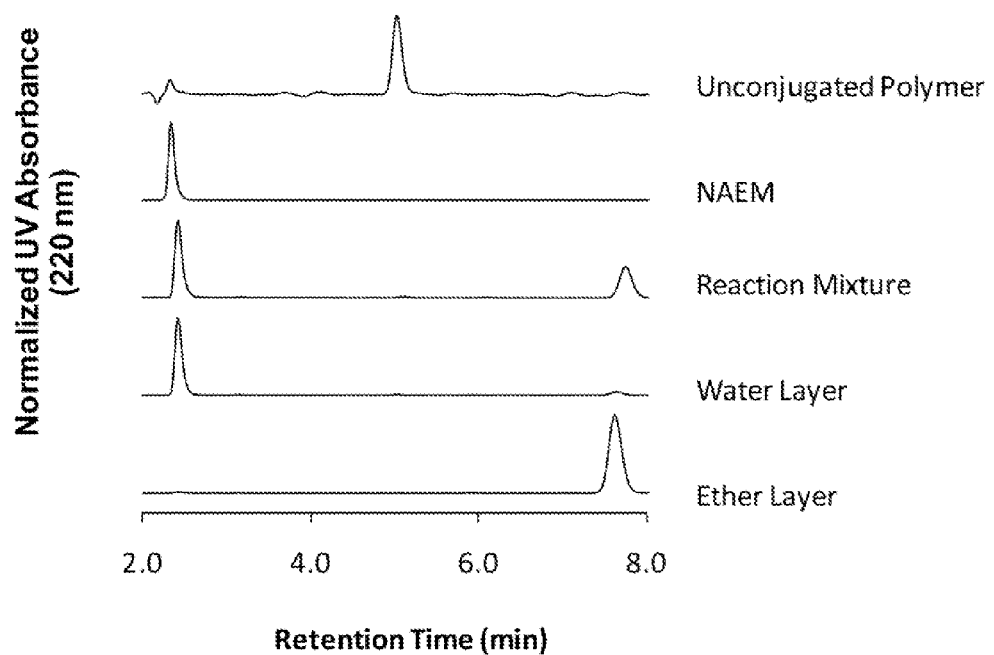
FIG. 6 includes high-performance liquid chromatography (HPLC) chromatograms for an exemplary unconjugated polymeric compound (unconjugated polymer), NAEM, and an exemplary polymeric compound conjugated with NAEM (Reaction Mixture), where a new peak in the chromatogram at 7.7 min confirms the formation of the conjugate.
Figure 7:
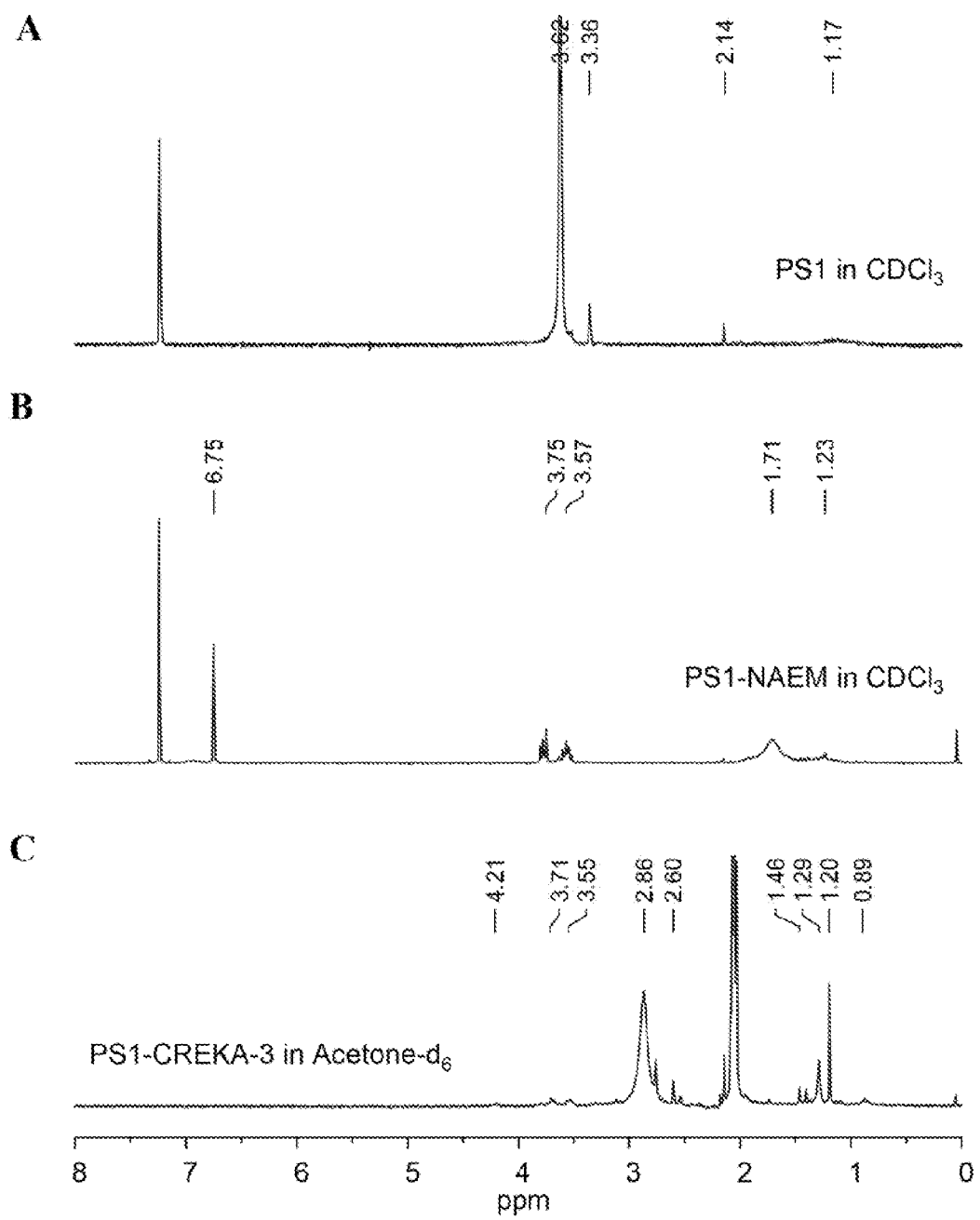
FIGS. 7A-7C are $^1$H-NMR spectra of: an exemplary unconjugated polymeric compound (FIG. 7A) showing the presence of methyl and methylene groups from methacrylic acid units (broad peak at $\delta=1.2$ ppm) as well as ethylene glycol ($\delta=3.5$ ppm) and terminal methoxy peaks ($\delta=3.4$ ppm); the exemplary polymeric compound conjugated with NAEM (FIG. 7B) showing the peaks from the aminoethyl group ($\delta=1.7$ ppm) and the maleimide group ($\delta=6.5$); and the exemplary polymeric compound subsequent to the addition of a fibrin targeting peptide (FIG. 7C, CREKA; SEQ ID NO: 1) showing several peaks corresponding to the pentapeptide ($\delta=1.0-1.5$ ppm, $\delta=2.9$ ppm).

Excess NAEM was removed from the reaction mixture by repeated aqueous extraction from diethyl ether. Upon dissolution in ether, the reaction mixture formed a cloudy liquid, indicating the insolubility of NAEM in the solvent. The clear ether layer that remained after extraction was evaporated. The white solid product was dissolved in acetone, and the solvent was removed by evaporation. HPLC analysis was then conducted on the Shimadzu Prominence HPLC system to confirm the purity of this product. That analysis was carried out with a Restek Viva C18 5 μm 4.6×150 mm HPLC column at a controlled temperature of 40° C. with an isocratic mobile phase consisting of 90% DI water with 0.1% trifluoroacetic acid (TFA, Aldrich) and 10% methanol (Fisher). As shown in FIG. 6, HPLC analysis confirmed that the purification procedure resulted in a pure polymer conjugate. Subsequent NMR analysis, shown in FIGS. 7A-7C, further confirmed the crosslinker incorporation and verified the integrity of the reactive maleimide bond (peak at δ=6.5 ppm). This material was then stored at −20° C. for subsequent peptide conjugation.

For the peptide conjugation procedures, two five-unit oligopeptides were incorporated in the crosslinker-conjugated polymers via a specific reaction between the sulfhydryl group on cysteine and the maleimide group on the crosslinker. Both peptide chains included the amino acids alanine (A), arginine (R), cysteine (C), glutamic acid (E), and lysine (K). The first peptide employed, CREKA (SEQ ID NO: 1; Celtek Biosciences, Nashville, Tenn.), was employed to target the polymers to fibrin, while the second peptide, CAERK (SEQ ID NO: 2; Celtek Biosciences, Nashville, Tenn.), was used as a control.

Figure 8:
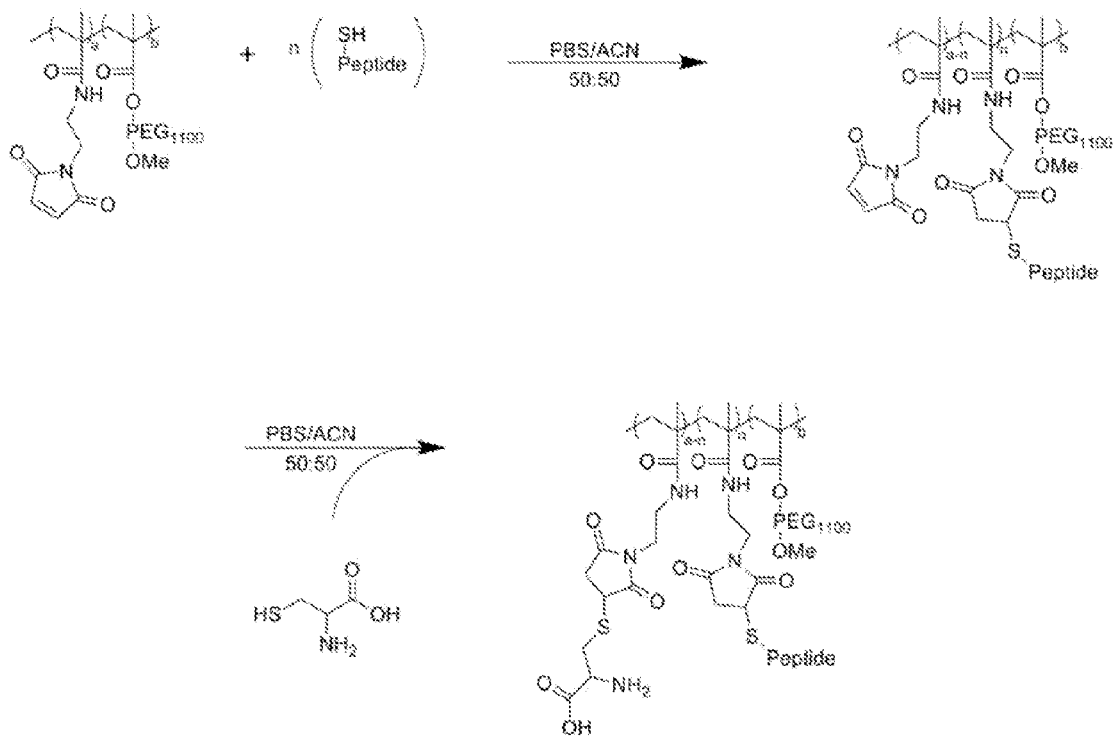
FIG. 8 is a schematic diagram showing a reaction scheme for the conjugation of a peptide to an exemplary NAEM-functionalized polymeric compound.

The peptide conjugation reaction was carried out at room temperature in a solution containing 50% ACN and 50% PBS as shown in FIG. 8. The NAEM-conjugated polymer was dissolved in this solution, and the desired amount of peptide (3-9 peptides per polymer chain) was added to the solution. This reaction mixture was stirred at room temperature in the dark for five hours. Excess cysteine was added to consume unreacted maleimide groups, and the reaction was allowed to proceed for one hour. After removing the solvent in vacuo, approximately 3 mL of acetone was added. Insoluble salts were removed by centrifugation, and the product was then isolated by evaporating the solvent with a stream of dry nitrogen.

Figure 9:
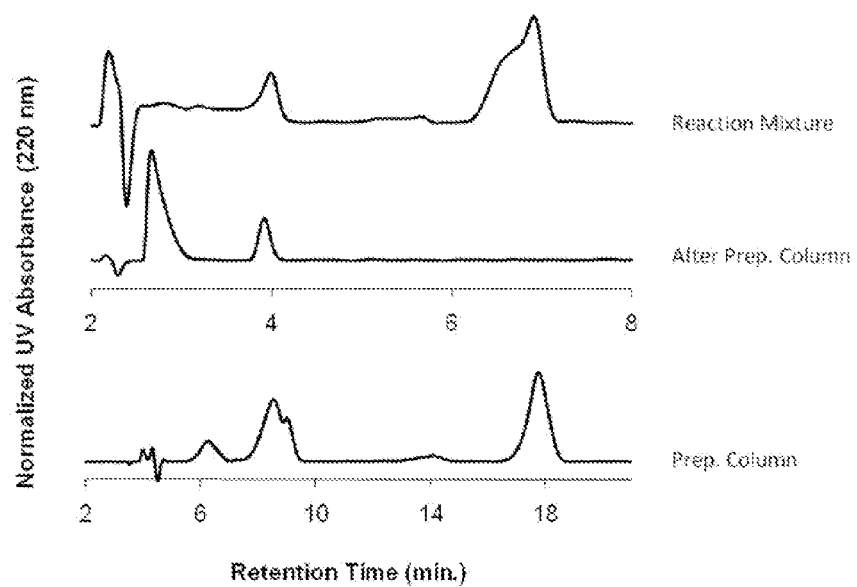
FIG. 9 includes HPLC chromatograms for: an unpurified reaction mixture including exemplary NAEM-functionalized polymeric compounds and oligopeptides (Reaction Mixture); a preparatory HPLC procedure used to isolate the desired polymeric compounds (Prep. Column); and an exemplary purified polymeric compound showing a single peak for the desired product at 3.9 min.

Subsequent to the peptide conjugation procedures, HPLC analysis was then conducted to assess the purity of the reaction mixtures. As shown in FIG. 9, the reaction mixture initially contained several products. As such, preparatory HPLC, using a Shimadzu Prominence HPLC system with a Shimadzu Viva C18 21.2×150 mm column, was then employed to isolate the desired peptide conjugate. The isocratic mobile phase consisted of 90% DI water with 0.1% trifluoroacetic acid (TFA, Aldrich) and 10% methanol (Fisher). The polymer conjugate, which eluted around 7-10 minutes, was isolated by collecting appropriate fractions, and the solvent was removed in vacuo. Subsequent analytical HPLC analysis confirmed the purity of the isolated materials. Again, $^1$H-NMR, shown in FIGS. 7A-7C, supported the proposed polymer-peptide structure.

Figure 10:
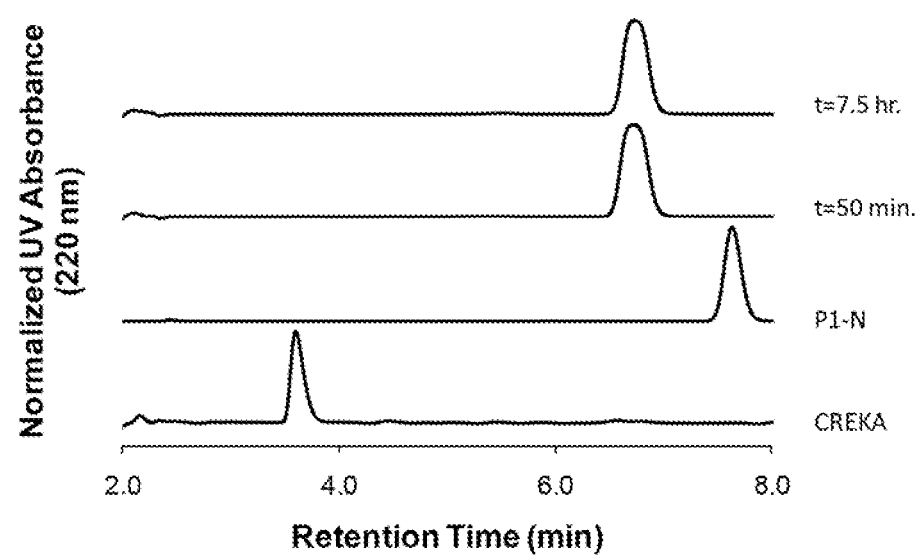
FIG. 10 includes HPLC chromatograms for the starting materials used for the conjugation of a basement membrane targeting peptide to an exemplary NAEM-functionalized compound (CREKA and PS-1, respectively), and for the exemplary peptide-conjugated polymeric compound collected after 50 min of reaction time and after 7.5 hrs of reaction time.

By monitoring the progress of the peptide conjugation with HPLC, it was also possible to confirm that the peptide was quantitatively incorporated into the polymer structure. FIG. 10 shows HPLC chromatograms for the starting materials (CREKA and PS1-N) employed in a particular reaction. As seen in the two chromatograms collected from the reaction at later time points, it was evident that the starting materials were both consumed, and that there was only one product peak. As a result of this rapid, quantitative reaction between the sulfhydryl group on the peptide and the maleimide group on the polymer, it was then possible to determine the composition of the resulting polymer based on the stoichiometry of the reactants. A summary of the resulting polymers are provided in Table 2 below, wherein the column headings are provided with reference to Formula I.

TABLE 2

Polymers used for Evaluation of Targeted Polymer Analysis.

| Polymer Name | $R_2$ Group | r | q | p | $R_1$ (PEG) | q/n | m (kDa) | MW (Da) |
|---|---|---|---|---|---|---|---|---|
| P1-PRO | — | — | 18.4 | 15.9 | 2.5 | 6.5 | 22 | 5,200 |
| P1 | — | — | 18.4 | 15.9 | 2.5 | 6.5 | 22 | 4,300 |
| P1-N | NAEM | — | 18.4 | 15.9 | 2.5 | 6.5 | 22 | 6,200 |
| P1-L | CREKA | 2.3 | 18.4 | 15.9 | 2.5 | 6.5 | 22 | 9,300 |
| P1-H | CREKA | 6.7 | 18.4 | 15.9 | 2.5 | 6.5 | 22 | 14,400 |
| P1-S | CAERK | 2.4 | 18.4 | 15.9 | 2.5 | 6.5 | 22 | 9,300 |
| P2-PRO | — | — | 18.2 | 16.0 | 2.2 | 7.3 | 6 | 3,100 |
| P2 | — | — | 18.2 | 16.0 | 2.2 | 7.3 | 6 | 2,200 |
| P2-N | NAEM | — | 18.2 | 16.0 | 2.2 | 7.3 | 6 | 4,200 |
| P2-L | CREKA | 2.4 | 18.2 | 16.0 | 2.2 | 7.3 | 6 | 7,300 |
| P2-H | CREKA | 7.4 | 18.2 | 16.0 | 2.2 | 7.3 | 6 | 12,800 |
| P2-S | CAERK | 2.4 | 18.2 | 16.0 | 2.2 | 7.3 | 6 | 7,300 |
| P3-PRO | — | — | 30.9 | 26.7 | 4.2 | 6.4 | 22 | 8,700 |
| P3 | — | — | 30.9 | 26.7 | 4.2 | 6.4 | 22 | 7,300 |
| P3-N | NAEM | — | 30.9 | 26.7 | 4.2 | 6.4 | 22 | 10,500 |
| P3-L1 | CREKA | 2.2 | 30.9 | 26.7 | 4.2 | 6.4 | 22 | 14,800 |
| P3-H | CREKA | 6.2 | 30.9 | 26.7 | 4.2 | 6.4 | 22 | 21,000 |
| P3-S | CAERK | 2.2 | 30.9 | 26.7 | 4.2 | 6.4 | 22 | 14,800 |
| P4-PRO | — | — | 22.1 | 17.5 | 4.6 | 3.8 | 6 | 4,300 |
| P4 | — | — | 22.1 | 17.5 | 4.6 | 3.8 | 6 | 3,300 |
| P4-N | NAEM | — | 22.1 | 17.5 | 4.6 | 3.8 | 6 | 5,400 |
| P4-L | CREKA | 2.3 | 22.1 | 17.5 | 4.6 | 3.8 | 6 | 8,700 |
| P4-H | CREKA | 7.1 | 22.1 | 17.5 | 4.6 | 3.8 | 6 | 14,200 |
| P4-S | CAERK | 2.3 | 22.1 | 17.5 | 4.6 | 3.8 | 6 | 8,600 |
| PMAA-PRO | — | — | 18.3 | 18.3 | 0.0 | N/A | 0 | 2,600 |
| PMAA | — | — | 18.3 | 18.3 | 0.0 | N/A | 0 | 1,600 |
| PMAA-N | NAEM | — | 18.3 | 18.3 | 0.0 | N/A | 0 | 3,800 |
| PMAA-L | CREKA | 1.9 | 18.3 | 18.3 | 0.0 | N/A | 0 | 5,800 |
| PMAA-H | CREKA | 5.8 | 18.3 | 18.3 | 0.0 | N/A | 0 | 10,800 |
| PMAA-S | CAERK | 2.0 | 18.3 | 18.3 | 0.0 | N/A | 0 | 7,800 |

Example 2

Evaluation of Surface Adsorption and Protein Resonance Effects

For the initial evaluation of the surface adsorption and protein resistance effects of an exemplary polymeric compound, a model surface consisting of amine-terminated self-assembled mono layers ("SAM") on gold-coated quartz sensor crystals was employed. These SAM surfaces were generated immediately prior to testing using a modification of previously described techniques [155]. Briefly, prior to SAM formation, crystals were cleaned by immersion in an ammonium peroxide solution for 5 minutes at 70° C., rinsed with deionized water, and dried under a stream of inert gas. The crystals were then subjected to ultraviolet ozonolysis (UVO, Bioforce Nanosciences, Ames, Iowa) for thirty minutes to ensure cleanliness. Immediately after UVO treatment, the crystals were then immersed in plastic vials in alkaline 1 mM 11-amino-1-undecanetiol. After purging with argon, vials were sealed and protected from light. After allowing the SAM formation to proceed overnight, the crystals were then removed from the solution, rinsed repeatedly with neutral ethanol and acidic ethanol, and dried with a stream of inert gas.

After constructing the SAMs, the functional properties of the polymeric compounds were then evaluated by monitoring the sequential adsorption of the polymers and bovine serum albumin (BSA) to the model surfaces. In this regard, all of the experiments were conducted in a Quartz Crystal Microbalance (QCM-D, Q-Sense E4) using standard TEFLON® and TYGON® (E. I. Du Pont De Nemours And Company, Wilmington, Del.) tubing materials with a flow rate of 0.250 mL/min. After installing a crystal in the flow module, the sensor crystal was rinsed sequentially with acidic ethanol, neutral ethanol, deionized water, and a pure buffer solution (PBS) to ensure that all unbound aminothiol was removed from the crystal and to establish a flat baseline (less than 0.25 Hz/min drift). The change in frequency and energy dissipation were then able to be measured as a function of time to monitor the adsorption of the polymer from solution (1.0 mg/mL in PBS).

Figure 11:
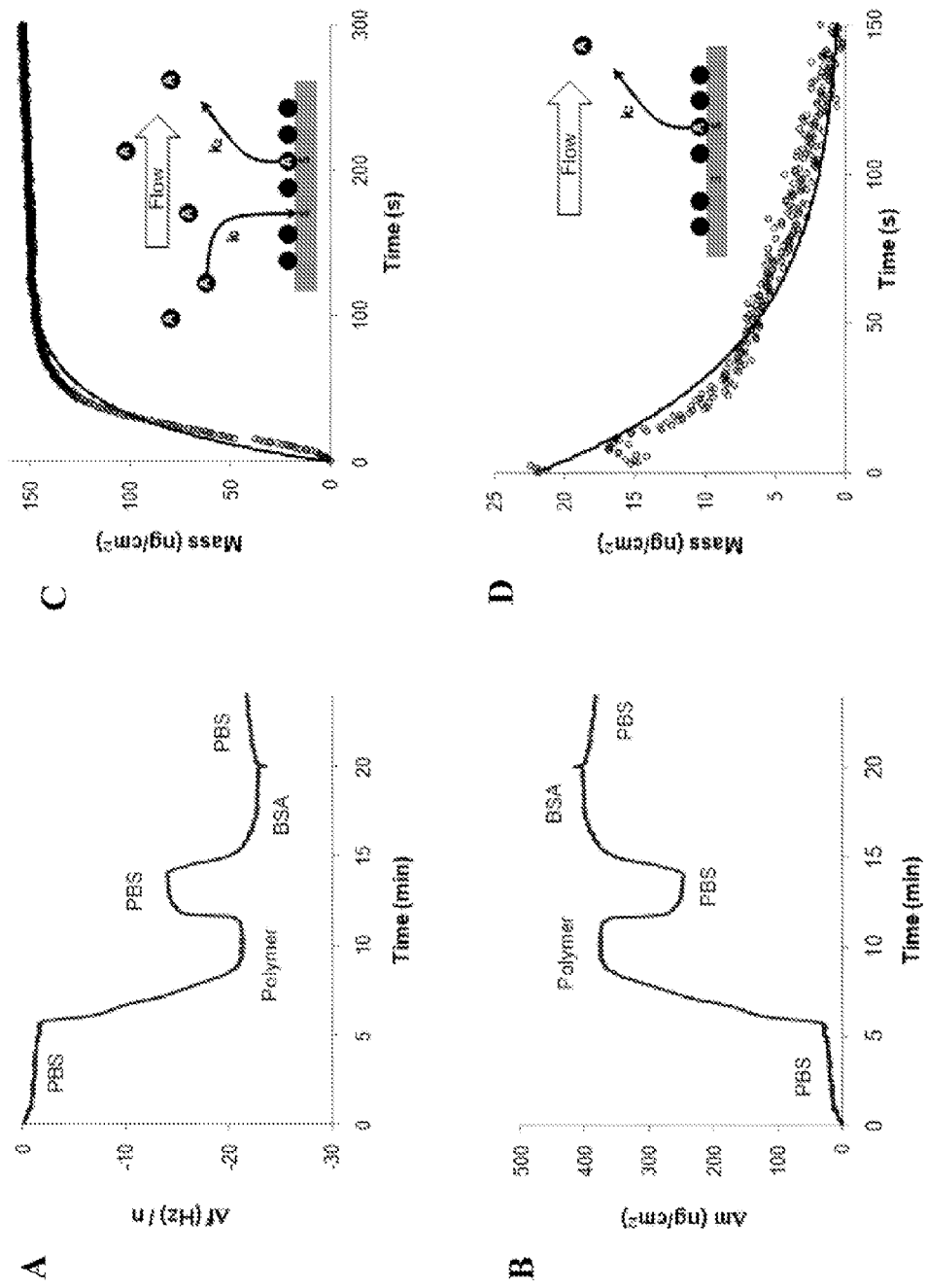
FIGS. 11A-11D are graphs showing representative Quartz Crystal Microbalance (QCM-D) curves for the adsorption of an exemplary polymeric compound (Polymer; TBMA/PEGMA=3.1/1) and bovine serum albumin (BSA) on an amine-terminated self-assembled monolayer (SAM), including: a graph showing the raw data and frequency response ($\Delta f$.

To evaluate barrier assembly and function of the polymeric compounds (e.g., the ability to block protein adsorption), a series of QCM-D based experiments were performed using the amine terminated SAM substrates. A typical experimental curve is presented in FIG. 11A. First, a polymer solution is flowed over the crystal surface, resulting in a decrease in resonance frequency until saturation of the surface is achieved. After this saturation point is obtained, a pure buffer solution is flowed over the crystal to remove the "loosely" bound polymer fraction. To test the barrier function of the adsorbed polymer layer, a solution of BSA is then flowed over the surface until saturation is obtained. Following the saturated binding, a final pure buffer solution is flowed to calculate the amount of BSA strongly adsorbed onto the surface. Using the Sauerbrey model, which neglects viscous effects and assumes that the adsorbed layer is rigid, the mass of adsorbed layer can be calculated (see Equation 1), where C is a constant characteristic of the system (17.7 ng/cm² Hz), and n is the number of the harmonic overtone being considered [157]. Since the change in energy dissipation was small in all measurements (less than $1 \times 10^{-6}$ per 10 Hz frequency change), the Sauerbrey model was assumed to provide an accurate description of the absorbed mass for all analysis. A representative curve of specific mass adsorption is shown in FIG. 11B.

$$\Delta m = -\frac{C \Delta f}{n} \quad (1)$$

A kinetic model of the adsorption and desorption phenomena was further employed to compare the kinetics of the interactions of the materials with model surfaces. Without wishing to be bound by any particular theory, if it was assumed that there were a discrete number of uniform surface sites available for reversible adsorption from solution, it was then possible to visualize the adsorption phenomenon, as shown in FIG. 11C. If it was further assumed that no interaction occurred between adsorbed molecules or between molecules on the surface with molecules in solution, this Langmuir-type adsorption could then be described by Equations 2-6:

$$[SA] = \frac{\alpha}{\beta}(1 - e^{-Bt}) \quad (2)$$

$$[SA]_{max} = \frac{\alpha}{\beta} \quad (3)$$

$$t_{1/2} = \frac{\ln(2)}{\beta} \quad (4)$$

$$a = k_1[A][S]_0 \quad (5)$$

$$\beta = k_1[A] + k_2 \quad (6)$$

In these expressions, [SA] is the concentration of adsorbate on the surface, $[SA]_{max}$ is the maximum concentration observed, $t_{1/2}$, is the half-life of the adsorption process, [A] is the solution concentration of the adsorbate, $[S]_0$ is the total number of surface sites, and $k_1$ and $k_2$ are the kinetic coefficients of adsorption and desorption, respectively. Using a least squares analysis, these equations were fit to the experimental data and $[SA]_{max}$ and $t_{1/2}$ were evaluated for each adsorption event.

Since material is often observed desorbing from the surface after switching back to a buffer solution, this desorption event was also modeled as shown in FIG. 11D. Since [A] was equal to zero in this case, this desorption phenomenon was then described by Equations 7-8:

$$[SA] = [SA]_{loose}(e_2^{-kt}) \quad (7)$$

$$t_{1/2} = \frac{\ln(2)}{k_2} \quad (8)$$

The amount of material strongly bound to the surface, $[SA]_{bound}$, is taken as the difference in the amount initially adsorbed and $[SA]_{loose}$, the amount observed desorbing.

Figure 12:
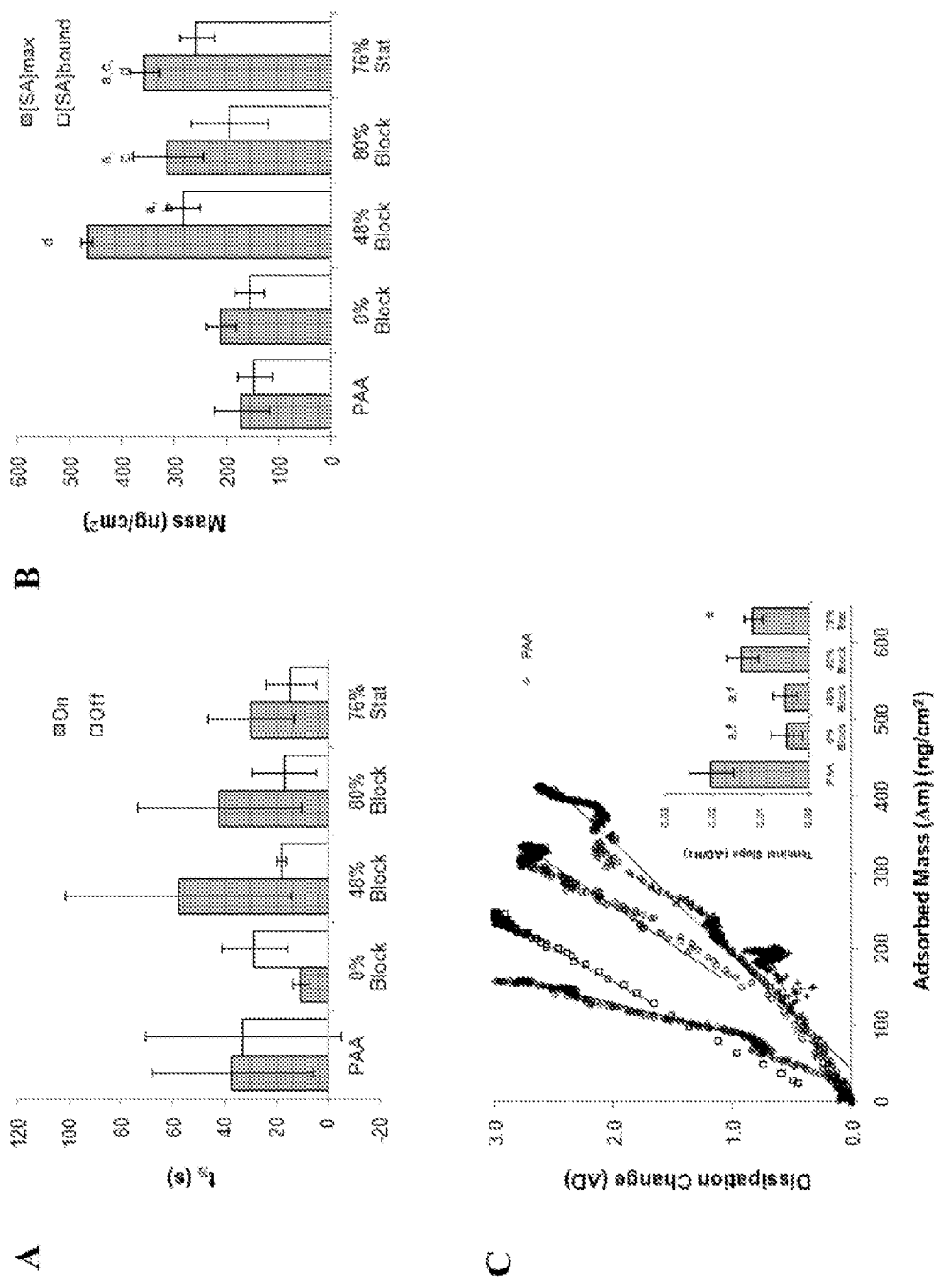
FIGS. 12A-12C are graphs showing the adsorption of various exemplary polymeric compounds, including: a graph showing the half-life for polymeric compound adsorption (grey bars) and desorption (white bars) from solution onto a SAM substrate (FIG. 12A); a graph showing the maximum specific mass adsorption, $[SA]_{max}$, and specific mass of tightly bound polymeric compounds, $[SA]_{bound}$ (FIG. 12B); and a graph showing the dissipation change as a function of adsorbed mass for polymeric compound adsorption phenomena (FIG. 12C), where the slope of the curve represents the relative rigidity of the adsorbed layer, with a steeper slope indicating a less rigid adsorbed layer. Statistical comparisons are further given: 95% confidence compared to polyacrylic acid (PAA) (a), 95% confidence compared to 0% Block (b), 95% confidence compared to 48% Block (c), 90% confidence compared to 48% Block (d), 90% confidence compared to PAA (e), and 90% confidence compared to 80% Block (f).

Based upon analysis of on and off rates of polymer adsorption (FIG. 12A), there was no statistical difference between the different polymeric compounds tested. Only the 0% polymer sample possessed an on rate half-life that was faster than the off rate, agreeing with the expected difference in binding mechanism (hydrophobic vs. charge interactions). As polymer charge density increased from 0% to 80%, polymer adsorption to the charged surface varied from 211-468 ng/cm². A statistically significant maximum in $[SA]_{max}$ was found at a charge density of 48%. As PBS was flowed over the surface and polymer desorption occurred, sample differences between all charged diblock polymers were attenuated. PAA and 0% PEG-PMA possessed the lowest degree of surface coverage as shown in FIG. 12B.

There was also a noticeable difference in the mechanism of binding. FIG. 12C shows plots of the energy dissipation change (AD) versus the mass adsorbed. The terminal slope of these curves, defined as the slope measured after 50% of $[SA]_{max}$ was achieved, increased with charge density. As such, the slope of these curves provided a means to evaluate the conformation of the polymer adsorbed to the surface. A lower slope indicated a relatively small change in energy dissipation with adsorption, while a steeper slope indicated higher increasing energy losses with mass adsorption. In this regard, a low slope was interpreted as indicating a relatively rigid, compact adsorbed layer, while a steeper slope indicated an adsorbed layer that extended further away from the surface.

Unlike polymer adsorption, there was a change in kinetics of protein binding among samples. The half-life of protein adsorption was lowest for the uncoated surfaces, indicating the greatest affinity of BSA, while the PAA control possessed the slowest binding and release rates of all materials tested. There was no statistical difference in the kinetics of the protein adsorption for diblock copolymer coated surfaces. The uncoated charge surface possessed the greatest degree of protein binding. Of all test samples, 0% PEG-PMA possessed the best blocking ability of all tested polymers. It also appeared that the 76% statistical copolymer sample possessed equivalent surface blocking capacity.

Figure 13:
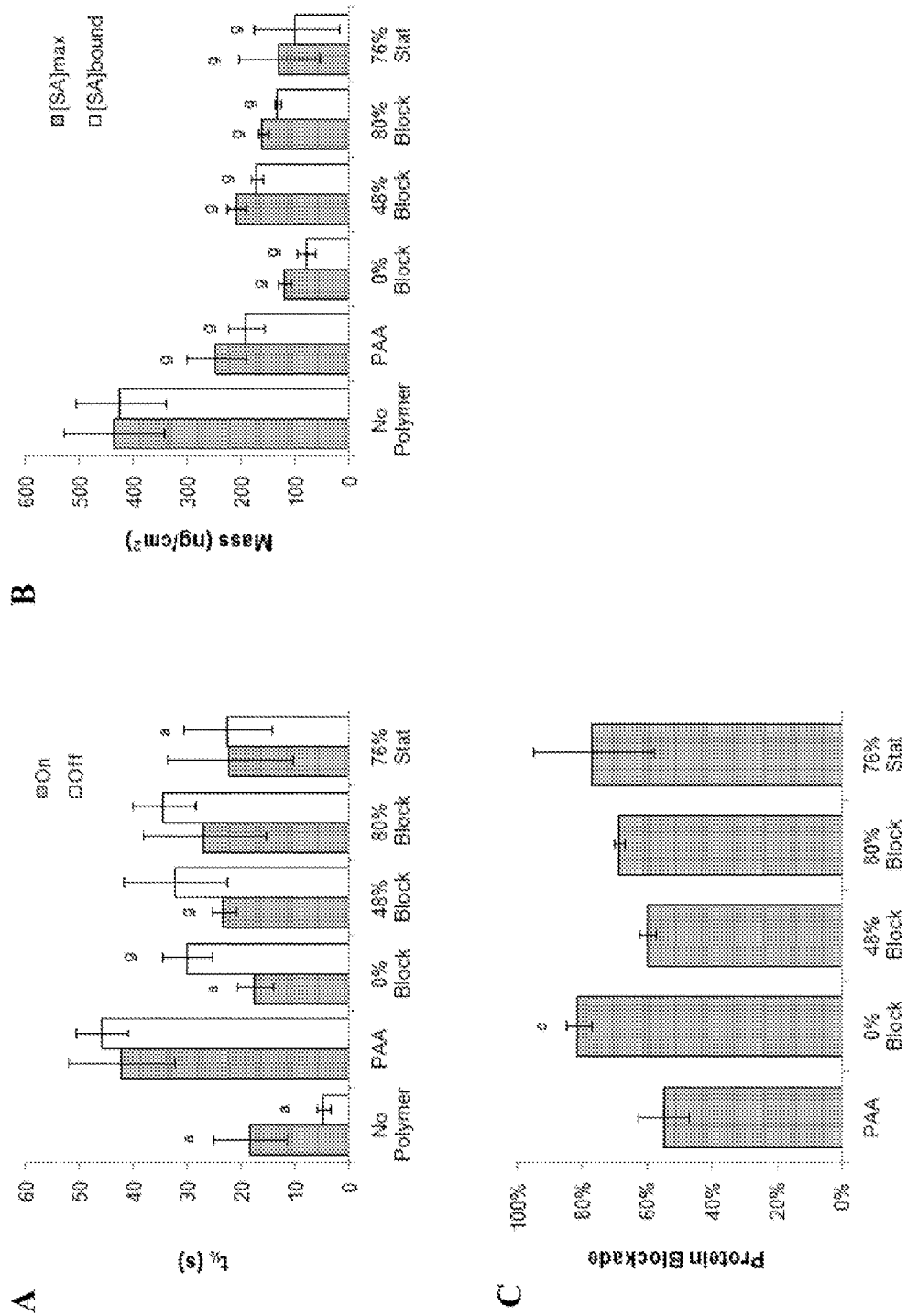
FIGS. 13A-C are graphs showing BSA adsorption from solution by itself or in the presence of various exemplary polymeric compounds, including: a graph showing the half-life for polymeric compound adsorption from solution onto SAM substrates (FIG. 13A); a graph showing the maximum specific mass adsorption, $[SA]_{max}$, and specific mass of tightly bound polymeric compounds, $[SA]_{bound}$ (FIG. 13B); and a graph showing the percent protein blockade compared to control (PAA). Statistical comparisons are further given: 95% confidence compared to PAA (a), 90% confidence compared to PAA (e), and 95% confidence compared to No Polymer (g).

As can be seen in FIGS. 13A-C, BSA adsorbs to the model substrate with maximum specific adsorption of 416.9±100.2 ng/cm$^2$. Assuming a molecular weight of 67 kDa and a molecular topology that can be calculated as an equilateral triangular prism with sides of 8 nm and thickness of 3 nm, a monolayer of BSA adsorbed to the surface would yield a specific adsorption of 402 ng/cm$^2$. Since this value was close to the observed BSA adsorption, it was thus inferred that BSA formed a strong monolayer coating on the model substrate. Specific and non-specific protein adsorption interactions are an integral precursor in the formation of a post surgical adhesion. It is believed, therefore, that the ability to block this event serves as a simple measure of a material's ability to interrupt post-surgical adhesion (PSA) formation.

Example 3

Conjugation of Basement Membrane Targeting Peptides and Functional Capacity of Peptide Conjugated Polymers To test the functional capacity of the polymeric compounds that included the fibrin targeting peptide CREKA (SEQ ID NO: 1), a fibrin targeting study was performed using QCM (Q-Sense) where a gold QCM crystal surface was coated with fibrinogen followed by thrombin activation to form fibrin. Briefly, a solution of fibrinogen (2 mg/mL in TRIS buffer) was first flowed across the crystal for 10 minutes. After rinsing with TRIS buffer, the adsorbed fibrinogen was activated by incubating with a solution of thrombin (5.5 U/mL) for 30 minutes to form crosslinked fibrin on the surface. These crystals were then removed and the entire QCM flow system was cleaned with acidic ethanol to remove residual proteins. After reinstalling the fibrin coated crystals in the QCM, a stable baseline was obtained in PBS solution. The polymer solution (0.1 and 1.0 mg/mL) was flowed through the system for 10 minutes, followed by a solution of PBS. Solutions (1 mg/ml) of PEG-PMA possessing 0 (▲), 3 (♦) or 9 (●) CREKA units per polymer chain were flowed over the QCM crystal at 37° C. and the mass absorbed was measured by monitoring the decrease in resonant frequency. As seen in the kinetic plot of FIG. 14, the rate and amount of binding to fibrin increased as the CREKA content increased.

Figure 14:
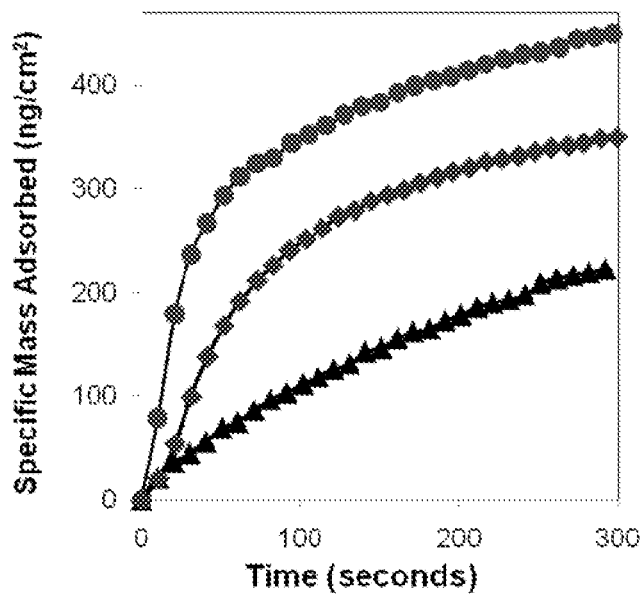
FIG. 14 is a graph showing the ability of exemplary polymeric compounds including 0 (▲), 3 (♦) or 9 (●) CREKA peptides (SEQ ID NO: 1) per polymeric compound to bind to a fibrin-coated surface.
Figure 15:
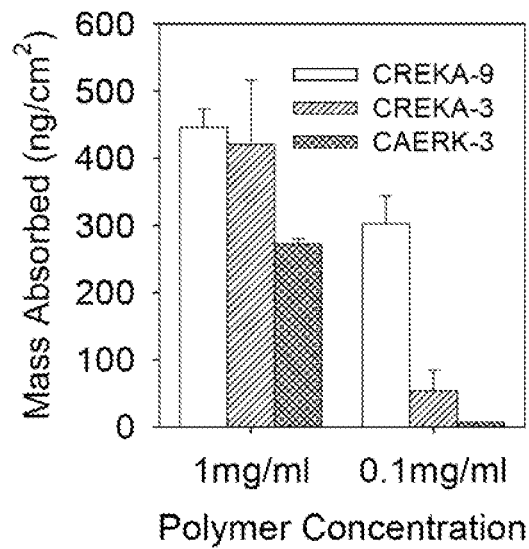
FIG. 15 is a graph showing the concentration-dependant binding of an exemplary polymeric compound to a fibrin-coated surface, where the compounds included either three CREKA fibrin targeting peptides per compound (CREKA-3), nine CREKA peptides per compound (CREKA-9), or three scrambled, CAERK, peptides per polymer (CAERK-3).

As also shown in FIG. 14, while the base polymer was able to bind to the fibrin surface, the coupling of CREKA to the polymer resulted in a substantial increase in bound polymer. Based upon a comparison with a similar experiment using a peptide scramble (CAERK; SEQ ID NO: 2) along side the polymers conjugated with CREKA (FIG. 15), it can be seen that the binding of the polymers is specific for the CREKA residue and not simply a result of the change in polymer charge. Further, CREKA-9 binding was not as sensitive to concentration, indicating that the expected benefit of target group multimerization is observed for the polymers.

Example 4

Disruption of Fibrin Gel Matrix Formation by Targeted Polymers

The fibrin gel matrix (FGM) is a component in the formation of post-surgical adhesions (PSAs). Consisting of fibrin and a mixture of extracellular matrix components, the FGM can bridge apposing tissues in the body and lead to the formation of PSAs. As such, the polymeric compounds of the presently-disclosed subject matter, despite their ability to adsorb to charged surfaces and block non-specific protein adsorption, were further analyzed to determine whether the polymeric compounds were capable of interrupting the formation of a FGM and thus disrupting the cascade of events that leads to PSA formation.

Without wishing to be bound by any particular theory, it was hypothesized that the molecular structure of the polymeric compounds could be tailored to optimize the adsorption of the polymers to pro-adhesive sites on the surface of damaged tissue and thus attenuate the formation of PSAs. In order to test this hypothesis, block copolymers were synthesized with controlled molecular architectures and three characteristics of their molecular architectures were systematically varied to allow their resulting performance to be analyzed in vitro. Since PEG was incorporated into the polymer structure for its anti-adhesive properties, the PEG structure in the polymers were first varied. In this regard, two PEGMA monomers with different PEG chains lengths ($M_N$=300 and $M_N$=1,100) were selected to investigate the effect of this property in disrupting fibrin gel matrix formation. Secondly, the number of PEG chains in the polymer was also varied to determine the impact of total PEG content. Thirdly, the effect of targeting peptides in the polymer structure was also determined by varying both the nature and the number of the targeting peptides in each polymeric compound.

Several techniques were employed to investigate the polymeric compounds' ability to function as desired. Quartz Crystal Microbalance with Dissipation (QCM-D) was used to study the kinetics and blockade of fibrinogen adsorption. The ability of the polymeric compounds to retard the propagation of the FGM was studied using a turbidity assay, which assessed the kinetics of FGM formation from a fibrin-coated surface. Further, the attachment of cells to polymer-treated fibrin gels was also determined and quantified using a fluorescent DNA assay to mimic the action of macrophages during the rearrangement and strengthening phase of PSA formation.

After completion of the experiments, for comparisons between the various compounds, statistical relevance was then determined by performing analysis of variance followed by a Sidak pair wise post-hoc analysis using Minitab 15. Each figure was analyzed separately. Differences at greater than 95% and 99% confidence were noted, with statistical significance being considered at the 95% level. Unless otherwise stated, all values were reported as mean±standard error.

In order to understand the impact of the molecular architecture on the various performance parameters evaluated, an additional statistical analysis was also conducted for each experiment. This modeling included the 16 block copolymers described in Table 3 below, wherein the column headings are provided with reference to Formula I.

TABLE 3

Polymers Included in General Linear Model for Targeted Polymer Analysis.

| Polymer Name | $R_2$ Group | r | q | p | $R_1$ (PEG) | n | m (kDa) | MW |
|---|---|---|---|---|---|---|---|---|
| P1 | — | — | 18.4 | 15.9 | 2.5 | 6.5 | 22 | 4,300 |
| P1-L | CREKA | 2.3 | 18.4 | 15.9 | 2.5 | 6.5 | 22 | 9,300 |
| P1-H | CREKA | 6.7 | 18.4 | 15.9 | 2.5 | 6.5 | 22 | 14,400 |

TABLE 3-continued

Polymers Included in General Linear Model for Targeted Polymer Analysis.

| Polymer Name | R$_2$ Group | r | q | p | R$_1$ (PEG) | n | m (kDa) | MW |
|---|---|---|---|---|---|---|---|---|
| P1-S | CAERK | 2.4 | 18.4 | 15.9 | 2.5 | 6.5 | 22 | 9,300 |
| P2 | — | — | 18.2 | 16.0 | 2.2 | 7.3 | 22 | 2,200 |
| P2-L | CREKA | 2.4 | 18.2 | 16.0 | 2.2 | 7.3 | 22 | 7,300 |
| P2-H | CREKA | 7.4 | 18.2 | 16.0 | 2.2 | 7.3 | 6 | 12,800 |
| P2-S | CAERK | 2.4 | 18.2 | 16.0 | 2.2 | 7.3 | 6 | 7,300 |
| P3 | — | — | 30.9 | 26.7 | 4.2 | 6.4 | 6 | 7,300 |
| P3-L1 | CREKA | 2.2 | 30.9 | 26.7 | 4.2 | 6.4 | 6 | 14,800 |
| P3-H | CREKA | 6.2 | 30.9 | 26.7 | 4.2 | 6.4 | 6 | 21,000 |
| P3-S | CAERK | 2.2 | 30.9 | 26.7 | 4.2 | 6.4 | 6 | 14,800 |
| P4 | — | — | 22.1 | 17.5 | 4.6 | 3.8 | 22 | 3,300 |
| P4-L | CREKA | 2.3 | 22.1 | 17.5 | 4.6 | 3.8 | 22 | 8,700 |
| P4-H | CREKA | 7.1 | 22.1 | 17.5 | 4.6 | 3.8 | 22 | 14,200 |
| P4-S | CAERK | 2.3 | 22.1 | 17.5 | 4.6 | 3.8 | 22 | 8,600 |

The responses from the QCM analysis, turbidity assay, and cellular attachment study, were included in the additional statistical analysis. For each response, ANOVA was carried out by fitting a general linear model using the variables of PEG chain length, number of PEG units, number of monomer units in the polymer backbone, peptide type, and number of peptide units per polymer molecule. Additionally, for each model, residual plots, including a normal probability plot, a frequency plot, and standardized residual plots were generated. These plots were used to verify the validity of the assumptions made in the general linear model. If the residuals were normally distributed, the normal probability plot was expected to show a linear trend with minor deviations in the tails. In addition, the frequency plot should be symmetrical with approximately 95% of the values within the range of ±2. Finally, no apparent bias should be observed in the standardized residual plots [177-179]. In cases where apparent deviations from normality were observed, the analysis was repeated after removal of outliers to ensure that the trends predicted by model were unaffected. Main effects plots were then generated for each model in order to understand the impact of each factor. No outliers were removed from the analysis.

In each of the experiments indicated above for testing the polymeric compounds' ability to function as desired, a total of 20 polymers, as synthesized in Example 1, were typically employed. As shown in Table 2, these polymer architectures included two levels each for the PEG chain length ($M_N$=300 and $M_N$=1,100) and the backbone chain length (approximately 24 and approximately 42 monomer units). In addition, the impact of peptide type (fibrin specific CREKA (SEQ ID NO: 1) versus CAERK (SEQ ID NO: 2) scramble) was investigated. The number of fibrin specific CREKA units per polymer molecule was also varied. Control polymers without PEG were additionally included in each analysis, and, finally, free peptide (both CREKA and CAERK), as well as a commercially available phospholipid (egg phosphatidycholine, EPC) were employed as additional controls.

For the experiments, polystyrene (PS) solution was prepared by dissolving polystyrene ($M_N$=280,000, Fisher, 0.5 wt. %) in toluene (Fisher). Fibrinogen solutions (13.2 mg/ml, 0.50 mg/mL, and 0.10 mg/mL) were prepared in Tris-Buffered Saline (TBS, Aldrich). Bovine Serum Albumin (BSA, Fisher, 1.0 mg/mL) solution was prepared in TBS. Thrombin solution was prepared by diluting a stock thrombin solution (5 U/mL) to the desired concentrations in TBS (2.5 U/mL and 0.1 mU/mL). Fresh protein solutions were prepared prior to analysis each day, and polymer solutions were prepared by dissolving purified polymer in TBS to the desired final concentration and were stored at −20° C. prior to use.

Figure 16:
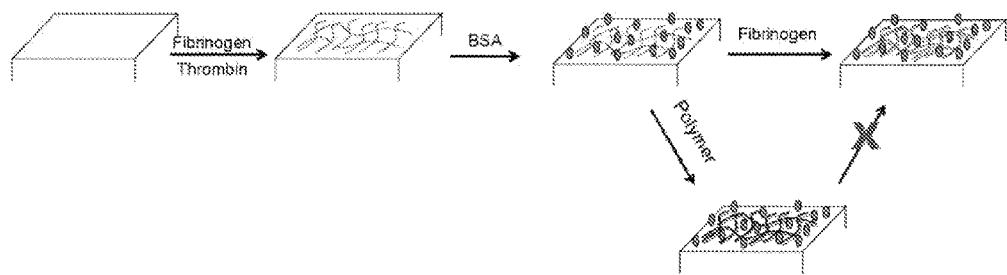
FIG. 16 is a schematic representation of a proposed fibrin blockade mechanism in a QCM analysis employing an exemplary polymeric compound (Polymer).

Using a modification of a previously developed method, quartz crystal microbalance was first used to monitor the ability of targeted polymers to adsorb to fibrin coated samples and to block subsequent fibrinogen adsorption [152]. Shown schematically in FIG. 16, this QCM analysis was carried out in a series of steps. First, polystyrene coated quartz crystals were prepared for use as a model substrate. A layer of fibrinogen was then allowed to adsorb to these crystals and was subsequently activated with thrombin to form a fibrin coated surface. After blocking nonspecific adsorption with BSA, the material under investigation was then allowed to coat the surface. Finally, a second fibrinogen adsorption step was carried out and the ability of the materials to suppress this fibrinogen binding was evaluated.

In these steps, gold coated AT cut quartz crystals with a fundamental frequency of 5 MHz obtained from Q-Sense were used as model substrates. These crystals were spin coated with polystyrene (PS) to create a uniform hydrophobic surface for fibrin adsorption using modifications of a previously described procedure [173]. Prior to coating with polystyrene, the crystals were cleaned by soaking in toluene for a minimum of two hours and dried in a stream of inert gas. They were subsequently spin coated with a PS solution at 2,500 RPM for 60 seconds using a CEE® 100 spin coater manufactured by Brewer Scientific (St. Louis, Mo.) and dried at 100° C. in a vacuum oven overnight. Subsequently, the thickness of the PS layer was measured using variable angle spectroscopic ellipsometry. Five samples were analyzed and the PS layer was determined to be 57.1±8.4 nm. In order to assure the repeatability of this surface preparation procedure, control experiments with no barrier material were conducted at various time points and no significant differences were observed in the rate or level of fibrinogen deposition.

Subsequent to the fabrication of the substrates, QCM-D experiments were then conducted in a Q-Sense E4 at 37° C. with a flow rate of 50 μL/min to determine the kinetics and blockade of fibrinogen adsorption to the substrates. Resonant frequency shift (Δf) and energy dissipation (D) values were collected for the fundamental frequency and for odd overtones (n=1, 3, 5, 7, 9, 11, and 13) using the low noise setting for the duration of the experiments. Briefly, in these experiments, after installing four crystals in parallel and verifying their quality (D<30 ppm in air), TBS was flowed through the system until a stable baseline was obtained. An experiment was then started with TBS flowing and, after 5 minutes, a solution of fibrinogen (0.1 mg/mL) was introduced into the system. After exposing the crystals to fibrinogen for 15 minutes, the system was rinsed with TBS for 5 minutes. Thrombin (0.1 U/mL) was then flowed over the crystals for 10 minutes, followed by an additional 5 minute rinse with TBS. BSA (1.0 mg/mL) was allowed to interact with the surfaces for 10 minutes. After rinsing again with buffer, a solution containing the polymeric compound of interest (0.10 mg/mL in TBS) was then introduced and allowed to flow through the system for 5 minutes. Unbound material was washed away with TBS for 5 minutes. A solution of fibrinogen (0.10 mg/mL in TBS) was then introduced and flowed through the system for 25 minutes. Finally, the QCM was rinsed with of TBS for 20 minutes to facilitate the removal of unbound fibrinogen. As a control, the same procedure was followed without the addition of polymer solution or the subsequent buffer rinse. Each polymeric compound was evaluated in a minimum of three experiments.

Figure 17:
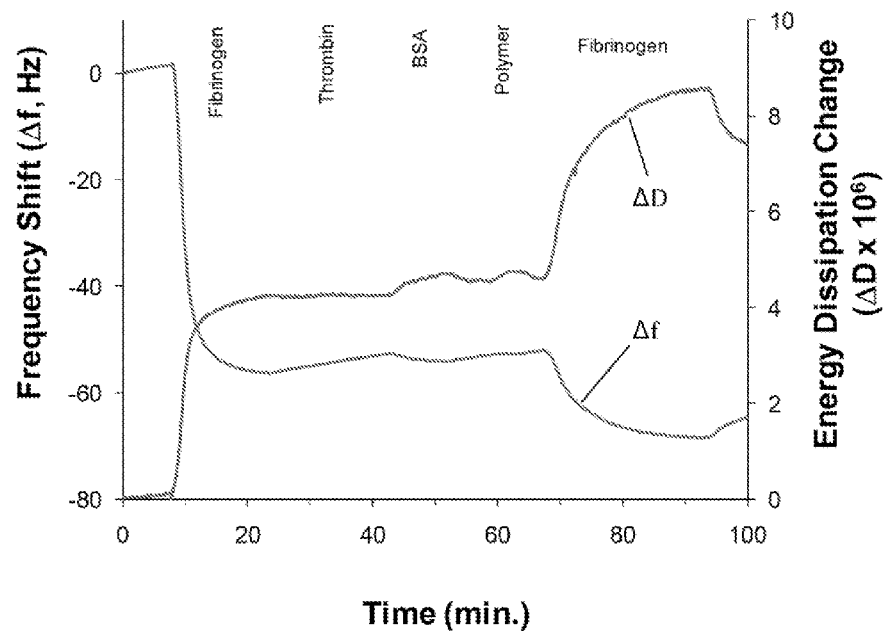
FIG. 17 is a graph showing a representative QCM sensorgram depicting the frequency shift (Δf) and energy dissipation (ΔD) observed on quartz crystals after sequential adsorption of fibrinogen, thrombin, BSA, an exemplary polymeric compound (Polymer), and fibrinogen to the crystals, where Tris-buffered saline (TBS) washes between each adsorption event are indicated by the shaded regions.

Upon analysis of the results from the QCM-D experiments, it was found that the energy dissipation observed with the fibrinogen coated samples was much higher that was seen in previous experiments (FIG. 17). As a result, the approximations employed in the Sauerbrey model were not valid for this set of experiments, and the mass adsorbed on the surface could not be accurately determined. Rather, the raw frequency response data was employed to extract pseudo-first order parameters for the maximum fibrinogen adsorption and the kinetic rate constant for the two fibrinogen adsorption events. Additionally, this highly decoupled water-rich surface layer was thought to be responsible for the inability to discern the adsorption of the barrier materials to the surface.

To assess the ability of the materials to inhibit the adsorption of fibrinogen to a surface bound fibrin layer, two kinetic parameters were further determined. First, the maximum fibrinogen adsorption observed in the second fibrinogen adsorption step was determined using a least squares analysis. Since the first fibrinogen adsorption step was somewhat variable, possible due to degradation of the frequency response characteristics of the quartz crystals with repeated use, the second level of the second fibrinogen adsorption was normalized to the first fibrinogen response and this ratio ($Fg_2/Fg_1$) was reported. In addition, the pseudo-first order kinetic half-life ($t_{1/2,Fib}$) of the second fibrinogen adsorption step was determined using a least squares analysis.

Figure 18:
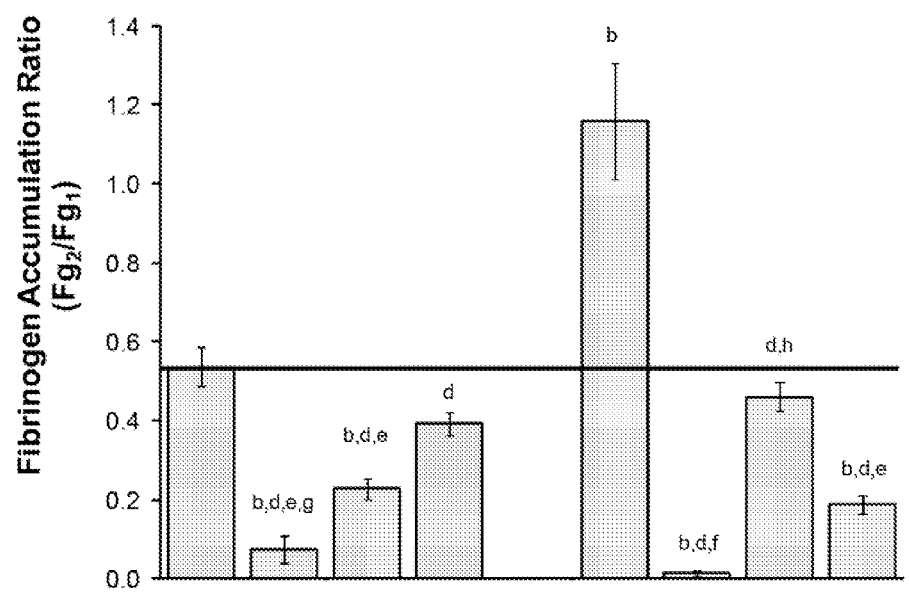
FIG. 18 is a graph showing the fibrinogen adsorption ratio for various exemplary polymeric compounds (PMAA polymers) to fibrin-coated quartz crystal, where: the values presented represent the mass ratio seen in final and initial fibrinogen adsorption steps; the horizontal bar represents the ratio observed for the control samples with no polymeric compound treatment; and statistically significant differences (p≥0.95) are reported: b (99% compared to no polymeric compound), d (99% compared to PMAA), e (95% compared to PMAA-H), f (99% compared to PMAA-H), g (95% compared to Egg Phosphatidylcho line (EPC)), and h (99% compared to EPC).
Figure 19:
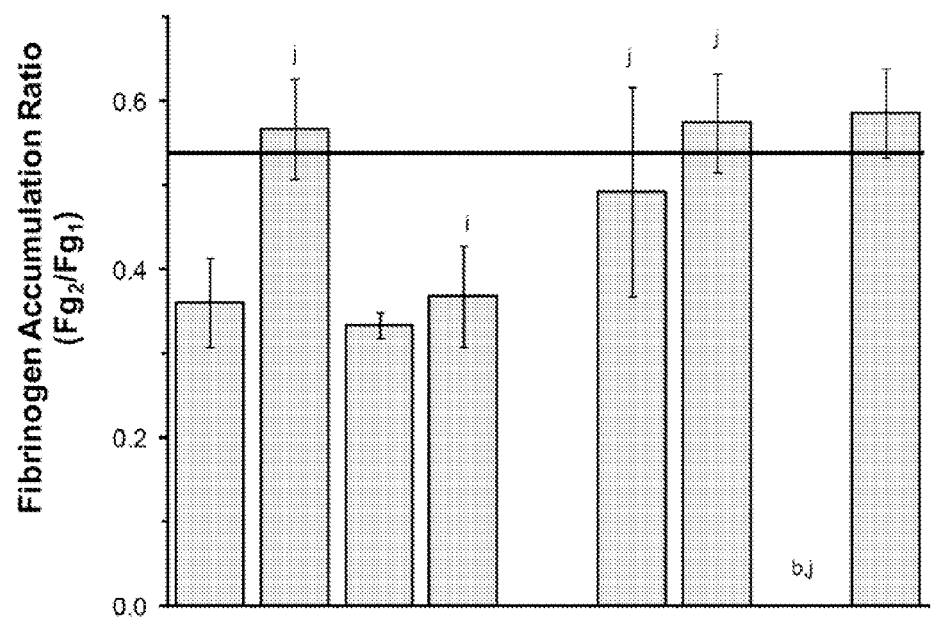
FIG. 19 is a graph showing the fibrinogen adsorption ratio for various exemplary polymeric compounds (long ($M_N$=1,100) PEG chain polymers) to fibrin-coated quartz crystal, where: the values presented represent the mass ratio seen in final and initial fibrinogen adsorption steps; the horizontal bar represents the ratio observed for the control samples with no polymeric compound treatment; and statistically significant differences (p≥0.95) are reported: b (99% compared to no polymeric compound), i (95% compared to P3-H), and j (99% compared to P3-H).
Figure 20:
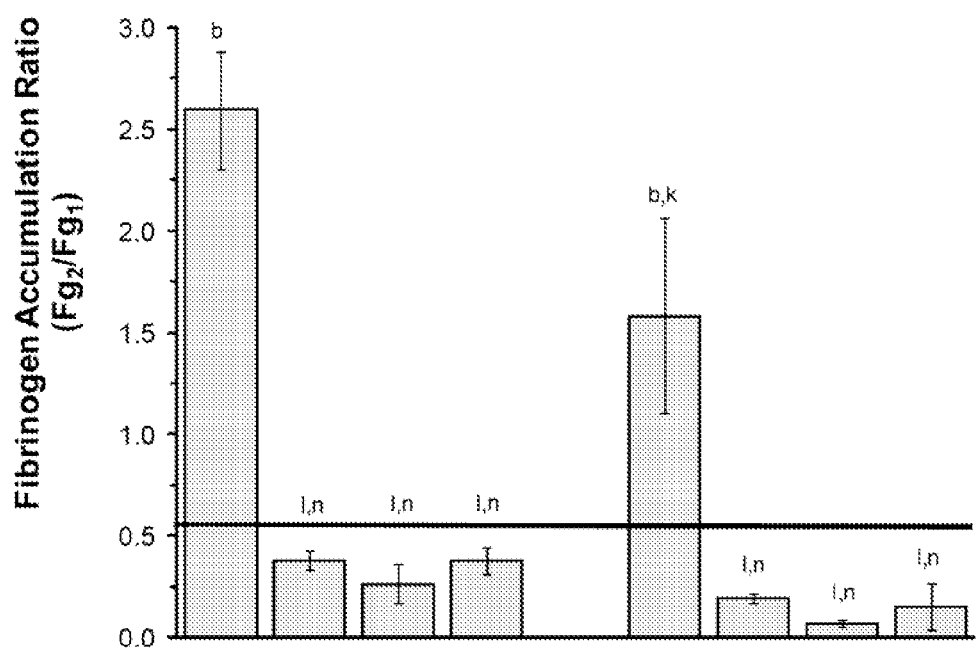
FIG. 20 is a graph showing the fibrinogen adsorption ratio for various exemplary polymeric compounds (short ($M_N$=300) PEG chain polymers) to fibrin-coated quartz crystal, where: the values presented represent the mass ratio seen in final and initial fibrinogen adsorption steps; the horizontal bar represents the ratio observed for the control samples with no polymeric compound treatment; and where statistically significant differences (p≥0.95) are reported: b (99% compared to no polymer), k (95% compared to P2), l (99% compared to P2), and n (99% compared to P4).

The data in FIGS. 18-20 show the frequency response data for the polymeric compounds studied. As indicated by this data, the mass of fibrinogen adsorbed in the second step was highly dependant on the nature of the barrier material employed. The ratio for the control samples with no polymer ($Fg_2/Fg_1$=0.54±0.05), is shown on the figures as a horizontal line for reference. Statistical differences (p>0.95 and p>0.99) are indicated on the graphs. The P3 polymer conjugate with the high level of peptide conjugation (P3-H), which appears to be missing from the data, exhibited complete suppression of the second fibrinogen step in three experiments. As a result, all frequency responses for this material are reported as zero. Several other materials, including the peptide controls and the P4 conjugates and the PMAA conjugates PMAA-L and PMAA-S, exhibited significant levels of inhibition of the fibrinogen adsorption ratio. Several of the unconjugated polymers (PMAA, P2, and P4) also increased the second fibrinogen adsorption ratio (116%, 384%, and 195%, respectively). The low level peptide conjugates of the long PEG chain polymers (P1-L and P3-L) failed to demonstrate suppression of fibrinogen adsorption.

Figure 21:
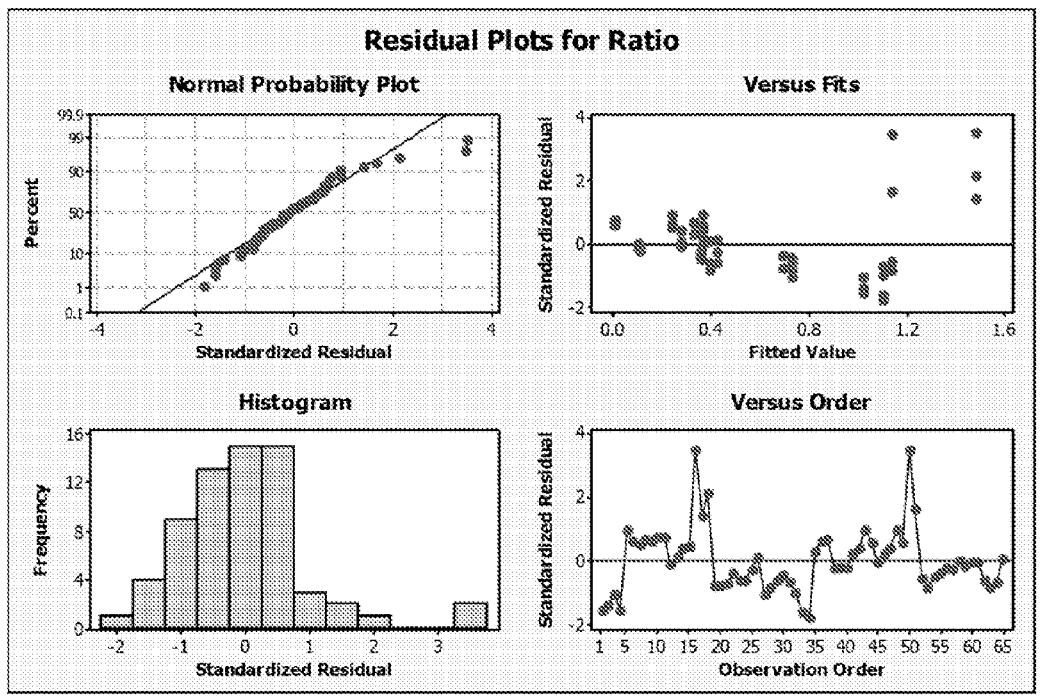
FIG. 21 includes graphs showing residual plots for the fibrinogen adsorption ratios presented in FIGS. 18-20, including a normal probability plot, a standardized residual fits graph, a frequency of residual histogram, and a residual versus observation order graph.

The residual plots for fibrinogen adsorption, shown in FIG. 21, demonstrate that, with the exception of two notable outliers (P2 and P4), the normal probability plot is linear and that the residuals are normally distributed. The main effects plots, shown in FIG. 22, indicate that the fibrinogen ratio should decrease with increasing chain length and with increasing PEG chain length. The number of PEG chains does not show any clear trend. The two peptides appear to reduce the value for the fibrinogen ratio, as does an increase in the number of peptides conjugated to the polymer.

Figure 23:
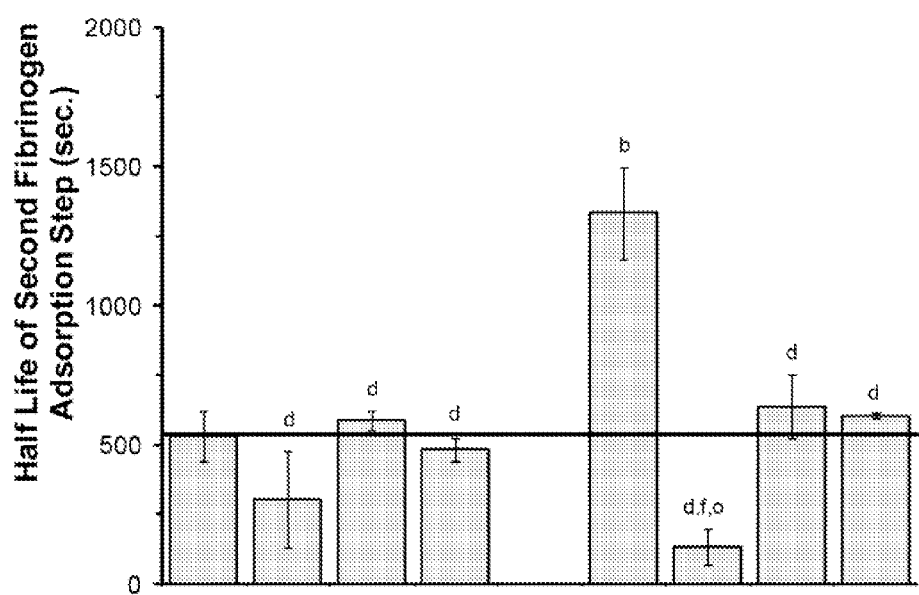
FIG. 23 is a graph showing the fibrinogen adsorption kinetics for a second fibrinogen adsorption to quartz crystals onto which various exemplary polymeric compounds (PMAA polymers) were adsorbed, where: the values presented represent the kinetic half-life seen in the second fibrinogen adsorption step; the horizontal bar represents the half-life observed for the control samples with no polymeric compound treatment; and statistically significant differences (p≥0.95) are reported: b (99% compared to no polymer), d (99% compared to PMAA), f (99% compared to PMAA-H), and o (95% compared to CAERK).
Figure 24:
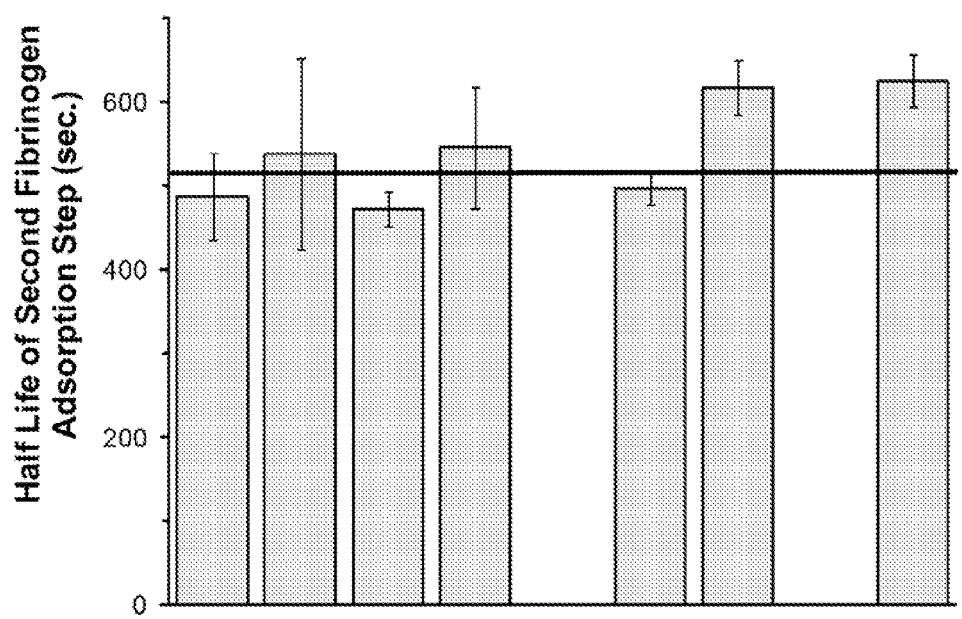
FIG. 24 is a graph showing the fibrinogen adsorption kinetics for a second fibrinogen adsorption to quartz crystals onto which various exemplary polymeric compounds (long ($M_N$=1,100) PEG chain polymers) were adsorbed, where the values presented represent the kinetic half-life seen in the second fibrinogen adsorption step and where the horizontal bar represents the half-life observed for the control samples with no polymeric compound treatment.
Figure 25:
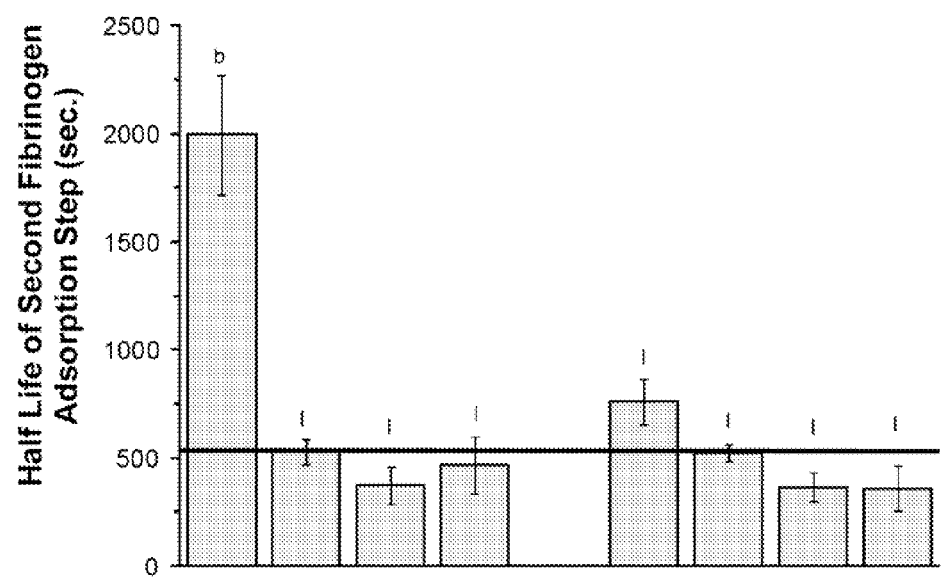
FIG. 25 is a graph showing the fibrinogen adsorption kinetics for a second fibrinogen adsorption to quartz crystals onto which various exemplary polymeric compounds (short ($M_N$=300) PEG chain polymers) were adsorbed, where: the values presented represent the kinetic half-life seen in the second fibrinogen adsorption step; the horizontal bar represents the half-life observed for the control samples with no polymeric compound treatment; and statistically significant differences (p≥0.95) are reported: b (99% compared to no polymer), and l (99% compared to P2).

The results of the kinetic analysis for the second fibrinogen adsorption step are presented in FIGS. 23-25. The half-life for the control samples without polymer adsorption ($t_{1/2}$=530±90 s) is shown on these graphs for reference. Since no fibrinogen was observed adsorbing to the surface for PS-3, no value is reported for this material. While there are differences among the materials tested, only PMAA ($t_{1/2}$=1330±160 s) and P2 ($t_{1/2}$=2000±280 s), demonstrated a significant difference from the control.

Figure 26:
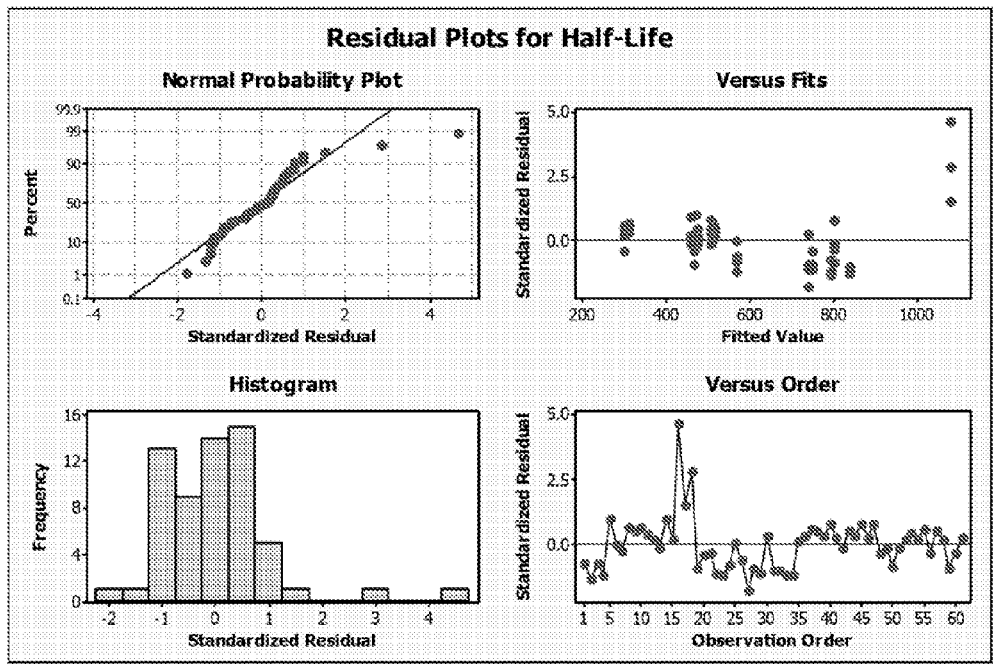
FIG. 26 includes graphs showing residual plots for the kinetic half-life of the second fibrinogen adsorption data depicted in FIGS. 23-25, including a normal probability plot, a standardized residual fits graph, a frequency of residual histogram, and a residual versus observation order graph.
Figure 27:
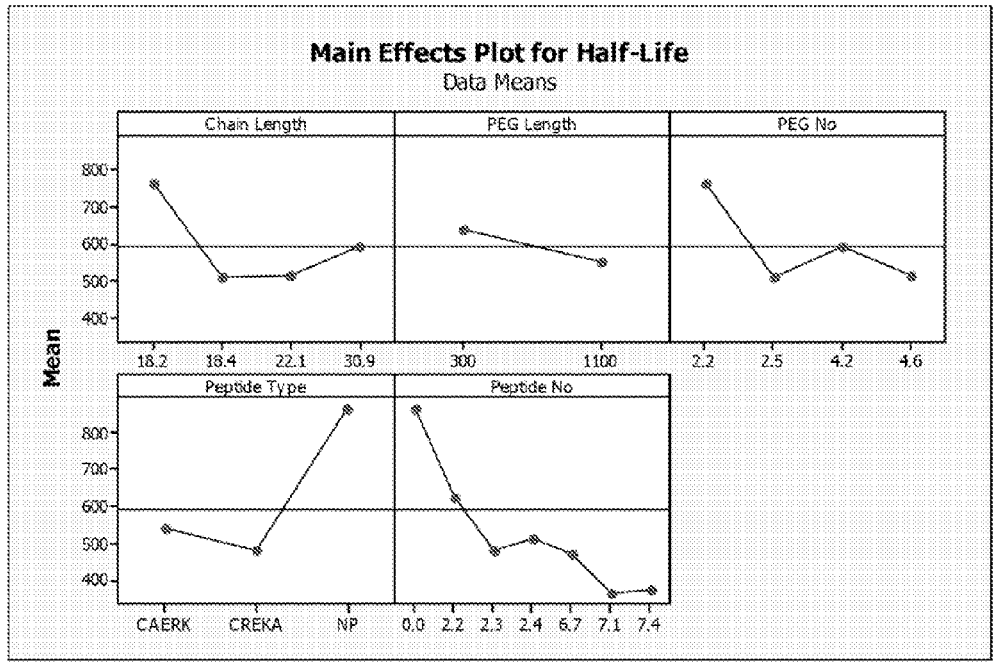
FIG. 27 includes graphs showing the main effects plots for the kinetic half-life of the second fibrinogen adsorption data depicted in FIGS. 23-25, and showing the results of varying certain aspects of the polymeric compounds.

The residual plots for the kinetics of fibrinogen adsorption, shown in FIG. 26, confirm that, with the exception of 2 outliers (both P2), the normal probability plot is linear and the residuals are normally distributed. The main effects plots, shown in FIG. 27, indicate that the rate of fibrinogen adsorption is not a strong function of chain length. The kinetics slow with increasing PEG chain length and with an increasing number of PEG chains. The two peptides appear to reduce the rate of fibrinogen deposition, as does an increase in the number of peptides conjugated to the polymer.

As noted herein above, the ability of the polymeric compounds to retard propagation of the FGM was then also assessed using a turbidity analysis to assess the kinetics of FGM formation from a fibrin-coated surface. Previous studies have demonstrated that surface adsorbed fibrin layers formed in this manner retain approximately five active thrombin molecules per fibrinogen molecule after rinsing with buffer solution [174]. These surfaces, then, can react with fibrinogen solutions to form a fibrin gel on the surface. In this regard, a microplate assay was thus employed to monitor the reaction of surface bound fibrin with solution phase fibrinogen after treatment with various materials and to investigate the structure of the resulting fibrin gels [175,176]. Briefly, to first prepare the fibrin gel substrate (i.e., the fibrin-coated surface), a Costar high binding 96-Well EIA/RIA plate was used to maximize the strength of interaction between the fibrin gel and the microplate. In order to create a stable gel on the surface, fibrinogen (50 μL, 2.0 mg/mL), thrombin (20 μL, 2.5 U/mL), and calcium chloride (10 μL, 100 mM) were then added to each well. The resulting gel was subsequently allowed to cure for 5 hours at room temperature, and each well was then rinsed twice with 200 μL TBS with care being taken to avoid removing the fibrin gel from the surface. A solution of each polymeric compound under investigation (50 μL, 0.10 mg/mL in TBS, n=4) was then added to the wells.

After treating each gel with the various polymeric compounds under investigation, 150 μL of fibrinogen (0.5 mg/mL in TBS) was added to each well. In order to observe the change in turbidity with time, a Cary Win-UV UV-visible spectrophotometer was used to monitor the UV absorbance at 350 nm for 90 minutes with an average time of 0.5 seconds using a two minute collection interval.

Figure 28:
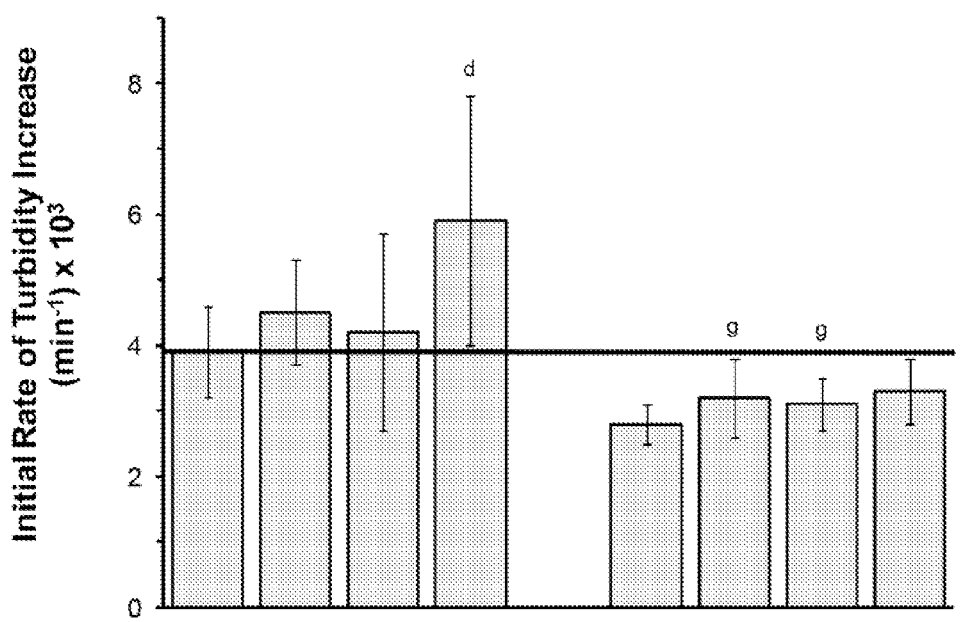
FIG. 28 is a graph showing the kinetic analysis of fibrin gel propagation from a fibrin surface onto which no polymeric compounds were adsorbed or onto which various polymeric compounds (PMAA) were adsorbed, where: the values presented represent the initial rate of turbidity increase observed during fibrin propagation; the horizontal bar represents the half-life observed for the control samples with no polymer compound treatment; and statistically significant differences (p≥0.95) are reported: d (99% compared to PMAA), and g (95% compared to EPC).
Figure 29:
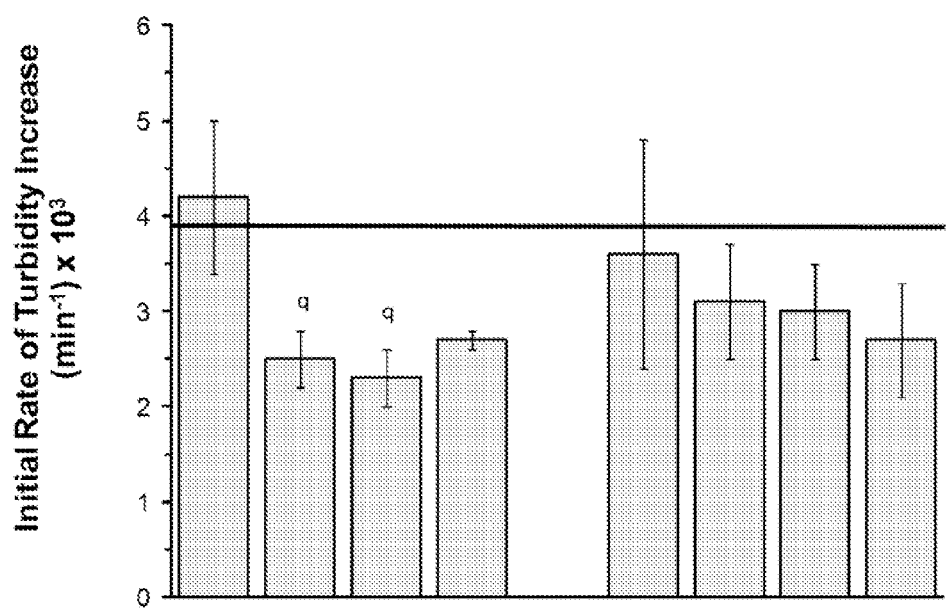
FIG. 29 is a graph showing the kinetic analysis of fibrin gel propagation from a fibrin surface onto which no polymeric compounds were adsorbed or onto which various polymeric compounds (long ($M_N$=1,100) PEG chain polymers) were adsorbed, where: the values presented represent the initial rate of turbidity increase observed during fibrin propagation; the horizontal bar represents the half-life observed for the control samples with no polymer compound treatment; and statistically significant differences (p≥0.95) are reported: q (95% compared to P1).
Figure 30:
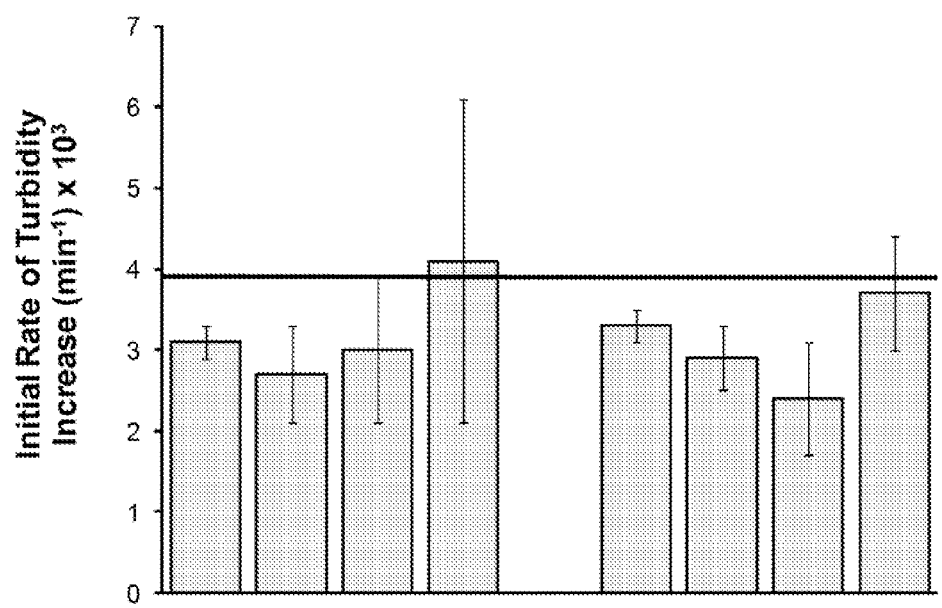
FIG. 30 is a graph of showing the kinetic analysis of fibrin gel propagation from a fibrin surface onto which no polymeric compounds were adsorbed or onto which various polymeric compounds (short ($M_N$=300) PEG chain polymers) were adsorbed, where the values presented represent the initial rate of turbidity increase observed during fibrin propagation and where the horizontal bar represents the half-life observed for the control samples with no polymer compound treatment.

In order to assess the ability of materials to block propagation of the fibrin gel matrix from a fibrin surface, a kinetic assay was performed using the data obtained from the ultraviolet spectrophotometry. After subtracting the initial absorbance values due to the preexisting fibrin layer in the microplate wells, the initial increase in turbidity could readily be observed. The rate of turbidity increase was approximated by fitting the initial data with a linear equation and determining the slope of the resulting line. As shown by the data in FIGS. 28-30, the value of this rate varied with the structure of the barrier material. The TBS control exhibited a value of 0.0039±0.0007 $min^{-1}$. There were no significant differences observed between the samples and the controls. Some statistically significant differences, however, were seen among the polymer samples.

Figure 31:
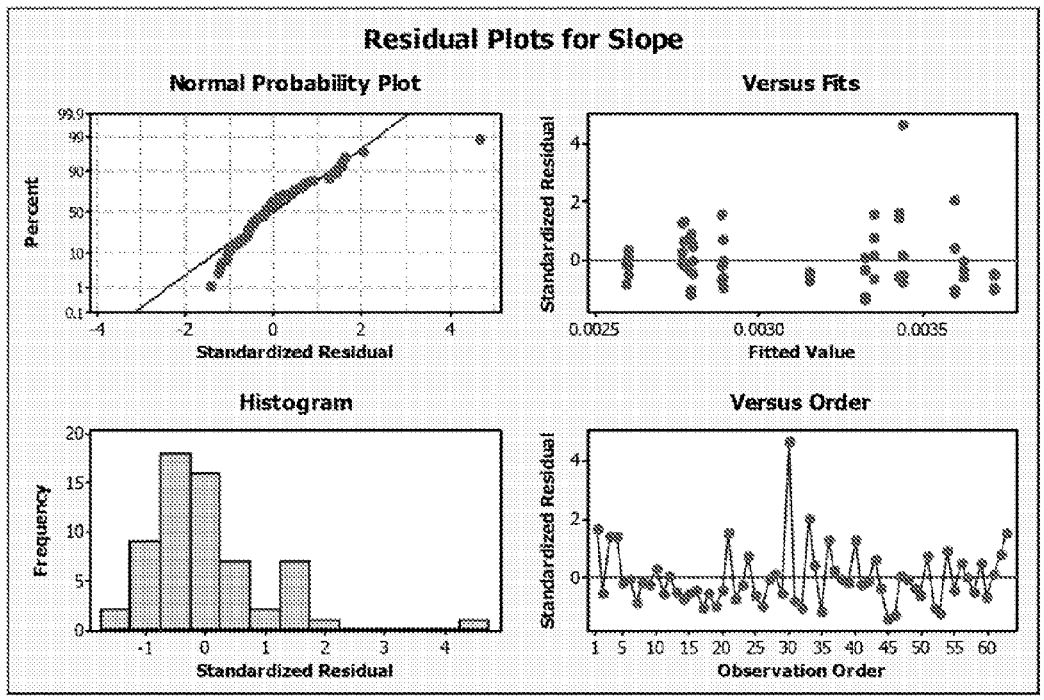
FIG. 31 includes graphs showing residual plots for the kinetic analysis data depicted in FIGS. 28-30, including a normal probability plot, a standardized residual fits graph, a frequency of residual histogram, and a residual versus observation order graph.
Figure 32:
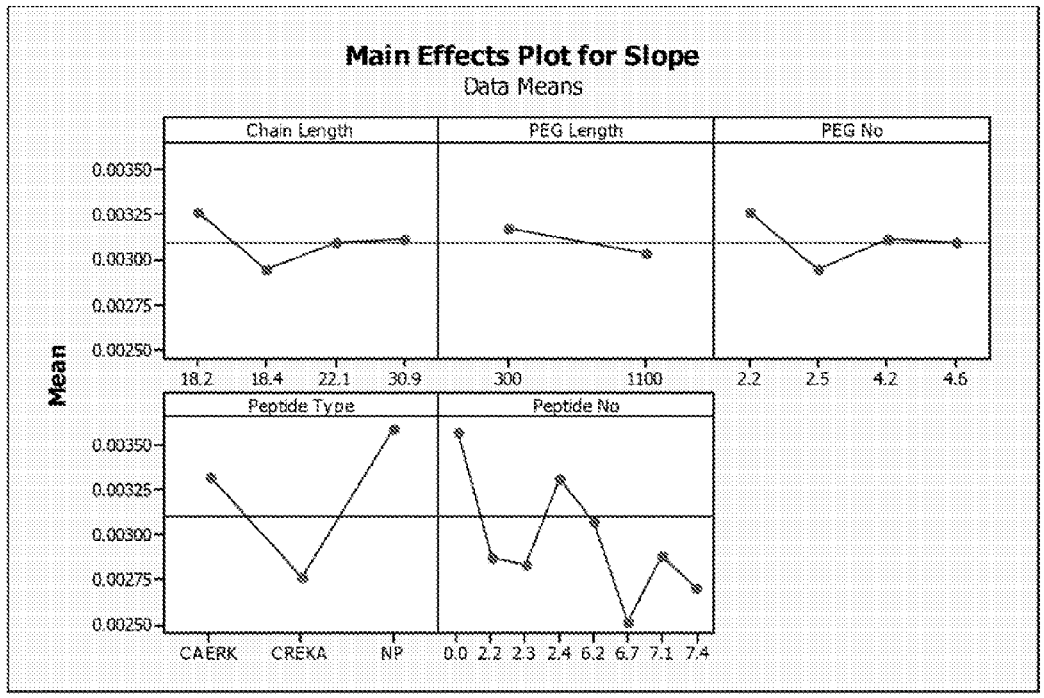
FIG. 32 includes graphs showing main effects plots for the kinetic analysis data depicted in FIGS. 28-30, and showing the results of varying certain aspects of the polymeric compounds.

The residual plots for the kinetics of fibrinogen propagation, shown in FIG. 31, confirm that, with the exception of one outlier, the normal probability plot is linear and the residuals are normally distributed. The main effects plots, shown in FIG. 32, indicate that the rate of fibrinogen propagation is not a strong function of chain length or number of PEG chains. The kinetics slow with increasing PEG chain length and with an increasing number of peptides conjugated to the structure. The CREKA peptide appears to reduce the rate of fibrinogen deposition, while the impact of the CAERK scramble is much less pronounced.

As also noted herein above, in order to test the anti-cellular adhesive properties of the various polymeric compounds, a complementary cell culture study was further carried out using the mouse mesenchymal D1 cell line (American Type Culture Collection (ATCC®) No. CRL-12424) in 24-well tissue culture plates. That pluripotent cell line was selected due to its strong adherence to charged surfaces and wound healing components (e.g., collagen I and fibrin) [161-164].

In those cell culture experiments, stable fibrin gels were first created in the well plates for use as a substrate to measure cellular attachment. In this regard, Tris-buffered saline was filtered through a 0.22 μm syringe filter and solutions (13.2 mg/mL fibrinogen, 5 U/mL thrombin, and 100 mM $CaCl_2$) were prepared in a laminar flow hood to minimize microbial contamination. In each well, 152 μL fibrinogen solution was then subsequently mixed with 40 μL $CaCl_2$ solution and 8 μL thrombin solution to yield a solution that was 10 mg/mL fibrinogen, 20 mM $CaCl_2$, and 0.2 U/mL thrombin. This solution was allowed to gel at room temperature for 1 hour and was then allowed to mature overnight at 4° C.

After maturing the fibrin gels overnight and rinsing the wells 3 times with sterile TBS, polymeric compound-containing solutions were then added (200 μL, 0.10 mg/mL in sterile TBS) and incubated at 37° C. for 90 minutes. The polymer solutions were then removed from the wells, and each well was rinsed 3 times with sterile TBS. Each well was then seeded with 250,000 cells in 500 μL Dulbecco's Modified Eagle Medium (DMEM, HyClone Laboratories, Logan, Utah) containing 10% fetal bovine serum (GIBCO/Invitrogen, Carlsbad, Calif.) and incubated at 37° C. for two hours. Untreated tissue culture polystyrene (TCP) fibrin gels with no anti-adhesion barrier were employed as controls, and a minimum of 6 replicates were studied for each polymeric compound.

After incubation, unattached cells were removed from the wells by rinsing three times with sterile TBS. Representative images of the cells were obtained using an inverted phase contrast microscope. The cells remaining on the surface after rinsing were lysed by sonication in high salt solution (0.05 M $NaH_2PO_4$, 2 M NaCl, and 2 mM EDTA). DNA contents, measured using Hoechst 33258 stain, were used to quantify the number of cells in each well [165,166]. In short, Hoechst 33258 (final concentration, 0.5 μg/ml, Sigma) was allowed to react with lysates in the dark for 10 minutes, after which fluorescence was measured ($\lambda$=356 nm and $\lambda_{em}$=458 nm). An exponential calibration curve was then prepared using samples with known DNA concentrations (0.16-5.0 μg/mL). After measuring the fluorescence of each well, this calibration was employed to determine concentration of DNA in each well. Since the duration of the experiment was not long enough for appreciable cell growth to occur, this value was used as a measure of the cells attached in each well.

Figure 33:
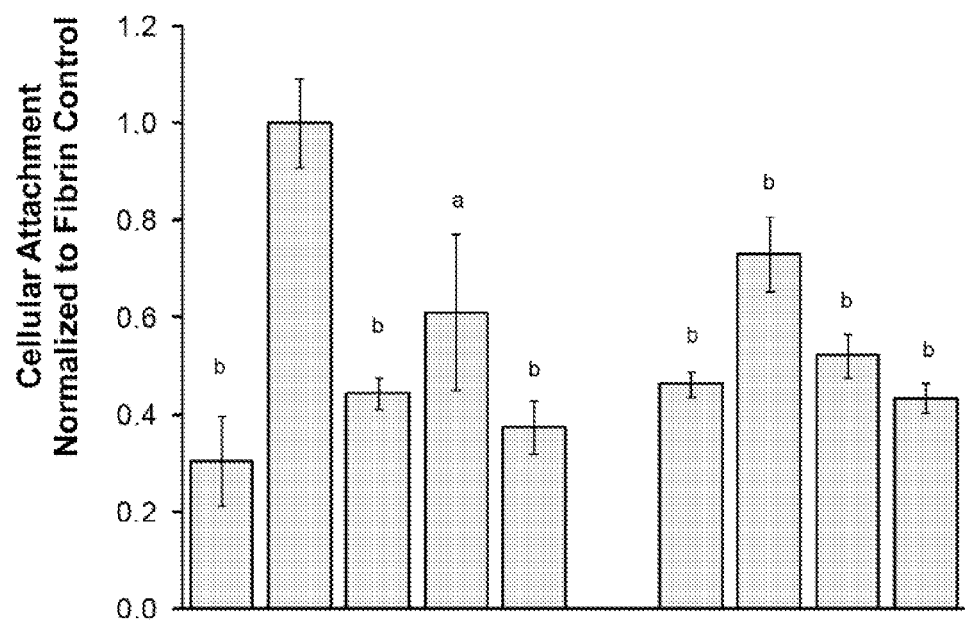
FIG. 33 is a graph showing normalized cellular attachment data depicting the extent of cellular attachment to a fibrin-coated surface onto which no polymeric compounds were adsorbed or onto which various polymeric compounds (PMAA) were adsorbed, where the values presented represent the degree of cellular attachment, based on a DNA assay, normalized to fibrin controls, and where statistically significant differences ($p \geq 0.95$) are reported: a (95% compared to no polymer compound), and b (99% compared to no polymer compound).
Figure 34:
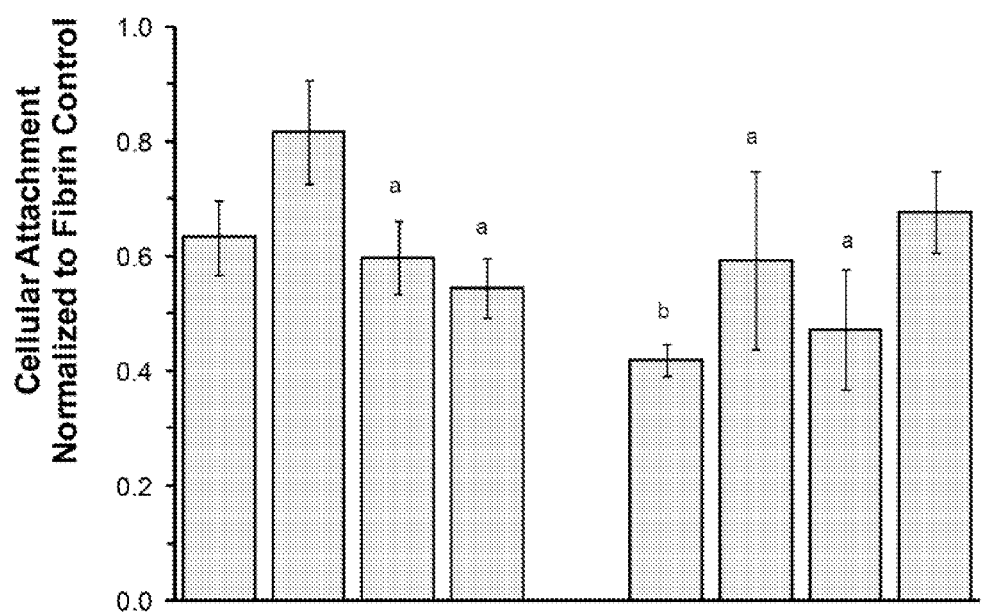
FIG. 34 is a graph showing normalized cellular attachment data depicting the extent of cellular attachment to a fibrin-coated surface onto which no polymeric compounds were adsorbed or onto which various polymeric compounds (long ($M_N$=1,100) PEG chain polymers) were adsorbed, where the values presented represent the degree of cellular attachment, based on a DNA assay, normalized to fibrin controls, and where statistically significant differences ($p \geq 0.95$) are reported: a (95% compared to no polymer), and b (99% compared to no polymer).
Figure 35:
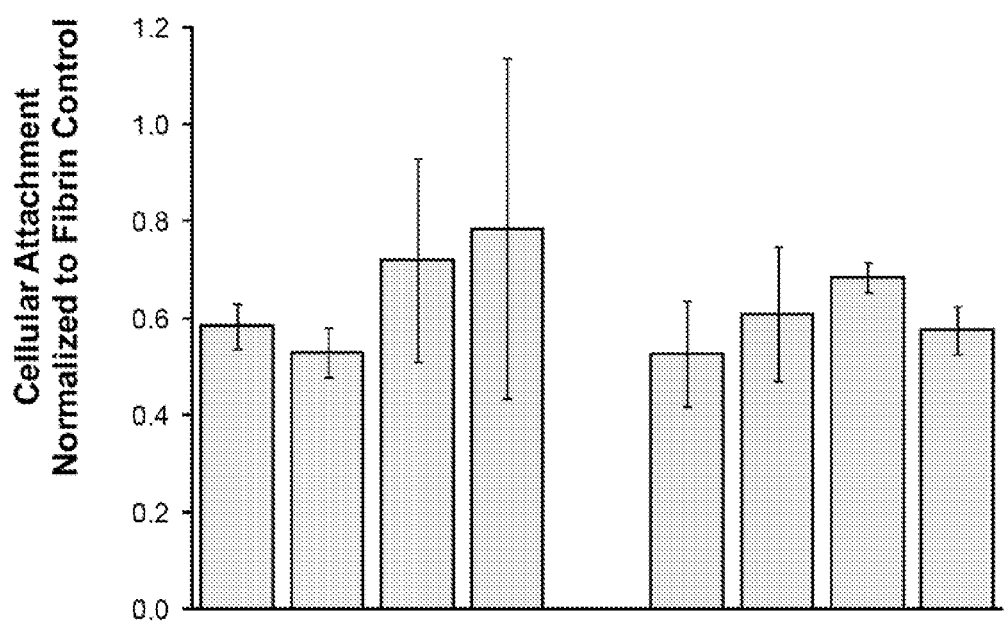
FIG. 35 is a graph showing normalized cellular attachment data depicting the extent of cellular attachment to a fibrin-coated surface onto which no polymeric compounds were adsorbed or onto which various polymeric compounds (short ($M_N$=300) PEG chain polymers) were adsorbed, where the values presented represent the degree of cellular attachment, based on a DNA assay, normalized to fibrin controls.
Figure 36:
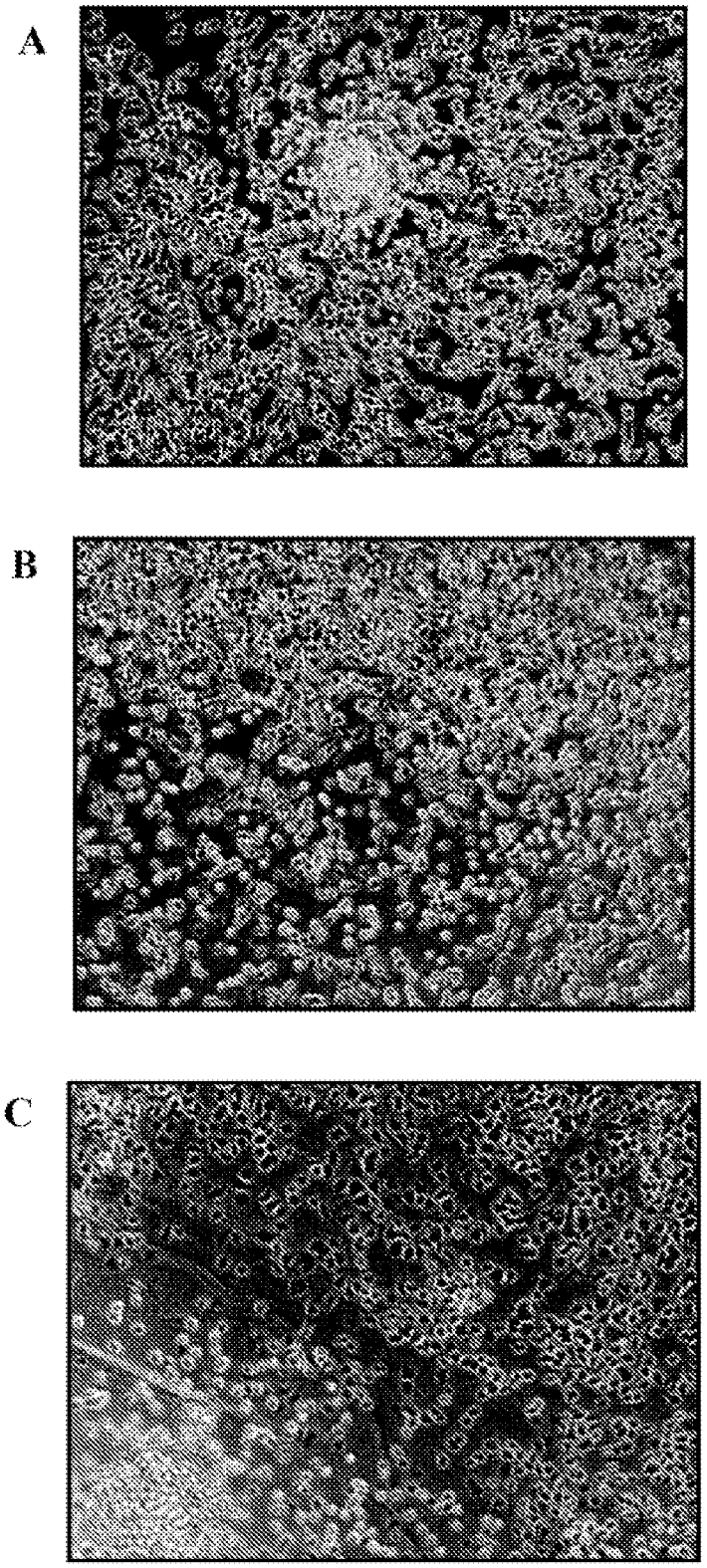
FIGS. 36A-C include images of cells attached to a fibrin gel after treatment with various exemplary polymeric compounds including PMAA-S (FIG. 36A), P1-L (FIG. 36B), and P1-S (FIG. 36C).

The results of the cellular attachment study, shown in FIGS. 33-35, indicated that many of the polymeric compounds significantly reduced the attachment of cells to the model fibrin surface. All of the PMAA polymers resulted in a significant reduction of cellular attachment, while the majority of the long PEG chain polymers showed an effect. There were no significant differences observed with the short PEG chain polymers. As shown in FIGS. 36A-36C, images taken of the wells indicate that the cells were not uniformly distributed on the fibrin surface. This artifact of the cell loading procedure made accurate visual comparisons of the cells difficult.

Figure 37:
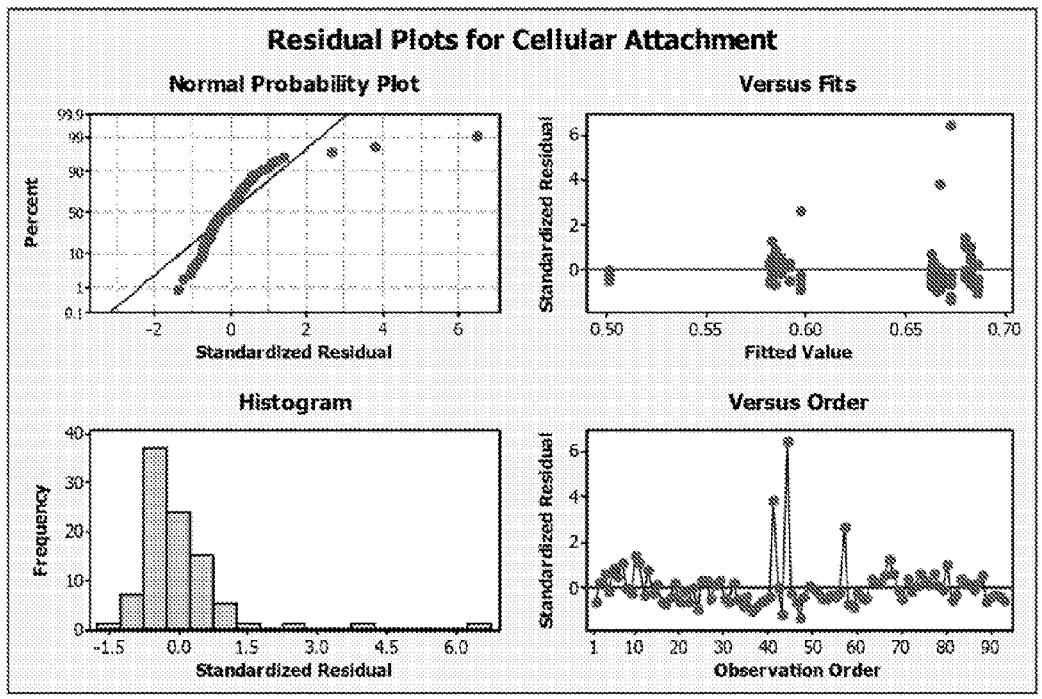
FIG. 37 includes graphs showing residual plots for the cellular attachment data depicted in FIGS. 33-35, including a normal probability plot, a standardized residual fits graph, a frequency of residual histogram, and a residual versus observation order graph.
Figure 38:
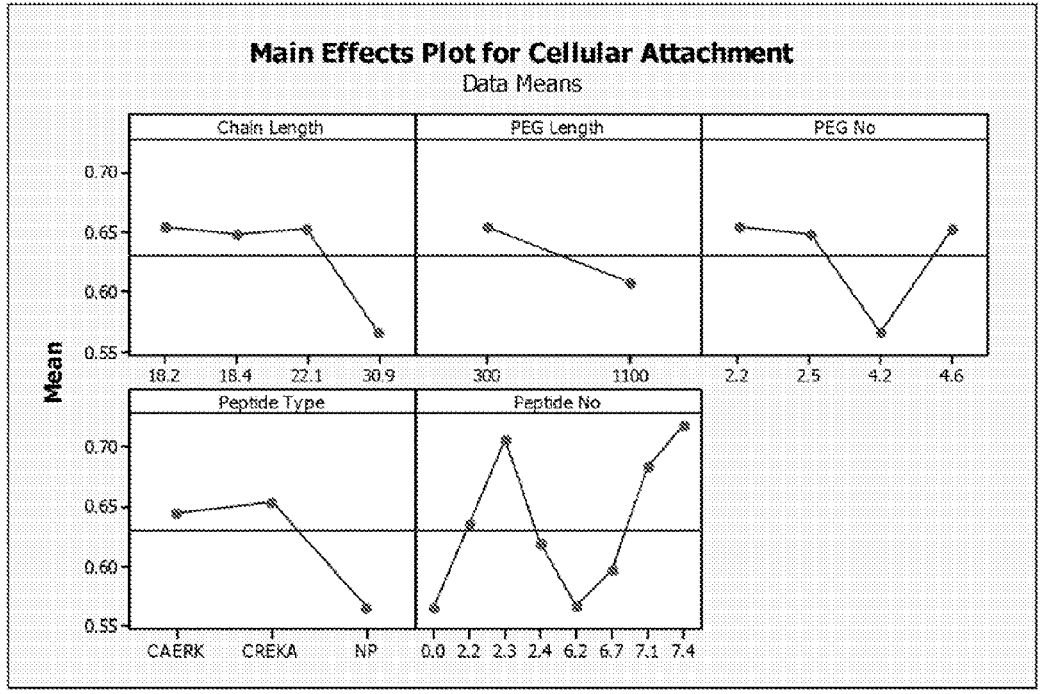
FIG. 38 includes graphs showing main effects plots for the cellular attachment data depicted in FIGS. 33-35, and showing the results of varying certain aspects of the polymeric compounds.

The residual plots for the cellular attachment to the fibrin substrate are shown in FIG. 37. With the exception of 1 outlier, the normal probability plot is linear and the residuals are normally distributed. The main effects plots, shown in FIG. 38, suggest that the degree of cellular attachment decreases with increasing chain length and with increasing PEG chain length. Cellular attachment does not appear to be a function of the number of PEG units nor of the number of peptide units in the structure. The presence of peptide, both CREKA and CAERK, appears to promote cellular attachment.

The foregoing studies, including the QCM analysis, turbidity assay, and cellular attachment study, provided numerous insights that were obtained from the pair wise comparison data. The ratio of fibrinogen adsorption in the QCM-D was studied to monitor the ability of the polymeric compounds to reduce the affinity of surfaces for fibrinogen. One particular finding in these experiments was the complete suppression of the second fibrinogen adsorption by the high molecular weight polymer with long PEG chains and a high level of CREKA (P3-H). Compared to the rest of the polymer architectures, this structure appeared to represent a sufficient balance of surface affinity (due to the high peptide content) and protective ability (due to the long PEG chains). The difference observed between the short polymer chains and long polymer chains were also notable. The shorter polymer chains appeared to be much less effective at inhibiting fibrinogen adsorption, potentially as a result of the action of the PEG groups on the peptide units. On the other hand, the long PEG chains appeared to articulate and form a hydration shell of approximately the same dimensions as the shorter polymer and shielded the attached peptide units from interacting strongly with the fibrin surface. The longer polymer chains extend past this shell and present readily available peptide units to the active surface.

Further, the rate of fibrinogen adsorption, while similar for most of the materials, appears to be slowed for the PMAA and P2 polymers. Without wishing to be bound by any particular theory, it is believed that this apparent reduction in rate is an artifact of mass transfer limitations related to the very high level of fibrinogen adsorbed for these materials.

Most of the polymers appeared to slow the kinetics of fibrin propagation. Due to the wide degree of variability in the data, however, very few statistically significant differences were observed in this rate. The phospholipid (EPC), on the other hand, appeared to enhance the rate of fibrin propagation, which is likely from the simultaneous growth of phospho lipid lamella within the fibrin gel matrix structure. Since both of these structures can scatter light, such a mechanism would lead to the more rapid turbidity increase.

Additionally, several notable results were also seen in the cellular attachment studies. As a result of their highly negative charge, the PMAA polymers were surprisingly effective at reducing the observed cellular attachment. While few statistically significant differences were observed in the level of cellular attachment, all of the materials appeared to reduce attachment when compared to the untreated fibrin control. As such, it was deduced that all of the materials adsorb to the fibrin gel surface and can reduce cellular attachment through either steric hindrance or charge based repulsion.

Using statistical analysis, it was also possible to better determine the relationships between the molecular structure and the performance in these experiments. For example, the results obtained from the QCM experiments revealed several trends in the ability of the polymeric compounds to suppress fibrinogen adsorption. Those trends are summarized in Table 4 below, where: "−" indicates a decrease in the response when the variable value is increased; designations of "S" and "NS" indicate effects that are specific (S) or not specific (NS) to the type of peptide unit conjugated to the polymer; "*" indicates that the response only shows negative correlation with the variable for the longest polymer chains; and "NE" indicates no discernable effect from the variable.

TABLE 4

Effects of Variation in Molecular Architecture on Material Performance.

| Response | Experiment | | | |
|---|---|---|---|---|
| | Fibrinogen Adsorption Ratio ($Fg_2/Fg_1$) | Fibrinogen Deposition Half-Life | Fibrin Gel Propagation Half-Life | Cellular Attachment |
| Chain Length | — | NE | * | — |
| PEG Chain Length | — | — | — | — |
| Number of PEG Units | NE | — | NE | NE |
| Number of Peptide Units | — | — | — | NE |
| Peptide Type | NS | NS | S | NS |

Based on the data presented in Table 4, it was possible to identify several attributes of the polymer architecture that were relevant for the attenuation of post-surgical adhesion formation. The lengths of the polymer chain and the PEG chain both appeared to be relevant determinants of performance for the polymeric compounds. The number of PEG chains in each polymer molecule did not appear to be a significant factor in assessing the performance. Another relevant impact on performance, however, appeared to arise from the peptide units. While the number of peptide units appeared to be relevant, unexpected results were observed when assessing the impact of the peptide type on material performance.

For all of the experiments, except cellular attachment, the number of peptide units conjugated to the polymer was a good predictor of the particular polymeric compound's performance. In most instances, however, the impact of the nature of the peptide was much less pronounced. This result was particularly surprising since CREKA had been shown to be an excellent targeting moiety for protein clots [119-122]. CAERK, on the other hand, was not anticipated to show a high affinity for fibrinogen. However, while polymers conjugated with CREKA and CAERK both inhibited the degree and rate of subsequent fibrinogen adsorption and reduced the level of cellular attachment to model surfaces, the CREKA-based materials were much more effective at reducing the propagation of fibrin from a surface. Without wishing to be bound by any particular theory, it was thought that these effects could be attributable to differences in the precise nature of the binding epitopes for the two peptide units. Both peptides exhibited an affinity for fibrin and directed polymeric materials to associate with the fibrin-coated surfaces and form barriers to subsequent protein adsorption and cellular attachment. The relative ineffectiveness of the CAERK materials at reducing fibrin polymerization from surfaces suggested that this peptide unit competed less effectively for the binding sites where subsequent fibrinogen polymerization occurred.

The effect of PEG chain length in each of the experiments indicated that longer polyethylene glycol units were more likely to result in a material that was likely to interrupt the PSA formation process. Further, the relationship between an increase in the PEG length and a decrease in the degree and kinetics of fibrinogen adsorption was likely a result of the increasing thickness of the hydrated PEG layer with longer PEG chains. As this layer becomes thicker, not only did the affinity of fibrinogen for the surface layer decrease, but mass transport limitations through this hydrated layer suppressed the rate of surface adsorption.

A similar mechanism also explained the ability of the long PEG chain materials to protect surfaces from cellular attachment and to retard the propagation of the fibrin gel matrix. The decrease in cellular attachment resulted from the inability of proteins to attach to thick, hydrated PEG layers. The decrease in the rate of fibrin propagation can arise from an increase in mass transport limitations due to hydrated PEG layer. In order for the solution phase fibrinogen to polymerize and form a fibrin gel, it must be activated with the surface bound thrombin. If this thrombin is coated with the PEG containing polymer, the fibrinogen must diffuse through this layer to the active site. Longer PEG chains, then, can inhibit the rate of fibrin gel propagation from the model surface more effectively than shorter PEG chains.

Surprisingly, the number of polyethylene glycol chains per polymeric compound did not appear to impact the fibrinogen blocking ability of the materials. Although the level of polymer adsorption could not be directly observed in these experiments, this lack of dependence on the concentration of PEG chains can result from self-assembly of a barrier and the formation of a surface layer with complete PEG coverage. Once this level of surface saturation was achieved, further adsorption of polymers to the surface was unlikely.

Numerous in vitro experiments have been performed to assess the ability of targeted polymers to interrupt the cascade of events that leads to the formation of PSAs. Employing a variety of statistical techniques, however, it was possible to identify several mechanistic features of the interactions of the described polymeric compounds with fibrin and fibrinogen. Longer PEG chains tended to inhibit a larger number of the potential pathways of PSA which were modeled. While the number of PEG chains in each polymer molecule did not appreciably affect the performance, the impact of the number of peptide units was dramatic. In addition, the subtle differences in the performance of the two peptides support the hypothesis that targeting can be used to direct the performance of materials to interrupt the formation of the fibrin gel matrix and prevent the formation of PSAs.

Example 5

Interaction Between CREKA Peptides and Fibrinogen

As described previously, the pentapeptide CREKA (SEQ ID NO: 1) has successfully been employed as a targeting unit to direct nanoparticles to tumor sites based on the high levels of fibrin present, which is due to the well-characterized leaky vasculature [116-121]. In addition, the molecular configuration of this peptide has been characterized under a variety of other conditions [122-124]. The experiments described in Example 4 demonstrated that that peptide can also be incorporated into polymers and used to interrupt the series of events that leads to an extended fibrin gel matrix and the promotion of post-surgical adhesion formation. To date, however, no analysis of the interaction of that peptide with fibrin, or its precursor, fibrinogen, have been reported.

To determine the nature of this interaction, two complementary approaches were employed. First, the structure of fibrin gels grown from surfaces treated with a series of polymeric materials was analyzed using a turbidity assay. Second, an optical technique known as circular dichroism (CD), was employed to probe the interaction of that peptide with fibrinogen in the solution phase. For the structural analysis of fibrin, all of the polymeric compounds included in Table 2 were employed. Circular dichroism was carried out with the free targeting peptide (CREKA) and a polymeric compound that was deemed to have a sufficient overall performance from previous experiments (P3-H). All materials were prepared as previously described.

Briefly, in order to investigate the structure of fibrin gels grown from the surface of existing fibrin substrates under a variety of conditions, a microplate-based turbidity analysis was first performed [175.176]. In these experiments, a Costar high binding 96-Well EIA/RIA plate was used to maximize the strength of interaction between the fibrin gel and the microplate. In order to create a stable gel on the surface, fibrinogen (50 µL, 2.0 mg/mL), thrombin (20 µL, 2.5 U/mL), and calcium chloride (10 µL, 100 mM) were then added to each well. The resulting gel was again allowed to cure for 5 hours at room temperature. Each well was then rinsed twice with 200 µL TBS, and care was taken to avoid removing the fibrin gel from the surface. A solution of each polymeric compound under investigation (50 µL, 0.10 mg/mL in TBS, n=4) was subsequently added to the wells.

After treating each gel with the polymeric compound under investigation, 150 µL of fibrinogen (0.5 mg/mL in TBS) was then added to each well. A partial UV-visible spectrum (350-500 nm) was collected for each well using the CaryWin UV UV-visible spectrophotometer. After 90 minutes, a second UV-visible spectrum was collected. The turbidity of the additional fibrin gel formed during the intervening 90 minutes was determined by subtracting the initial reading from the final reading at each wavelength.

As has previously been described, it was also possible to relate the turbidity of the resulting gel to the structure of its composite fibers [174, 180-183]. As shown in Equation 9, the turbidity ($\tau$) is a function of the absorbance, Abs, and the path length, b:

$$\tau = \frac{\ln(10) * \text{Abs}}{b} \quad (9)$$

For long, rod like particles, the relationship between turbidity and wavelength is described by Equation 10:

$$\tau = \frac{\left(\frac{88}{15}\right)\pi^3\eta\left(\frac{d\eta}{dC}\right)^2 C\mu}{N\lambda^3} \quad (10)$$

where $\eta$ is the refractive index of the solution, C is the concentration, $\mu$ is the mass/length ratio of the particles, N is Avagadro's number, and $\lambda$ is the wavelength of the incident light. Using published values for $\eta$ and for $(d\eta/dC)$ of 1.333 and 0.18 cm$^3$/g, respectively, this equation simplified to Equation 11 [180]:

$$\tau = \frac{6.52 \times 10^{-27}\mu}{\lambda^3} \quad (11)$$

As indicated by this expression, a plot of $\tau$ versus $$\left(\frac{6.52 \times 10^{-27}}{\lambda^3}\right)$$

should yield a straight line with a slope of $\mu$. Assuming an average well diameter of 0.661 mm, a 150 µL gel results in a path length of 0.437 cm. Equation 11 can thus be employed, and a plot of $\tau$ versus $$\frac{6.52 \times 10^{-27}}{\lambda^3}$$

will yield a straight line with a slope equal to the ratio of mass to length ratio of the fibrin fibrils ($\mu$) in Da/cm to relate the turbidity of the gel to its structure.

For the CD experiments that were employed to probe the interaction of the CREKA peptides with fibrinogen in the solution phase solution, fibrinogen was prepared in a UV transparent solvent. In this regard, solutions of fibrinogen (0.1 to 200 µg/mL), CREKA (100 µg/mL), and P3-H (100 µg/mL) were first prepared in a PBS buffer solution. Each of these solutions were then combined in appropriate ratios and diluted with PBS to prepare the samples shown in Table 5. All samples were prepared fresh on the day of the experiment to minimize degradation of the proteins in solution.

All CD measurement were performed at 37° C. using a Jasco J-810 Spectropolarimeter controlled by Jasco Spectral Measurement software. Spectra were collected from 320 to 200 nm. Each measurement was the average of four acquisitions collected in a 1.0 mm quartz cuvette, and each sample was measured three times. In order to avoid contamination between samples, the cuvette was cleaned with 1M nitric acid, rinsed with copious amounts of DI water and ethanol, and dried with acetone between samples. Analysis of blank PBS samples confirmed that this cleaning procedure removed all traces of the sample from the cuvette. In order to estimate the content of $\alpha$-helical and $\beta$-sheet secondary structure in the fibrinogen, each spectrum was analyzed using the K2D2 neural-network deconvolution algorithm [189-191].

Figure 39:
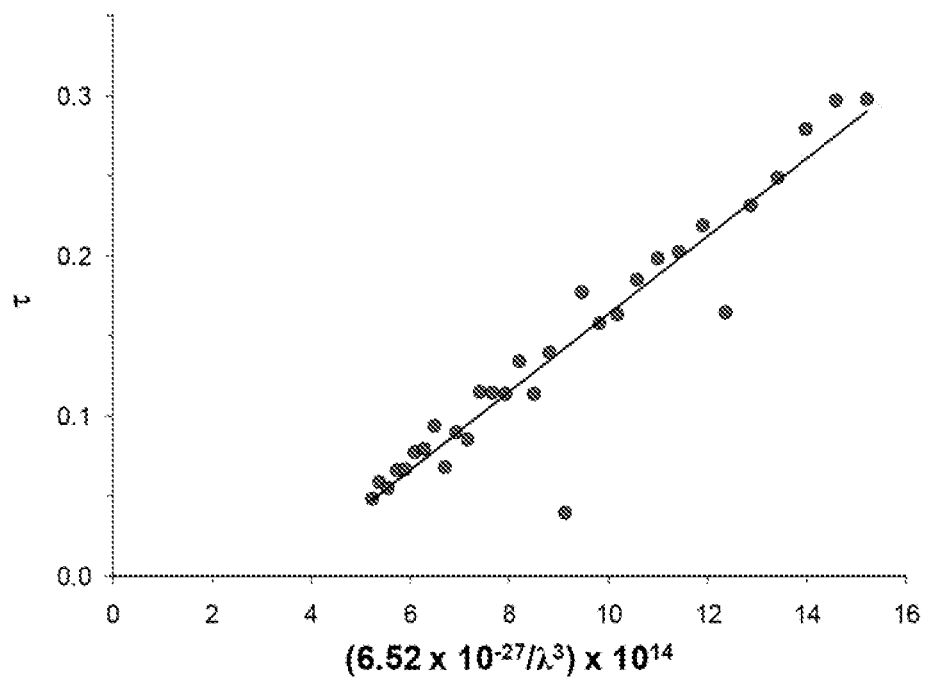
FIG. 39 is a graph showing the turbidity of a fibrin gel as a function of wavelength.
Figure 40:
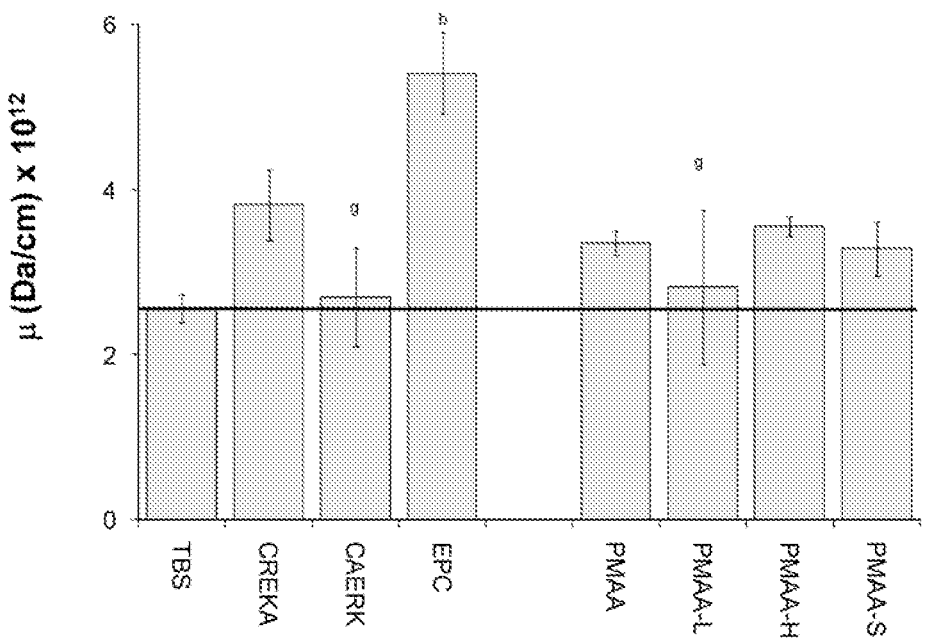
FIG. 40 is a graph showing the mass to length ratio of fibrin fibrils grown from surfaces treated with no polymeric compounds or treated with various polymeric compounds (PMAA Polymers), where the statistical significance is indicated as: b (99% compared to no polymer) and g (95% compared to EPC).
Figure 41:
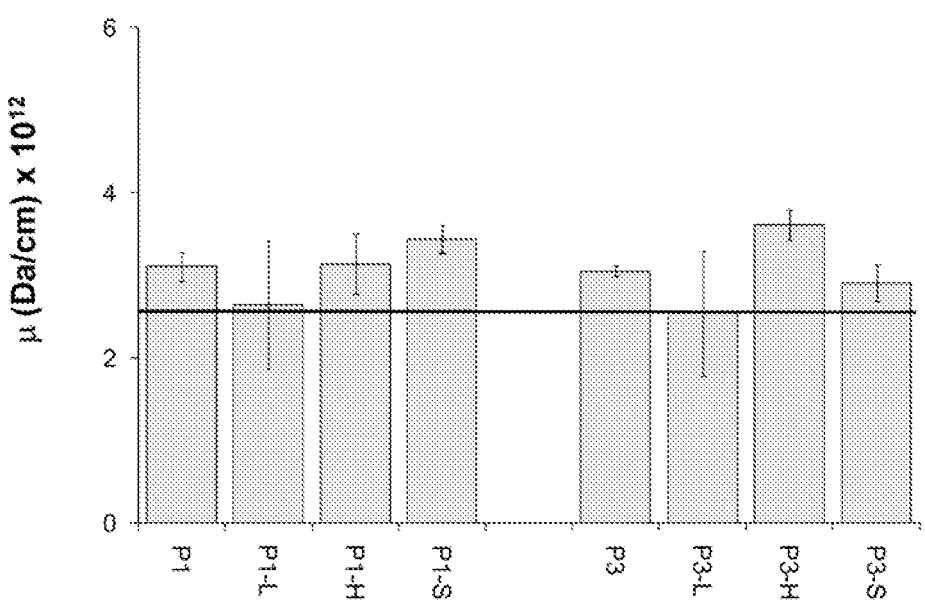
FIG. 41 is a graph showing the mass to length ratio of fibrin fibrils grown from surfaces treated with no polymeric compounds or treated with various polymeric compounds (long ($M_N$=1,100) PEG chain polymers).
Figure 42:
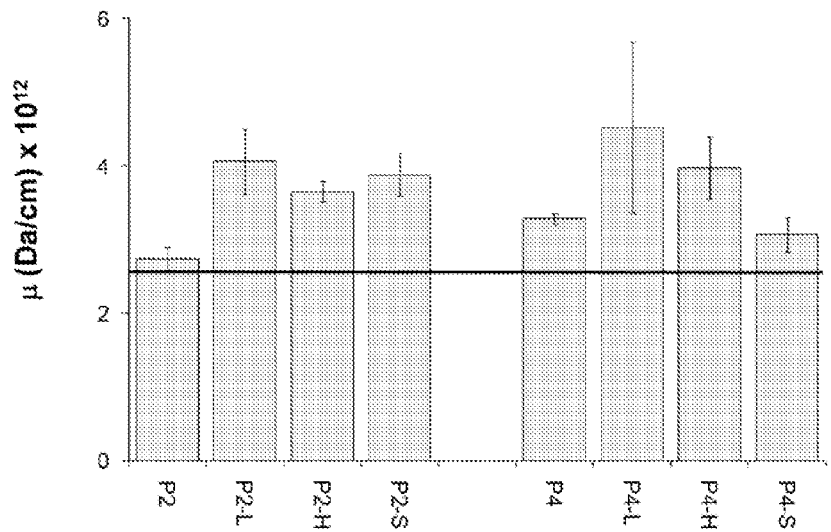
FIG. 42 is a graph showing the mass to length ratio of fibrin fibrils grown from surfaces treated with no polymeric compounds or treated with various polymeric compounds (short ($M_N$=300) PEG chain polymers).

Upon analysis from the results from the turbidity assay, and as shown in FIG. 39, a plot of $\tau$ versus $$\left(\frac{6.52 \times 10^{-27}}{\lambda^3}\right),$$

yielded a straight line, in good agreement with theory. Using a linear least squares analysis, data for each well was then analyzed. The results of this analysis, shown in FIGS. 40-42, summarize these results for the polymeric compounds tested. The control, with no polymer addition, yielded a value of $2.56 \times 10^{12} \pm 1.7 \times 10^{11}$ Da/cm and is shown on the figures as a horizontal line for reference. Only EPC exhibited a statistical difference from the TBS control.

Figure 43:
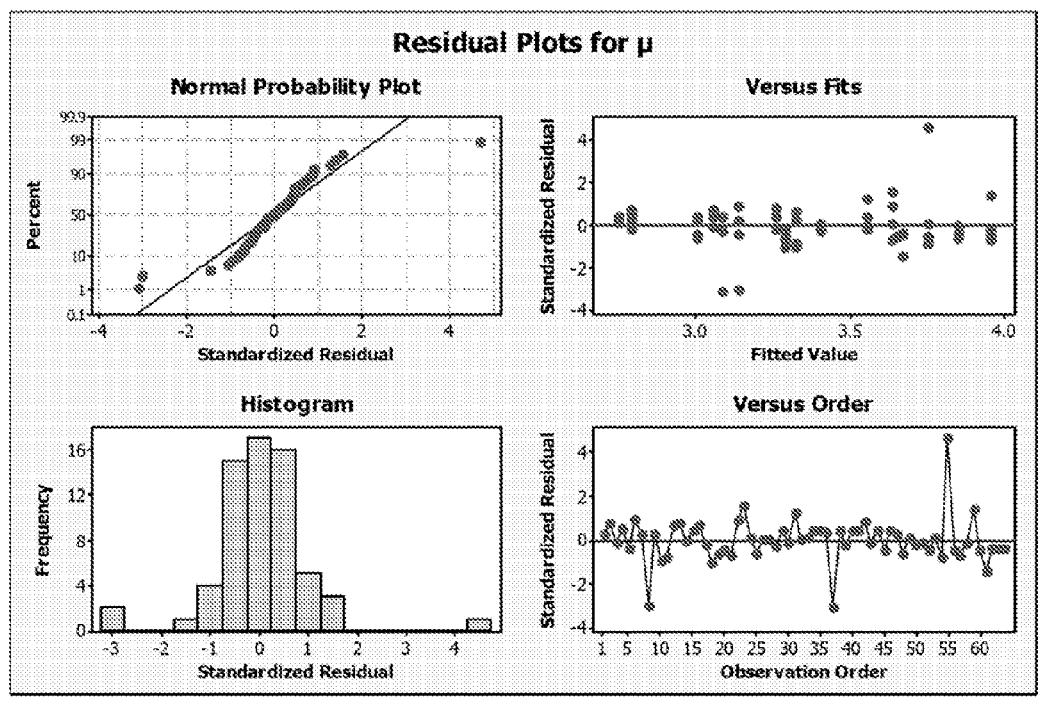
FIG. 43 includes graphs showing residual plots for the fibrin mass to length ratio data depicted in FIGS. 40-42, including a normal probability plot, a versus fits graph, a histogram, and a versus order graph.
Figure 44:
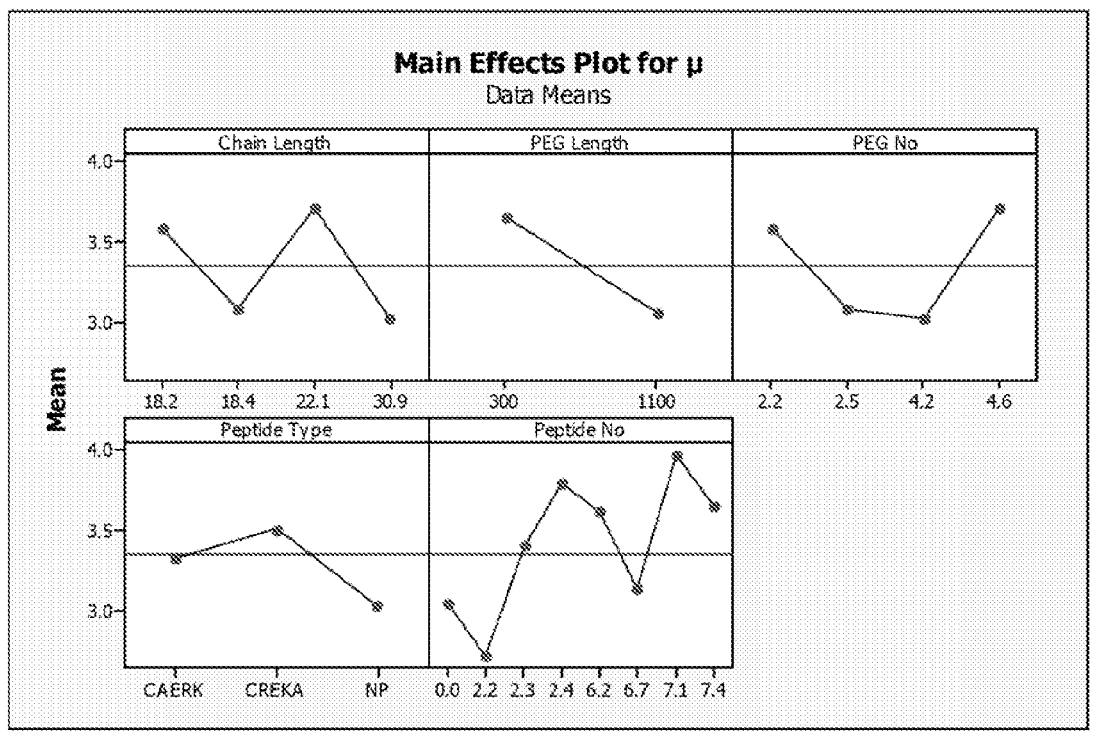
FIG. 44 includes graphs showing main effects plots for the fibrin mass to length ratio data depicted in FIGS. 40-42, and showing the results of varying certain aspects of the polymeric compounds.

The residual plots for $\mu$ are shown in FIG. 43. With the possible exception of 1 outlier, the normal probability plot was linear and the residuals were normally distributed. The main effects plots, shown in FIG. 44, indicated the mass/length ratio was not affected by the polymer chain length or the number of PEG chains. The value of $\mu$ decreased with increasing PEG chain length and increased with an increase in the number of peptides conjugated to the chain. No clear difference was observed as a function of peptide type.

Figure 45:
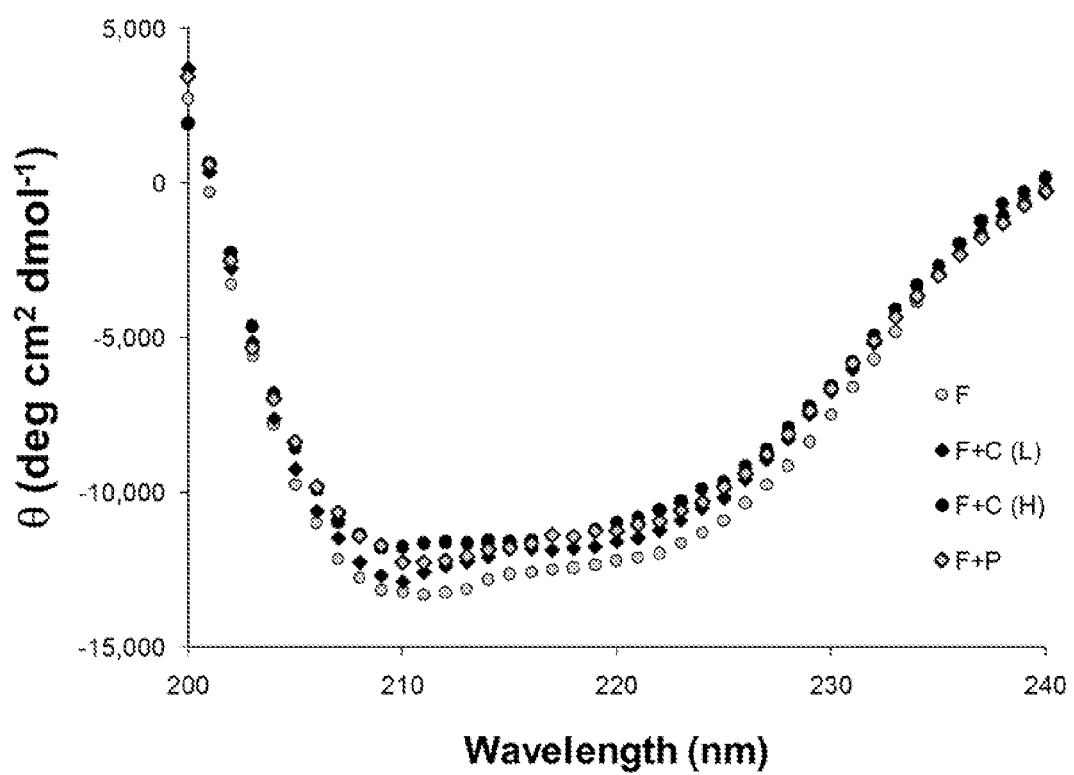
FIG. 45 is a graph showing a representative CD spectra for a solution containing 100 μg/ml fibrinogen (F), a solution containing 100 μg/ml fibrinogen plus 0.20 μg/ml of a CREKA basement membrane targeting peptide (F+C(L)), a solution containing 100 μg/ml fibrinogen plus 1.00 μg/ml of a CREKA basement membrane targeting peptide (F+C(H)); and for a solution containing 100 μg/ml fibrinogen plus 1.00 μg/ml of an exemplary polymeric compound (P3-H) (F+P).

Representative CD spectra for the samples tested are shown in FIG. 45. These spectra indicated a change in secondary protein structure with the addition of either CREKA or polymer. The intensity of the peak at 210 nm decreased with increasing CREKA concentration; the effect of the polymer (100 µg/mL) was approximately equivalent to the effect of 0.2 µg/mL of CREKA.

As shown in Table 5 below, the addition of CREKA to the fibrinogen solution resulted in a decrease in the α-helical content from 43.9±0.0 percent to 27.9±0.3 percent with the addition of 1.0 µg/mL CREKA. This reduction in α-helical content was accompanied by a concurrent increase in β-sheet content from 10.6±0.0 percent to 15.4±0.1 percent. The addition of 1.0 µg/mL P3-H to the fibrinogen solution resulted in a decrease in α-helical content to 33.0±3.1 percent and an increase in β-sheet content to 12.6±1.6 percent.

TABLE 5

Results of Circular Dichroism Measurements.

| Sample | Description | Molar Ratio of Peptide to Fibrinogen | α-Helix Content (Percent) (M ± SE) | β-Sheet Content (Percent) (M ± SE) |
|---|---|---|---|---|
| F | 100 µg/mL Fibrinogen in PBS | 0 | 43.9 ± 0.0 | 10.6 ± 0.0 |
| F + C(L) | 100 µg/mL Fibrinogen + 0.20 µg/mL CREKA in PBS | 1.13 | 39.1 ± 0.0 | 10.0 ± 0.0 |
| F + C(H) | 100 µg/mL Fibrinogen + 1.0 µg/mL CREKA in PBS | 5.63 | 27.9 ± 0.3 | 15.4 ± 0.1 |
| F + P | 100 µg/mL Fibrinogen + 1.0 p82 g/mL P3-H in PBS | 1.04 | 33.0 ± 3.1 | 12.6 ± 1.6 |

From the results obtained from these experiments, it was observed that the polymeric compounds tested in the turbidity assay and the CD studies had an effect on the structure of fibrin gels propagated from an existing fibrin surface. Although the individual comparisons shown in FIGS. 40-42, failed to reveal a strong significant difference among the samples, powerful ANOVA analysis conducted on the entire data set of polymer samples did reveal several, statistically significant, trends.

The effect of PEG chain length, indicating that longer PEG chains resulted in a decrease in the mass/length ratio for the fibrin fibrils, suggested that longer PEG chains were effective at inhibiting the deposition of fibrinogen to growing fibrin fibrils. Surprisingly, the number of PEG chains did not appear to impact the structure of the growing fibrin fibrils. This indicated that the steric effect of PEG chains on adjacent monomer units in the polymer failed to result in enhanced protection against protein deposition. It is possible that, in the environment tested, all of the PEG chains form a fully hydrated hydrophilic core. While it was difficult to determine the number of polymer chains adsorbed to the growing fibrin fibril, it was likely that a larger number of low PEG number polymer chains were able to adhere to the surface. As a result, the total number of PEG chains on the surface may be equivalent despite the difference in molecular architecture.

The somewhat surprising observation that polymer chain length did not affect the resulting fibrin structure can also be explained if it is assumed that the surface of the fibrin fibrils is saturated with polymer. Although the longer polymer chains occupied a larger surface area, the presence of additional polymer chains resulted in an equivalent effect on the polymerized protein structure.

Although the trend in protein structure that resulted from changing the peptide is ambiguous, it did appear that the presence of either CREKA of CAERK in the polymer structure resulted in an increase in the specific mass of the fibrils. This was confirmed by the clear trend observed that increasing the level of peptide conjugation increased the measured value of g. Two mechanisms may be responsible for this trend. If the presence of the peptide simply increased the affinity for the polymers to the fibrin fibril surface, it is conceivable that the observed increase simply resulted from the accumulation of polymer around the fibrin core. Another potential explanation for this observation was that the peptides on the polymer chain enhanced the deposition of fibrin around these growing fibrils.

The observations made with circular dichroism can be used to explain the interaction of CREKA with fibrin and its precursor, fibrinogen. The fibrinogen solution employed was prepared at a concentration of 100 µg/mL, or 0.29 µM. The peptide was employed at concentrations of 0.33 and 1.7 µM. Since CD of the free peptide did not reveal any secondary structure, all structural changes in the protein/peptide mixture were attributed to alterations in the conformation of fibrinogen. At a ratio of approximately 1:1, a decrease in the α-helical content of 4.8%, along with a decrease in β-sheet content of 0.6%, suggested that CREKA binds to α-helical domains of fibrinogen and resulted in significant conformational changes. The sample with increased peptide concentration (CREKA:fibrinogen 6:1) demonstrated a further decrease in α-helical content of 11.2% and an increase in β-sheet content of 5.4%. Although these observations did not provide sufficient detail to discern the precise nature of the interaction between CREKA and fibrinogen, the dramatic conformational change indicated that CREKA interacts strongly with solution phase fibrinogen. In addition, while the precise stoichiometry could not be determined, it was clear that there were multiple CREKA binding domains on each fibrinogen molecule.

The polymer sample (4.8 µM polymer, 30 µM CREKA units) also interacted strongly with the protein. The resulting decrease in α-helical and increase in β-sheet content (10.9 and 2.0 percent, respectively) suggested that the peptide conjugated polymer occupied multiple binding sites per molecule.

To summarize, the polymeric compounds tested for use as treatments for post-surgical adhesion prevention demonstrated the ability to bind to growing fibrin fibrils and to affect the architecture of the resulting structures. The observed trends indicated that PEG chain length and degree of peptide conjugation were relevant factors in the performance of the polymeric compounds. Circular dichroism measurements of fibrinogen with free peptide and with peptide-conjugated polymer further demonstrated strong interactions with the protein. This finding thus confirmed the ability of CREKA to serve as a useful moiety for targeting polymers to fibrinogen and fibrin.

Example 6

Reduction of Post-Surgical Adhesions In Vivo

To measure the extent of surgical adhesion formation, an in vivo surgical adhesion model is utilized as previously described [86,87]. Briefly, rats are anesthetized and, after disinfection, a midline laparotomy is performed. Both peritoneal surfaces of the lateral abdominal wall are exposed and a 2×30 mm long incision is made on each side, equidistant from the midline. The incision is then allowed to clot. 4 separate groups are tested including: a control group, which is sewn up after clotting occurs; a sham group which receives a saline wash; a fibrin targeted polymer solution group; and, a non-targeted PEG-PMA polymer solution. After coating of surfaces, the midline laparotomy is closed. After 1 week, animals are then euthanized and a U shaped incision is placed to expose the scar tissue. Scoring of adhesions is then performed by measuring the adhesions with calipers.

Figure 46:
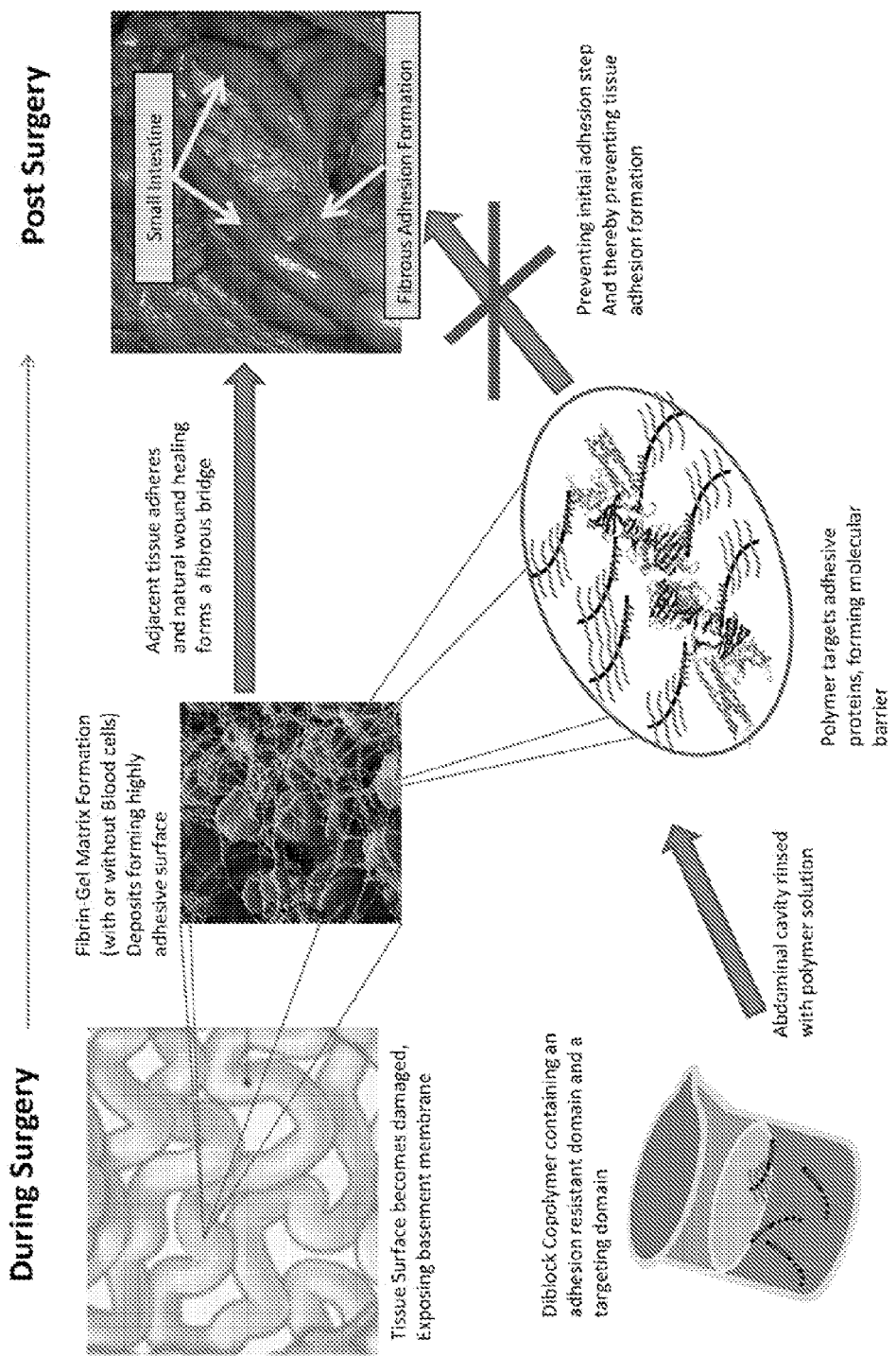
FIG. 46 is a schematic diagram showing an exemplary method of using a polymeric compound of the presently-disclosed subject matter to reduce the occurrence of a post-surgical adhesion.
Figure 47:
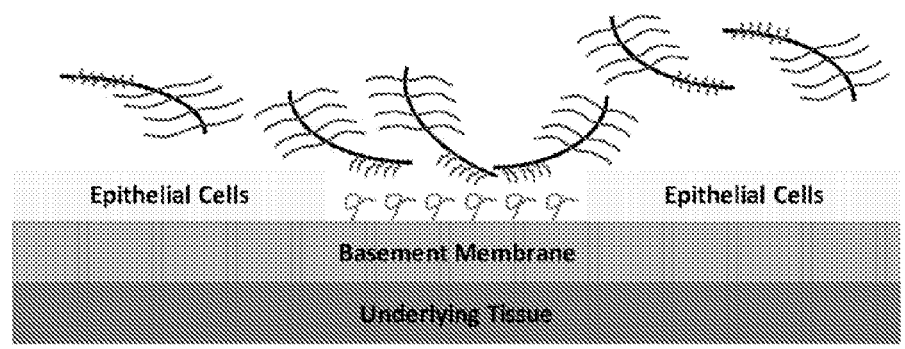
FIG. 47 is a schematic diagram showing a mechanism of reducing post-surgical adhesion formation by an exemplary polymeric compound where the targeting portions of the compounds bind to basement membrane peptides and the brush-like portions provide a steric barrier to reduce the occurrence of post-surgical adhesions.

At the end of one week, both control and sham animals possess extensive adhesion formation with approximately 60-70% of the cut surface engaged in a scar formation. Both polymer formulations reduce this extent of adhesion, with the targeted barriers possessing the greatest degree of adhesion resistance, thus indicating that the present-disclosed compounds are useful in a method of reducing the occurrence of post-surgical adhesions (see, e.g. FIGS. 46 and 47).

Example 7

Quantitative Fluorescence Determination of Polymer Barrier Assembly onto Tissue Grafts To test the capacity for detection, fibrin-coated surfaces are prepared in 96-well plates by incubating the plates for 30 min with 10 mg/ml fibrinogen followed by thrombin activation (0.2 U/ml). After 30 min, the wells are rinsed 3-times and the present compounds, including a fibrin-targeted polymer and a non-targeted polymer) are added to the wells (1-10 mg/ml) for 1 hr. After 1 hr, the wells are rinsed 5-times and fluorescence intensity is measured (Varian Eclipse, equipped with microplate reader attachment). An increase in fluorescence is observed in the wells incubated with a fibrin-targeted compound, thus indicating that the present compounds adhere to fibrin.

To determine the adherence of the present compounds to damaged tissue, polymer binding to ex vivo tissue grafts are evaluated using fluorescently-labeled compounds. Briefly, tissue samples are harvested from mice and rats and sectioned using a biopsy punch to maintain constant tissue areas. The tissue samples are then placed in 96-well plates for fluorescence binding assays as described above. An increase in fluorescence is observed in the wells incubated with a fibrin-targeted compound, thus indicating that the present compounds bind to ex vivo tissue grafts and are useful in methods of detecting damaged tissues and/or organs.

Example 10

Evaluation of the Durability and Effectiveness of Self-Assembled Adhesion Barriers As the surfaces of organs are continually exposed to friction as a result of bodily movements (e.g., gastrointestinal movements, breathing, gravity) and because any barrier will be exposed to excessive wear conditions, barrier durability and wear resistance is determined. To test barrier stability, a repeat contact model is used with ex vivo skin patches under dynamic loading [192-194]. In this regard, a small-scale loading machine [195] is outfitted with adjustable platens that ensure parallel loading to the tissue surface.

Figure 48:
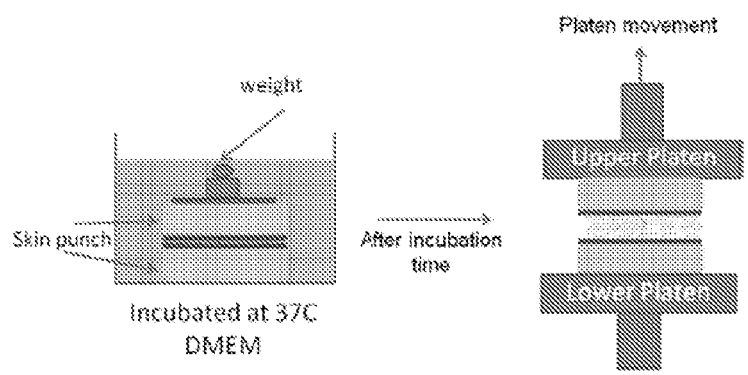
FIG. 48 is a schematic diagram of an in vitro model of adhesion resistance to determine durability and wear resistance of an exemplary polymeric compound.

As a test of the analysis procedure, a static load contact model was performed (FIG. 48). Briefly, two rabbit full thickness skin biopsies (6 mm diameter) were placed into basal side contact and incubated in HPSS buffer at 37° C. under a 5 gram load for 15 min to 4 hr. After this incubation, tissues were mounted in the loading machine to the top and bottom platens via 10 µl dermabond without separating the layers. The cyanoacrylate was allowed to set (50 g load, 2 minutes) followed by retraction of tissues at a constant rate (1 mm/min). Both Force (250 g load cell) and displacement (25 mm displacement sensor) were recorded in real time until complete separation was obtained.

Figure 49:
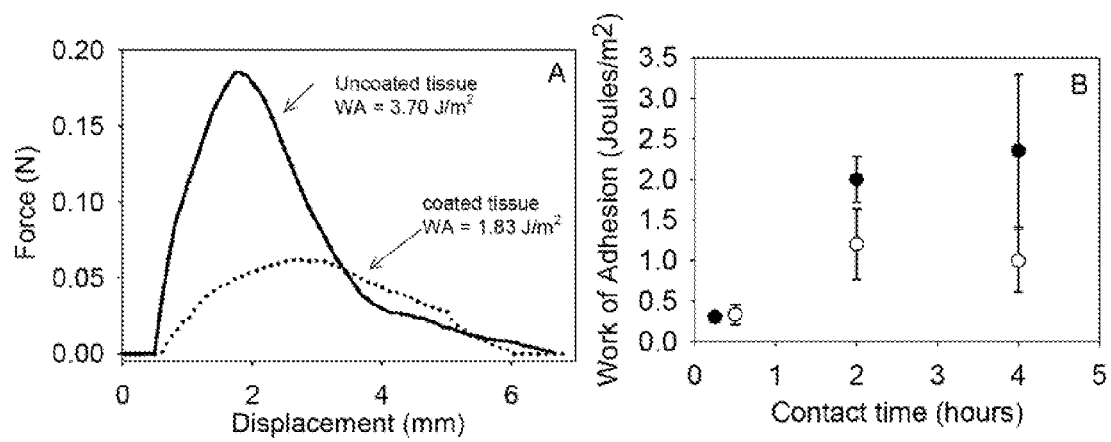
FIGS. 49A and 49B are graphs showing the force required to displace skin samples that were incubated in contact with a constant 5 gram load in HEPES buffer (FIG. 49A), where prior to contact, the skin samples were either covered with a 100 μl of 1 mg/ml a polymer compound in PBS (coated) or with control 100 μl PBS (uncoated), and showing the work of adhesion as a function of contact time (FIG. 49B), where as contact time increased, work of adhesion increased, and where coated (○) samples possessed a lower work of adhesion than uncoated (●) samples.

After subtracting the weight of the platen and the tissue, the force of adhesion was calculated by integrating the force vs. strain curve (FIG. 49A). In this regard, skin samples were incubated in contact with a constant 5 gram load in HEPES buffer and, prior to contact, skin samples were either covered with a 100 µl of 1 mg/ml PEG-PMA polymer in PBS (coated) or with control 100 µl PBS (uncoated). Work of adhesion was determined through integration of the curve divided by the initial area of contact. As contact time increased, work of adhesion increased; coated (O) samples possessed a lower work of adhesion than uncoated (●) samples (FIG. 49B). Further, data suggests that this work of adhesion was decreased when even a single non-targeted layer polymer layer was added to the skin samples.

Throughout this document, various references are mentioned. All such references are incorporated herein by reference, including the references set forth in the following list:

REFERENCES

1. Boland, G. M. and R. J. Weigel, Formation and prevention of postoperative abdominal adhesions. J Surg Res, 2006. 132(1): p. 3-12.
2. Weis, C., et al., Poly(vinyl alcohol) membranes for adhesion prevention. J Biomed Mater Res B Appl Biomater, 2004. 70(2): p. 191-202.
3. diZerega, G. S., Biochemical events in peritoneal tissue repair. Eur J Surg Suppl, 1997(577): p. 10-6.
4. Control and prevention of peritoneal adhesions in gynecologic surgery. Feral Steril, 2006. 86(5 Suppl): p. S1-5.
5. Ellis, H., et al., Adhesion-related hospital readmissions after abdominal and pelvic surgery: a retrospective cohort study. Lancet, 1999. 353(9163): p. 1476-80.
6. Risberg, B., Adhesions: preventive strategies. Eur J Surg Suppl, 1997(577): p. 32-9.
7. Matthews, B. D., et al., Assessment of adhesion formation to intra-abdominal polypropylene mesh and polytetrafluoroethylene mesh. J Surg Res, 2003. 114(2): p. 126-32.
8. Nagelschmidt, M., T. Minor, and S. Saad, Polyethylene glycol 4000 attenuates adhesion formation in rats by suppression of peritoneal inflammation and collagen incorporation. Am J Surg, 1998. 176(1): p. 76-80.
9. Medley, J. M. and T. D. Dziubla, Prevention of Post-Surgical Adhesions: A Biomaterials Perspective, in Biological Interactions on Materials Surfaces: Understanding and Controlling Protein, Cell, and Tissue Responses, R. Bizios and D. A. Puleo, Editors. 2009, Elsevier: New York.
10. Sittinger, M., et al., Tissue engineering and autologous transplant formation: practical approaches with resorbable biomaterials and new cell culture techniques. Biomaterials, 1996. 17(3): p. 237-42.
11. Al-Took, S., R. Platt, and T. Tulandi, Adhesion-related small-bowel obstruction after gynecologic operations. Am J Obstet Gynecol, 1999. 180(2 Pt 1): p. 313-5.
12. Miller, G., et al., Etiology of small bowel obstruction. Am J Surg, 2000. 180(1): p. 33-6.
13. Diamond, M. P. and M. L. Freeman, Clinical implications of postsurgical adhesions. Hum Reprod Update, 2001. 7(6): p. 567-76.
14. Tulandi, T. and A. Al-Shahrani, Adhesion prevention in gynecologic surgery. Curr Opin Obstet Gynecol, 2005. 17(4): p. 395-8.
15. Kresch, A. J., et al., Laparoscopy in 100 women with chronic pelvic pain. Obstet Gynecol, 1984. 64(5): p. 672-4.

16: Swank, D. J., et al., Laparoscopic adhesiolysis in patients with chronic abdominal pain: a blinded randomised controlled multi-centre trial. Lancet, 2003. 361(9365): p. 1247-51.
17. Dijkstra, F. R., et al., Recent clinical developments in pathophysiology, epidemiology, diagnosis and treatment of intra-abdominal adhesions. Scand J Gastroenterol Suppl, 2000(232): p. 52-9.
18. Brill, A. I., et al., The incidence of adhesions after prior laparotomy: a laparoscopic appraisal. Obstet Gynecol, 1995. 85(2): p. 269-72.
19. Cheong, Y. C., N. Bajekal, and T. C. Li, Peritoneal closure—to close or not to close. Hum Reprod, 2001. 16(8): p. 1548-52.
20. Lyell, D. J., et al., Peritoneal closure at primary cesarean delivery and adhesions. Obstet Gynecol, 2005. 106(2): p. 275-80.
21. Roset, E., M. Boulvain, and O. Irion, Nonclosure of the peritoneum during caesarean section: long-term follow-up of a randomised controlled trial. Eur J Obstet Gynecol Reprod Biol, 2003. 108(1): p. 40-4.
22. Setzen, G. and E. F. Williams, 3rd, Tissue response to suture materials implanted subcutaneously in a rabbit model. Plast Reconstr Surg, 1997. 100(7): p. 1788-95.
23. Merad, F., et al., Prophylactic abdominal drainage after elective colonic resection and suprapromontory anastomosis: a multicenter study controlled by randomization. French Associations for Surgical Research. Arch Surg, 1998. 133(3): p. 309-14.
24. Memon, M. A., et al., The uses and abuses of drains in abdominal surgery. Hosp Med, 2002. 63(5): p. 282-8.
25. Memon, M. A., M. I. Memon, and J. H. Donohue, Abdominal drains: a brief historical review. Ir Med J, 2001. 94(6): p. 164-6.
26. Bertram, P., et al., Effects of intra-abdominal drainages on adhesion formation and prevention by phospholipids in a rat model. Drainages and adhesion formation. Eur Surg Res, 2003. 35(2): p. 92-7.
27. Schein, M., To drain or not to drain? The role of drainage in the contaminated and infected abdomen: an international and personal perspective. World J Surg, 2008. 32(2): p. 312-21.
28. Matsuzaki, S., et al., Effects of supplemental perioperative oxygen on post-operative abdominal wound adhesions in a mouse laparotomy model with controlled respiratory support. Hum Reprod, 2007. 22(10): p. 2702-6.
29. Gutt, C. N., et al., Fewer adhesions induced by laparoscopic surgery? Surg Endosc, 2004. 18(6): p. 898-906.
30. Milingos, S., et al., Adhesions: laparoscopic surgery versus laparotomy. Ann N Y Acad Sci, 2000. 900: p. 272-85.
31. Pattaras, J. G., et al., Incidence of postoperative adhesion formation after transperitoneal genitourinary laparoscopic surgery. Urology, 2002. 59(1): p. 37-41.
32. Muller, S. A., et al., Adhesion prevention comparing liquid and solid barriers in the rabbit uterine horn model. Eur J Obstet Gynecol Reprod Biol, 2005. 120(2): p. 222-6.
33. Cooper, K., et al., Reduction of post-surgical adhesion formation with tranilast. J Surg Res, 2007. 141(2): p. 153-61.
34. Stramer, B. M., R. Mori, and P. Martin, The inflammation-fibrosis link? A Jekyll and Hyde role for blood cells during wound repair. J Invest Dermatol, 2007. 127(5): p. 1009-17.
35. Knight, J. A., Review: Free radicals, antioxidants, and the immune system. Ann Clin Lab Sci, 2000. 30(2): p. 145-58.
36. Peterhans, E., Oxidants and antioxidants in viral diseases: disease mechanisms and metabolic regulation. J Nutr, 1997. 127(5 Suppl): p. 962S-965S.
37. Prakash Kumar, B. and K. Shivakumar, Alterations in collagen metabolism and increased fibroproliferation in the heart in cerium-treated rats: implications for the pathogenesis of endomyocardial fibrosis. Biol Trace Elem Res, 1998. 63(1): p. 73-9.
38. Wilgus, T. A., et al., Hydrogen peroxide disrupts scarless fetal wound repair. Wound Repair Regen, 2005. 13(5): p. 513-9.
39. ten Raa, S., et al., The role of neutrophils and oxygen free radicals in post-operative adhesions. J Surg Res, 2006. 136(1): p. 45-52.
40. Portilla, F. d. l., et al., Prevention of Peritoneal Adhesions by Intraperitoneal Administration of Vitamin E: An Experimental Study in Rats. Diseases of the Colon & Rectum, 2004. 47(12): p. 2157-2161.
41. Demirbag, S., et al., Comparison of hyaluronate/carboxymethylcellulose membrane and melatonin for prevention of adhesion formation in a rat model. Hum Reprod, 2005. 20(7): p. 2021-4.
42. Yuzbasioglu, M. F., et al., The effect of intraperitoneal catalase on prevention of peritoneal adhesion formation in rats. J Invest Surg, 2008. 21(2): p. 65-9.
43. Johns, A., Evidence-based prevention of post-operative adhesions. Hum Reprod Update, 2001. 7(6): p. 577-9.
44. Hellebrekers, B. W., et al., A role for the fibrinolytic system in postsurgical adhesion formation. Fertil Steril, 2005. 83(1): p. 122-9.
45. Hellebrekers, B. W., et al., Short-term effect of surgical trauma on rat peritoneal fibrinolytic activity and its role in adhesion formation. Thromb Haemost, 2000. 84(5): p. 876-81.
46. Hellebrekers, B. W., et al., Use of fibrinolytic agents in the prevention of postoperative adhesion formation. Fertil Steril, 2000. 74(2): p. 203-12.
47. Whitting, H. W. and B. A. Young, The effect of varidase in carboxymethylcellulose jelly on peritoneal adhesion formation. Virchows Arch Pathol Anat Physiol Klin Med, 1966. 341(2): p. 155-63.
48. D'Amico, G., [Experimental research on the effect of varidase on peritoneal adhesions.]. Riv Patol Clin, 1954. 9(1): p. 23-36.
49. Schutze, U., et al., [Prophylaxis of peritoneal adhesions with streptokinase and streptodornase (Varidase). An experimental study in animals (author's transl)]. MMW Munch Med Wochenschr, 1977. 119(4): p. 123-6.
50. Hill-West, J. L., R. C. Dunn, and J. A. Hubbell, Local release of fibrinolytic agents for adhesion prevention. J Surg Res, 1995. 59(6): p. 759-63.
51. Jewett, T. C., Jr., et al., Effects of Fibrinolytic Enzymes on Experimentally Induced Peritoneal Adhesions. Surgery, 1965. 57: p. 280-4.
52. Okamoto, Y., S. Takai, and M. Miyazaki, Oral administration of a novel chymase inhibitor, NK3201, prevents peritoneal adhesion formation in hamsters. Jpn J Pharmacol, 2002. 90(1): p. 94-6.
53. David-Raoudi, M., et al., Differential effects of hyaluronan and its fragments on fibroblasts: relation to wound healing. Wound Repair Regen, 2008. 16(2): p. 274-87.
54. Turley, E. A., Hyaluronan and cell locomotion. Cancer Metastasis Rev, 1992. 11(1): p. 21-30.
55. Moore, A. R., et al., The chemotactic properties of cartilage glycosaminoglycans for polymorphonuclear neutrophils. Int J Tissue React, 1989. 11(6): p. 301-7.
56. Gao, F., et al., Hyaluronan oligosaccharides are potential stimulators to angiogenesis via RHAMM mediated signal pathway in wound healing. Clin Invest Med, 2008. 31(3): p. E106-16.

57. Sawada, T., et al., Adhesion preventive effect of hyaluronic acid after intraperitoneal surgery in mice. Hum Reprod, 1999. 14(6): p. 1470-2.
58. Shushan, A., et al., Hyaluronic acid for preventing experimental postoperative intraperitoneal adhesions. J Reprod Med, 1994. 39(5): p. 398-402.
59. Detchev, R., et al., Prevention of de novo adhesion by ferric hyaluronate gel after laparoscopic surgery in an animal model. JSLS, 2004. 8(3): p. 263-8.
60. Johns, D. B., et al., Reduction of postsurgical adhesions with Intergel adhesion prevention solution: a multicenter study of safety and efficacy after conservative gynecologic surgery. Fertil Steril, 2001. 76(3): p. 595-604.
61. Wiseman, D. M., Possible Intergel Reaction Syndrome (pIRS). Ann Surg, 2006. 244(4): p. 630-2.
62. Yeo, Y., et al., In situ cross-linkable hyaluronic acid hydrogels prevent post-operative abdominal adhesions in a rabbit model. Biomaterials, 2006. 27(27): p. 4698-705.
63. Guida, M., et al., Effectiveness of auto-crosslinked hyaluronic acid gel in the prevention of intrauterine adhesions after hysteroscopic surgery: a prospective, randomized, controlled study. Hum Reprod, 2004. 19(6): p. 1461-4.
64. Pellicano, M., et al., Effectiveness of autocrosslinked hyaluronic acid gel after laparoscopic myomectomy in infertile patients: a prospective, randomized, controlled study. Fertil Steril, 2003. 80(2): p. 441-4.
65. Mazzone, A., et al., Pharmacological effect of hyaluronic acid (HA) on phagocytes: hypothesis for an HA-induced monocyte chemotactic factor for neutrophils. Clin Ther, 1986. 8(5): p. 527-36.
66. Bulpitt, P. and D. Aeschlimann, New strategy for chemical modification of hyaluronic acid: preparation of functionalized derivatives and their use in the formation of novel biocompatible hydrogels. J Biomed Mater Res, 1999. 47(2): p. 152-69.
67. Jia, X., et al., Prolongation of sciatic nerve blockade by in situ cross-linked hyaluronic acid. Biomaterials, 2004. 25(19): p. 4797-804.
68. Ito, T., et al., The prevention of peritoneal adhesions by in situ cross-linking hydrogels of hyaluronic acid and cellulose derivatives. Biomaterials, 2007. 28(6): p. 975-83.
69. Diamond, M. P., Reduction of adhesions after uterine myomectomy by Seprafilm membrane (HAL-F): a blinded, prospective, randomized, multicenter clinical study. Seprafilm Adhesion Study Group. Fertil Steril, 1996. 66(6): p. 904-10.
70. Kelekci, S., et al., The efficacy of a hyaluronate/carboxymethylcellulose membrane in prevention of postoperative adhesion in a rat uterine horn model. Tohoku J Exp Med, 2004. 204(3): p. 189-94.
71. FDA Panel Recommends Against Approval of Genzyme General's Sepracoat 1997 [cited 2008 Sep. 16, 2008]; Available from: www.prnewswire.com.
72. Hills, B. A., B. D. Butler, and R. E. Barrow, Boundary lubrication imparted by pleural surfactants and their identification. J Appl Physiol, 1982. 53(2): p. 463-9.
73. Muller, S. A., et al., Efficacy of adhesion prevention and impact on wound healing of intraperitoneal phospholipids. J Surg Res, 2001. 96(1): p. 68-74.
74. Muller, S. A., et al., Influence of intraperitoneal phospholipid dosage on adhesion formation and wound healing at different intervals after surgery. Langenbecks Arch Surg, 2001. 386(4): p. 278-84.
75. Treutner, K. H., et al., Prevention of postoperative adhesions by single intraperitoneal medication. J Surg Res, 1995. 59(6): p. 764-71.
76. Baxter, ADEPT Instructions for Use: Deerfield, Ill.
77. Verco, S. J., et al., Development of a novel glucose polymer solution (icodextrin) for adhesion prevention: preclinical studies. Hum Reprod, 2000. 15(8): p. 1764-72.
78. Hosie, K., et al., Fluid Dynamics in Man of an Intraperitoneal Drug Delivery Solution: 4% Icodextrin. Drug Delivery, 2001. 8(1): p. 9-12.
79. Menzies, D., et al., Use of icodextrin 4% solution in the prevention of adhesion formation following general surgery: from the multicentre ARIEL Registry. Aim R Coll Surg Engl, 2006. 88(4): p. 375-82.
80. van den Tol, P., et al., Icodextrin reduces postoperative adhesion formation in rats without affecting peritoneal metastasis. Surgery, 2005. 137(3): p. 348-54.
81. Brown, C. B., et al., Adept (icodextrin 4% solution) reduces adhesions after laparoscopic surgery for adhesiolysis: a double-blind, randomized, controlled study. Fertil Steril, 2007. 88(5): p. 1413-26.
82. Wallwiener, M., et al., Innovative barriers for peritoneal adhesion prevention: liquid or solid? A rat uterine horn model. Fertil Steril, 2006. 86 Suppl 4: p. 1266-76.
83. Krsko, P. and M. Libera, Biointeractive hydrogels. Materials Today, 2005. 8(12): p. 36-44.
84. Hildebrand, H. F., et al., Surface coatings for biological activation and functionalization of medical devices. Surface and Coatings Technology, 2006. 200(22-23): p. 6318-6324.
85. Lundorff, P., et al., Clinical evaluation of a viscoelastic gel for reduction of adhesions following gynaecological surgery by laparoscopy in Europe. Hum Reprod, 2005. 20(2): p. 514-20.
86. Nehez, L., et al., Prevention of postoperative peritoneal adhesions: effects of lysozyme, polylysine and polyglutamate versus hyaluronic acid. Scand J Gastroenterol, 2005. 40(9): p. 1118-23.
87. Nehez, L., et al., Differently charged polypeptides in the prevention of post-surgical peritoneal adhesions. Scand J Gastroenterol, 2007. 42(4): p. 519-23.
88. Kapadia, M. R., D. A. Popowich, and M. R. Kibbe, Modified prosthetic vascular conduits. Circulation, 2008. 117 (14): p. 1873-82.
89. Adam, D. J., et al., Antiplatelet and anticoagulant therapy to prevent bypass graft thrombosis in patients with lower extremity arterial occlusive disease. Int Angiol, 2001. 20(1): p. 90-8.
90. Kenny, D. A., et al., Experimental comparison of the thrombogenicity of fibrin and PTFE flow surfaces. Ann Surg, 1980. 191(3): p. 355-61.
91. Patel, M., et al., Experimental evaluation of ten clinically used arterial prostheses. Ann Vasc Surg, 1992. 6(3): p. 244-51.
92. Harris, E. S., R. F. Morgan, and G. T. Rodeheaver, Analysis of the kinetics of peritoneal adhesion formation in the rat and evaluation of potential antiadhesive agents. Surgery, 1995. 117(6): p. 663-9.
93. Hellebrekers, B. W., et al., Effects of five different barrier materials on postsurgical adhesion formation in the rat. Hum Reprod, 2000. 15(6): p. 1358-63.
94. Montz, F. J., B. J. Monk, and S. M. Lacy, The Gore-Tex Surgical Membrane: effectiveness as a barrier to inhibit postradical pelvic surgery adhesions in a porcine model. Gynecol Oncol, 1992. 45(3): p. 290-3.
95. Haney, A. F. and E. Doty, A barrier composed of chemically cross-linked hyaluronic acid (Incert) reduces postoperative adhesion formation. Fertil Steril, 1998. 70(1): p. 145-51.

96. Himeda, Y., et al., Application of Biocompatible Gel of Hyaluronic Acid in Adhesion Prevention. Journal of Gynecologic Surgery, 2004. 20(2): p. 39-46.
97. Stuart, M., Breaking the Surgical Adhesion Barrier. Start-Up, 2005(April): p. 16-22.
98. Ferland, R., D. Mulani, and P. K. Campbell, Evaluation of a sprayable polyethylene glycol adhesion barrier in a porcine efficacy model. Hum Reprod, 2001. 16(12): p. 2718-23.
99. Dunn, R., et al., Evaluation of the SprayGel adhesion barrier in the rat cecum abrasion and rabbit uterine horn adhesion models. Fertil Steril, 2001. 75(2): p. 411-6.
100. Rodgers, K., et al., Evaluation of polyethylene glycol/polylactic acid films in the prevention of adhesions in the rabbit adhesion formation and reformation sidewall models. Fertil Steril, 1998. 69(3): p. 403-8.
101. Zeng, Q., et al., Efficacy and safety of Seprafilm for preventing postoperative abdominal adhesion: systematic review and meta-analysis. World J Surg, 2007. 31(11): p. 2125-31; discussion 2132.
102. Shinohara, T., et al., A simple and novel technique for the placement of antiadhesive membrane in laparoscopic surgery. Surg Laparosc Endosc Percutan Tech, 2008. 18(2): p. 188-91.
103. Mettler, L., et al., A randomized, prospective, controlled, multicenter clinical trial of a sprayable, site-specific adhesion barrier system in patients undergoing myomectomy. Fertil Steril, 2004. 82(2): p. 398-404.
104. Jackson, J. K., et al., Paclitaxel-loaded crosslinked hyaluronic acid films for the prevention of postsurgical adhesions. Pharm Res, 2002. 19(4): p. 411-7.
105. Yagmurlu, A., et al., Reduction of surgery-induced peritoneal adhesions by continuous release of streptokinase from a drug delivery system. Eur Surg Res, 2003. 35(1): p. 46-9.
106. Yeo, Y., et al., Prevention of peritoneal adhesions with an in situ cross-linkable hyaluronan hydrogel delivering budesonide. J Control Release, 2007. 120(3): p. 178-85.
107. Leach, R. E., et al., Reduction of postsurgical adhesion formation in the rabbit uterine horn model with use of hyaluronate/carboxymethylcellulose gel. Fertil Steril, 1998. 69(3): p. 415-8.
108. Cheung, M., et al., Development of a Swine Model for the Evaluation of Novel Compounds in the Prevention of Pelvic Adhesions, in ISPE Great Lakes Chapter Meeting. 2008: Chicago, Ill.
109. Alemany, R., Designing adenoviral vectors for tumor-specific targeting. Methods Mol Biol, 2009. 542: p. 57-74.
110. Engelman, J. A., Targeting PI3K signalling in cancer: opportunities, challenges and limitations. Nat Rev Cancer, 2009. 9(8): p. 550-62.
111. Gordon, I. O., et al., Update in neoplastic lung diseases and mesothelioma. Arch Pathol Lab Med, 2009. 133(7): p. 1106-15.
112. Jia, L. J. and Z. C. Hua, Development of bacterial vectors for tumor-targeted gene therapy. Methods Mol Biol, 2009. 542: p. 131-54.
113. Sandoval, D. A., S. Obici, and R. J. Seeley, Targeting the CNS to treat type 2 diabetes. Nat Rev Drug Discov, 2009. 8(5): p. 386-98.
114. Telvekar, V. N. and H. S. Kundaikar, GPR40 carboxylic acid receptor family and diabetes: a new drug target. Curr Drug Targets, 2008. 9(10): p. 899-910.
115. Yu, X., E. Patterson, and D. C. Kern, Targeting proteasomes for cardioprotection. Curr Opin Pharmacol, 2009. 9(2): p. 167-72.
116. Anderson, J. C., B. C. McFarland, and C. L. Gladson, New molecular targets in angiogenic vessels of glioblastoma tumours. Expert Rev Mol Med, 2008. 10: p. e23.
117. Brown, J. M. and A. J. Giaccia, The unique physiology of solid tumors: opportunities (and problems) for cancer therapy. Cancer Res, 1998. 58(7): p. 1408-16.
118. Dvorak, H. F., Leaky tumor vessels: consequences for tumor stroma generation and for solid tumor therapy. Prog Clin Biol Res, 1990. 354A: p. 317-30.
119. Karmali, P. P., et al., Targeting of albumin-embedded paclitaxel nanoparticles to tumors. Nanomedicine, 2009. 5(1): p. 73-82.
120. Park, J. H., et al., Systematic surface engineering of magnetic nanoworms for in vivo tumor targeting. Small, 2009. 5(6): p. 694-700.
121. Simberg, D., et al., Biomimetic amplification of nanoparticle homing to tumors. Proc Natl Acad Sci USA, 2007. 104(3): p. 932-6.
122. Zanuy, D., et al., In Silico Molecular Engineering for a Targeted Replacement in a Tumor-Homing Peptide. J Phys Chem B, 2009.
123. Zanuy, D., et al., Influence of the dye presence on the conformational preferences of CREKA, a tumor homing linear pentapeptide. Biopolymers, 2009. 92(2): p. 83-93.
124. Zanuy, D., et al., The energy landscape of a selective tumor-homing pentapeptide. J Phys Chem B, 2008. 112 (29): p. 8692-700.
125. Kutlay, J., et al., Comparative effectiveness of several agents for preventing postoperative adhesions. World J Surg, 2004. 28(7): p. 662-5.
126. diZerega, G. S. and J. D. Campeau, Peritoneal repair and post-surgical adhesion formation. Hum Reprod Update, 2001. 7(6): p. 547-55.
127. Moreira, H., Jr., et al., Use of bioresorbable membrane (sodium hyaluronate+carboxymethylcellulose) after controlled bowel injuries in a rabbit model. Dis Colon Rectum, 2000. 43(2): p. 182-7.
128. Doan, K. T., R. J. Olson, and N. Mamalis, Survey of intraocular lens material and design. Curr Opin Ophthalmol, 2002. 13(1): p. 24-9.
129. Eppley, B. L. and B. Dadvand, Injectable soft-tissue fillers: clinical overview. Plast Reconstr Surg, 2006. 118 (4): p. 98e-106e.
130. Revell, P. A., M. Braden, and M. A. Freeman, Review of the biological response to a novel bone cement containing poly(ethyl methacrylate) and n-butyl methacrylate. Biomaterials, 1998. 19(17): p. 1579-86.
131. Sclafani, A. P. and T. Romo, 3rd, Injectable fillers for facial soft tissue enhancement. Facial Plast Surg, 2000. 16(1): p. 29-34.
132. Hilgers, L. A., et al., Alkyl-esters of polyacrylic acid as vaccine adjuvants. Vaccine, 1998. 16(16): p. 1575-81.
133. Oka, T., et al., Influenza vaccine: enhancement of immune response by application of carboxy-vinylpolymer. Vaccine, 1990. 8(6): p. 573-6.
134. Ratner, B. D. and S. J. Bryant, Biomaterials: where we have been and where we are going. Annu Rev Biomed Eng, 2004. 6: p. 41-75.
135. Saltzman, W. M., Drug delivery: engineering principles for drug therapy. 2001, Oxford England; New York: Oxford University Press. xi, 372.
136. Hildebrand, H. F., et al., Surface coatings for biological activation and functionalization of medical devices. Surface and Coatings Technology, 2006. 200: p. 6318-6324.
137. Ho, D. H., et al., Clinical pharmacology of polyethylene glycol-L-asparaginase. Drug Metab Dispos, 1986. 14(3): p. 349-52.

138. Saiki, I., et al., Antimetastatic activity of polymeric RGDT peptides conjugated with poly(ethylene glycol). Jpn J Cancer Res, 1993. 84(5): p. 558-65.

139. Teppler, H., et al., Prolonged immunostimulatory effect of low-dose polyethylene glycol interleukin 2 in patients with human immunodeficiency virus type 1 infection. J Exp Med, 1993. 177(2): p. 483-92.

140. Gref, R., et al., 'Stealth' corona-core nanoparticles surface modified by polyethylene glycol (PEG): influences of the corona (PEG chain length and surface density) and of the core composition on phagocytic uptake and plasma protein adsorption. Colloids Surf B Biointerfaces, 2000. 18(3-4): p. 301-313.

141. Butun, V., et al., Synthesis and aqueous solution properties of novel neutral/acidic block copolymers. Polymer, 2000. 41(9): p. 3173-3182.

142. Hadjiyannakou, S. C., M. Vamvakaki, and C. S. Patrickios, Synthesis, characterization and evaluation of amphiphilic diblock copolymer emulsifiers based on methoxy hexa(ethylene glycol) methacrylate and benzyl methacrylate. Polymer, 2004. 45(8): p. 2433-2442.

143. Triftaridou, A. I., M. Vamvakaki, and C. S. Patrickios, Amphiphilic diblock and ABC triblock methacrylate copolymers: synthesis and aqueous solution characterization. Polymer, 2002. 43(10): p. 2921-2926.

144. Vamvakaki, M., N. C. Billingham, and S. P. Armes, Synthesis of water-soluble statistical copolymers and terpolymers containing pendent oligo(ethylene glycol derivatives). Polymer, 1999. 40(18): p. 5161-5171.

145. Rannard, S. P., et al., Synthesis of monodisperse block copolymers containing methacrylic acid segments by group transfer polymerization: choice of protecting group and catalyst. European Polymer Journal, 1993. 29(2/3): p. 407-414.

146. Dicker, I. B., et al., Oxyanions Catalyze Group-Transfer Polymerization To Give Living Polymers. Macromolecules, 1990. 23: p. 4034-4041.

147. Arano, Y., et al., Reassessment of diethylenetriaminepentaacetic acid (DTPA) as a chelating agent for indium-111 labeling of polypeptides using a newly synthesized monoreactive DTPA derivative. J Med Chem, 1996. 39(18): p. 3451-60.

148. Boeckler, C., B. Frisch, and F. Schuber, Design and synthesis of thiol-reactive lipopeptides. Bioorg Med Chem Lett, 1998. 8(15): p. 2055-8.

149. Neises, B. and W. Steglich, Simple Method for the Esterification of Carboxylic Acids. Angew. Chem. Int. Ed. Engl., 1978. 17(7): p. 522-524.

150. Sheehan, J. C. and G. P. Hess, A New Method of Forming Peptide Bonds. Journal of the American Chemical Society, 1955. 77(4): p. 1067-1068.

151. Odian, G. G., Principles of polymerization. 4th ed. 2004, Hoboken, N. J.: Wiley-Interscience. xxiv, 812.

152. Medley, J. M., et al., Block copolymers for the rational design of self-forming postsurgical adhesion barriers. Acta Biomater, 2009.

153. How to Prepare Self-Assembled Monolayers, in Self-Assembling Molecules. 2005, Asemblon, Inc. p. 2-6.

154. Variations in the Assembly Protocol for Carboxy- and Amine-Terminated Alkanethiols, in Self-Assembly Procedure for Carboxy- and Amine-Terminated Alkanethiols. 2005, Asemblon, Inc. p. 2-3.

155. Wang, H., et al., Improved Method for the Preparation of Carboxylic Acid and Amine Terminated Self-Assembled Monolayers of Alkanethiolates. Langmuir, 2005. 21(7): p. 2633-2636.

156. Cleaning-UVO Treatment, in Methods and Protocols. 2007, Q-Sense Methods and Protocols. p. 1-16.

157. Sauerbrey, G., Zeitschrift für Physik, 1959. 155: p. 206.

158. Reimhult, K., K. Petersson, and A. Krozer, QCM-D analysis of the performance of blocking agents on gold and polystyrene surfaces. Langmuir, 2008. 24(16): p. 8695-700.

159. Höök, F., et al., A comparative study of protein adsorption on titanium oxide surfaces using in situ ellipsometry, optical waveguide lightmode spectroscopy, and quartz crystal microbalance/dissipation. Colloids and Surfaces B: Biointerfaces, 2002. 24(2): p. 155-170.

160. Tompkins, H. G. and W. A. McGahan, Spectroscopic ellipsometry and reflectometry: a user's guide. 1999, New York: Wiley. xiv, 228 p.

161. Hanson, A. D., et al., Effects of oxygen plasma treatment on adipose-derived human mesenchymal stem cell adherence to poly(L-lactic acid) scaffolds. Journal of Biomaterials Science-Polymer Edition, 2007. 18(11): p. 1387-1400.

162. Mona, M., et al., Collagen I-coated titanium surfaces: mesenchymal cell adhesion and in vivo evaluation in trabecular bone implants. Journal of Biomedical Materials Research Part A, 2006. 78A(3): p. 449-458.

163. Ahmed, T. A. E., E. V. Dare, and M. Hincke, Fibrin: A versatile scaffold for tissue engineering applications. Tissue Engineering Part B-Reviews, 2008. 14(2): p. 199-215.

164. Ahn, H. H., et al., Polyethyleneimine-mediated gene delivery into human adipose derived stem cells. Biomaterials, 2008. 29(15): p. 2415-2422.

165. Jeon, J. H., M. V. Thomas, and D. A. Puleo, Bioerodible devices for intermittent release of simvastatin acid. Int J Pharm, 2007. 340(1-2): p. 6-12.

166. Labarca, C. and K. Paigen, A simple, rapid, and sensitive DNA assay procedure. Anal Biochem, 1980. 102(2): p. 344-52.

167. Höök, F., et al., Energy dissipation kinetics for protein and antibody-antigen adsorption under shear oscillation on a quartz crystal microbalance. Langmuir, 1998. 14(4): p. 729-734.

168. Fan, X., L. Lin, and P. B. Messersmith, Cell fouling resistance of polymer brushes grafted from ti substrates by surface-initiated polymerization: effect of ethylene glycol side chain length. Biomacromolecules, 2006. 7(8): p. 2443-8.

169. Nappi, C., et al., Prevention of adhesions in gynaecological endoscopy. Hum Reprod Update, 2007. 13(4): p. 379-94.

170. Höök, F. and B. Kasemo, The QCM-D Technique for Probing Biomacromolecular Recognition Reactions, in Piezoelectric Sensors. 2007. p. 425-447.

171. Höök, F., et al., Dissipative QCM-D technique: Interfacial phenomena and sensor applications for proteins, biomembranes, living cells and polymers. Proceedings of the Annual IEEE International Frequency Control Symposium, 1999. 2: p. 966-972.

172. Reimhult, E., et al., Simultaneous surface plasmon resonance and quartz crystal microbalance with dissipation monitoring measurements of biomolecular adsorption events involving structural transformations and variations in coupled water. Analytical Chemistry, 2004. 76(24): p. 7211-7220.

173. Jung, H., et al., Change of viscoelastic property and morphology of fibrin affected by antithrombin III and heparin: QCM-Z and AFM study. Colloids Surf B Biointerfaces, 2009. 68(1): p. 111-9.

174. Riedel, T., et al., Controlled preparation of thin fibrin films immobilized at solid surfaces. J Biomed Mater Res A, 2009. 88(2): p. 437-47.
175. Kroh, H. K., P. Panizzi, and P. E. Bock, Von Willebrand factor-binding protein is a hysteretic conformational activator of prothrombin. Proc Natl Acad Sci USA, 2009. 106(19): p. 7786-91.
176. Wolberg, A. S., D. A. Gabriel, and M. Hoffman, Analyzing fibrin clot structure using a microplate reader. Blood Coagul Fibrinolysis, 2002. 13(6): p. 533-9.
177. Walpole, R. E. and R. H. Myers, Probability and Statistics for Engineers and Scientists. 3rd ed. 1985, New York: Macmillan.
178. National Institute of Standards and Technology (U.S.) and International SEMATECH. Engineering Statistics Handbook. 2009 [cited Oct. 15, 2009]; Available from: http://www.itl.nist.gov/div898/handbook/index2.htm.
179. Vardeman, S. B., Statistics for Engineering Problem Solving. 1994, Boston, Mass.: PWS Publishing.
180. Can, M. E. and D. A. Gabriel, Dextran-Induced Changes in Fibrin Fiber Size and Density Based on Wavelength Dependence of Gel Turbidity. Macromolecules, 1980. 13: p. 1473-1477.
181. Can, M. E., Jr. and J. Hermans, Size and density of fibrin fibers from turbidity. Macromolecules, 1978. 11(1): p. 46-50.
182. Sato, H. and A. Nakajima, Kinetic study on the initial stage of the fibrinogen-fibrin conversion by thrombin. (1) Application of mathematical treatment to turbidimetrical method. Thromb Res, 1984. 33(6): p. 645-51.
183. Sato, H., E. Nakanishi, and A. Nakajima, Kinetic Study on the Initial Stage of Fibrinogen-Fibrin Conversion by Turbidimetry. Colloid and Polymer Science, 1981. 259: p. 1246-1248.
184. Berova, N., K. Nakanishi, and R. W. Woody, Circular Dichroism: Principles and Applications. 2nd ed. 2000, New York: Wiley.
185. Fasman, G. D., Circular Dichroism and the Conformational Analysis of Biomolecules. 1st ed. 2007, New York: Springer-Verlag.
186. Kelly, S. M. and N. C. Price, The use of circular dichroism in the investigation of protein structure and function. Curr Protein Pept Sci, 2000. 1(4): p. 349-84.
187. Rodger, A. and B. Norden, Circular Dichroism and Linear Dichroism. 1997, New York: Oxford University Press.
188. Kelly, S. M., T. J. Jess, and N. C. Price, How to study proteins by circular dichroism. Biochim Biophys Acta, 2005. 1751(2): p. 119-39.
189. Andrade, M. A., et al., Evaluation of secondary structure of proteins from UV circular dichroism spectra using an unsupervised learning neural network. Protein Eng, 1993. 6(4): p. 383-90.
190. Perez-Iratxeta, C. and M. Andrade. K2D2: Estimating Protein Secondary Structure from CD Spectra. [cited 2009 Aug. 23]; Available from: http://www.ogic.ca/projects/k2d2/orainaldia.html.
191. Perez-Iratxeta, C. and M. A. Andrade-Navarro, K2D2: Estimation of protein secondary structure from circular dichroism spectra. BMC Struct Biol, 2008. 8: p. 25.
192. Mortazavi, S A, Smart J D. *Journal of Controlled Release.* 1994; 16; 617-624.
193. Needleman I G, Smales F C. *Biomaterials.* 1995; 16; 617-624.
194. Chapple I L, et al. *J Periodontal Res.* 1999; 34; 79-86.
195. Saunders M, Donahue H. Development of a cost-effective loading machine for biomechanical evaluation of mouse transgenic models. Medical Engineering and Physics. 2004; 26:595-603.

It will be understood that various details of the presently disclosed subject matter can be changed without departing from the scope of the subject matter disclosed herein. Furthermore, the foregoing description is for the purpose of illustration only, and not for the purpose of limitation.

---

What is claimed is:

1. A compound of a formula:

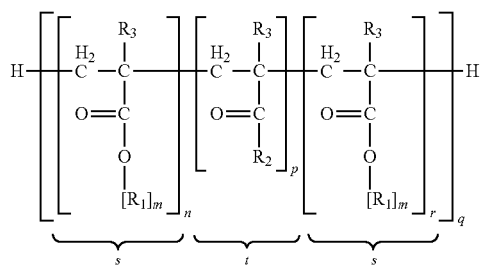

wherein:
- $R_1$ is ethylene glycol;
- $R_2$ is each independently selected from the group consisting of —OH, —OC(CH$_3$)$_3$, an active group, and a basement membrane targeting peptide, wherein at least one $R_2$ is a basement membrane targeting peptide;
- $R_3$ is each independently selected from the group consisting of H and CH$_3$;
- m is an integer from about 10 to about 50;
- n is an integer from about 5 to about 100;
- p is an integer from about 1 to about 100;
- r is an integer from about 0 to about 100; and
- q is an integer from about 1 to about 20, and
- wherein s is a brush-like portion and t is a targeting portion.

2. The compound of claim 1, wherein q is an integer from about 10 to about 20.

3. The compound of claim 1, wherein a ratio of (n+r) to p is about 1 to about 10.

4. The compound of claim 1, wherein the active group is selected from the group consisting of a therapeutic agent and a tag.

5. The compound of claim 4, wherein the tag is a fluorescent tag.

6. The compound of claim 1, wherein the basement membrane targeting peptide comprises a fibrin targeting peptide.

7. The compound of claim 6, wherein the fibrin targeting peptide comprises a sequence of SEQ ID NO: 1.

8. A kit comprising a compound of claim 1 and instructions for using the kit.

9. The kit of claim 8, wherein q is an integer from about 10 to about 20.

10. The kit of claim 8, wherein a ratio of (n+r) to p is about 1 to about 10.

11. The kit of claim 8, wherein the active group is selected from the group consisting of a therapeutic agent and a tag.

12. The kit of claim 11, wherein the tag is a fluorescent tag.

13. The kit of claim 8, wherein the basement membrane targeting peptide comprises a fibrin targeting peptide.

14. The kit of claim 13, wherein the fibrin targeting peptide comprises a sequence of SEQ ID NO: 1.

15. The kit of claim 8, wherein the instructions for using the kit comprise instructions for reducing the occurrence of a post-surgical adhesion.

16. The kit of claim 8, wherein the instructions for using the kit comprise instructions for detecting a damaged tissue surface.

17. A compound of a formula:

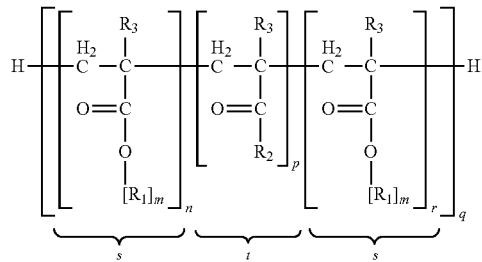

wherein:
- $R_1$ is ethylene glycol;
- $R_2$ is each independently selected from the group consisting of —OH, —OC(CH$_3$)$_3$, an active group, and a basement membrane targeting peptide having the sequence of SEQ ID NO: 1, wherein at least one $R_2$ is a basement membrane targeting peptide having the sequence of SEQ ID NO: 1;
- $R_3$ is each independently selected from the group consisting of H and CH$_3$;
- m is an integer from about 10 to about 50;
- n is an integer from about 5 to about 100;
- p is an integer from about 1 to about 100;
- r is an integer from about 0 to about 100; and
- q is an integer from about 1 to about 20, and
- wherein s is a brush-like portion and t is a targeting portion.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Fibrin Targeting Peptide

<400> SEQUENCE: 1

Cys Arg Glu Lys Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Scrambled fibrin targeting peptide

<400> SEQUENCE: 2

Cys Ala Glu Arg Lys
1               5
```